(12) United States Patent
Savastano et al.

(10) Patent No.: US 12,102,777 B1
(45) Date of Patent: Oct. 1, 2024

(54) DEVICES AND METHODS FOR TRANSVASCULAR DRAINAGE OF FLUIDS IN AN INTRACRANIAL EXTRAVASCULAR SPACE

(71) Applicant: Mayo Foundation for Medical Education and Research, Rochester, MN (US)

(72) Inventors: Luis E. Savastano, Hillsborough, CA (US); Yang Liu, Shanghai (CN)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 18/469,437

(22) Filed: Sep. 18, 2023

Related U.S. Application Data

(63) Continuation of application No. 17/976,667, filed on Oct. 28, 2022, now abandoned, which is a continuation of application No. PCT/US2021/029276, filed on Apr. 27, 2021.

(60) Provisional application No. 63/016,613, filed on Apr. 28, 2020.

(51) Int. Cl.
*A61M 25/00* (2006.01)
*A61M 27/00* (2006.01)

(52) U.S. Cl.
CPC ........ *A61M 25/0082* (2013.01); *A61M 27/00* (2013.01); *A61M 2210/0693* (2013.01)

(58) Field of Classification Search
CPC .......... A61B 18/1492; A61B 17/12031; A61B 17/12109; A61B 17/320016; A61B 2017/12004; A61B 2017/1205; A61B 2017/32004; A61B 2018/00404; A61B 2018/00446; A61B 2018/00577; A61B 2018/00601; A61B 2018/00702; A61B 2217/005; A61B 2218/007
See application file for complete search history.

(56) References Cited

U.S. PATENT DOCUMENTS

| | | | |
|---|---|---|---|
| 6,726,677 B1 * | 4/2004 | Flaherty | A61B 17/3417 604/528 |
| 7,134,438 B2 | 11/2006 | Makower et al. | |
| 7,141,041 B2 | 11/2006 | Seward | |
| 8,663,304 B2 | 3/2014 | Wallace et al. | |
| 9,211,163 B1 * | 12/2015 | Jaramaz | G01R 33/285 |
| 9,585,692 B2 | 3/2017 | Kurth et al. | |

(Continued)

FOREIGN PATENT DOCUMENTS

| | | |
|---|---|---|
| AU | 2020265573 A1 | 11/2021 |
| BR | 202012032342 U2 * | 11/2014 |

(Continued)

OTHER PUBLICATIONS

Co-pending U.S. Appl. No. 18/469,376, inventors Savastano; Luis E et al., filed on Sep. 18, 2023.

(Continued)

*Primary Examiner* — Adam Marcetich
(74) *Attorney, Agent, or Firm* — COOLEY LLP

(57) ABSTRACT

Devices and methods are described for accessing an intracranial extravascular space of a patient. For example, this disclosure describes devices and methods for drainage of a subdural hematoma disposed within an intracranial extravascular space of a patient.

32 Claims, 31 Drawing Sheets

(56) References Cited

U.S. PATENT DOCUMENTS

| | | | |
|---|---|---|---|
| 2002/0169377 A1* | 11/2002 | Khairkhahan | A61B 17/320725 600/433 |
| 2003/0014016 A1 | 1/2003 | Purdy | |
| 2003/0181807 A1* | 9/2003 | Murphy | A61L 31/18 600/411 |
| 2004/0186368 A1 | 9/2004 | Ramzipoor et al. | |
| 2005/0043673 A1* | 2/2005 | Lieberman | A61M 3/0283 604/28 |
| 2005/0148880 A1* | 7/2005 | Tower | A61B 17/3468 600/459 |
| 2005/0240205 A1* | 10/2005 | Berg | A61B 17/11 606/153 |
| 2006/0095066 A1* | 5/2006 | Chang | A61B 17/12136 606/199 |
| 2006/0142782 A1* | 6/2006 | Lieberman | A61M 25/0041 606/108 |
| 2007/0219471 A1* | 9/2007 | Johnson | A61L 31/146 601/6 |
| 2008/0319376 A1* | 12/2008 | Wilcox | A61M 25/00 601/2 |
| 2010/0217276 A1 | 8/2010 | Garrison et al. | |
| 2011/0087261 A1* | 4/2011 | Wittkampf | A61B 17/3478 606/185 |
| 2011/0160621 A1* | 6/2011 | Nita | A61N 7/022 601/2 |
| 2011/0238083 A1 | 9/2011 | Moll et al. | |
| 2012/0059285 A1* | 3/2012 | Soltani | A61M 5/158 601/2 |
| 2012/0330196 A1* | 12/2012 | Nita | A61B 5/0036 601/2 |
| 2014/0324080 A1* | 10/2014 | Wallace | A61B 17/3468 606/159 |
| 2014/0343348 A1* | 11/2014 | Kaplan | A61M 5/158 604/21 |
| 2015/0196741 A1* | 7/2015 | Heilman | A61B 90/39 604/9 |
| 2016/0136398 A1 | 5/2016 | Heilman et al. | |
| 2017/0290598 A1* | 10/2017 | Culbert | A61M 25/0054 |
| 2018/0049759 A1 | 2/2018 | Thomas | |
| 2018/0229010 A1* | 8/2018 | Walzman | A61M 25/1025 |
| 2019/0069949 A1 | 3/2019 | Vrba et al. | |
| 2019/0105477 A1 | 4/2019 | Heilman et al. | |
| 2019/0201093 A1* | 7/2019 | Thom | A61B 18/1815 |
| 2019/0269392 A1* | 9/2019 | Celermajer | A61M 25/0662 |
| 2019/0298977 A1* | 10/2019 | Heilman | A61M 27/006 |
| 2020/0038057 A1* | 2/2020 | Rai | A61M 25/0108 |
| 2020/0069927 A1* | 3/2020 | Malek | A61M 27/006 |
| 2020/0113619 A1* | 4/2020 | Tsukashima | A61B 18/148 |
| 2020/0289061 A1 | 9/2020 | Rapoport et al. | |
| 2020/0375766 A1* | 12/2020 | Malek | A61B 17/3468 |
| 2020/0390455 A1 | 12/2020 | Nguyen et al. | |
| 2020/0406018 A1* | 12/2020 | Malek | A61M 25/04 |
| 2022/0183695 A1* | 6/2022 | Julason, Jr. | A61B 17/12036 |
| 2022/0202486 A1 | 6/2022 | Morales | |
| 2022/0273322 A1* | 9/2022 | Goyal | A61F 7/12 |
| 2022/0409857 A1* | 12/2022 | Saadat | A61B 17/320758 |
| 2023/0114949 A1 | 4/2023 | Savastano et al. | |
| 2023/0233819 A1* | 7/2023 | Malek | A61M 27/006 604/8 |
| 2024/0148959 A1 | 5/2024 | Savastano et al. | |

FOREIGN PATENT DOCUMENTS

| | | |
|---|---|---|
| WO | WO-2015179324 A2 | 11/2015 |
| WO | WO-2018145212 A1 | 8/2018 |
| WO | WO-2019148094 A1 | 8/2019 |
| WO | WO-2021007346 A1 | 1/2021 |
| WO | WO-2021222157 A1 | 11/2021 |
| WO | WO-2022087369 A1 | 4/2022 |
| WO | WO-2024098065 A1 | 5/2024 |

OTHER PUBLICATIONS

Final Office Action for U.S. Appl. No. 17/976,667 dated May 24, 2023, 28 pages.

International Search Report and Written Opinion for International Application No. PCT/US2021/029276, mailed Sep. 23, 2021, 8 pages.

Invitation to Pay Additional Fees for International Application No. PCT/US2021/029276, mailed Jul. 19, 2021, 2 pages.

Kim, Wi Jin, et al. "Endovascular transmural access to carotid artery perivascular tissues: safety assessment of a novel technique." Journal of NeuroInterventional Surgery (2022): 1-8.

Mercator. Bullfrog Micro-Infusion Device Brochure. http://www.mercatormed.com/bullfrog-micro-infusion-device, Feb. 17, 2016, Accessed online Nov. 16, 2022, 3 pages.

Non-Final Office Action for U.S. Appl. No. 17/976,667 dated Mar. 10, 2023, 28 pages.

EP Application No. 21797425.2 Extended European Search Report dated Feb. 12, 2024, 8 pages.

Non-Final Office Action for U.S. Appl. No. 18/469,376 mailed on Nov. 16, 2023, 9 pages.

PCT/US2023/078841 International Search Report and Written Opinion dated Feb. 26, 2024, 15 pages.

\* cited by examiner

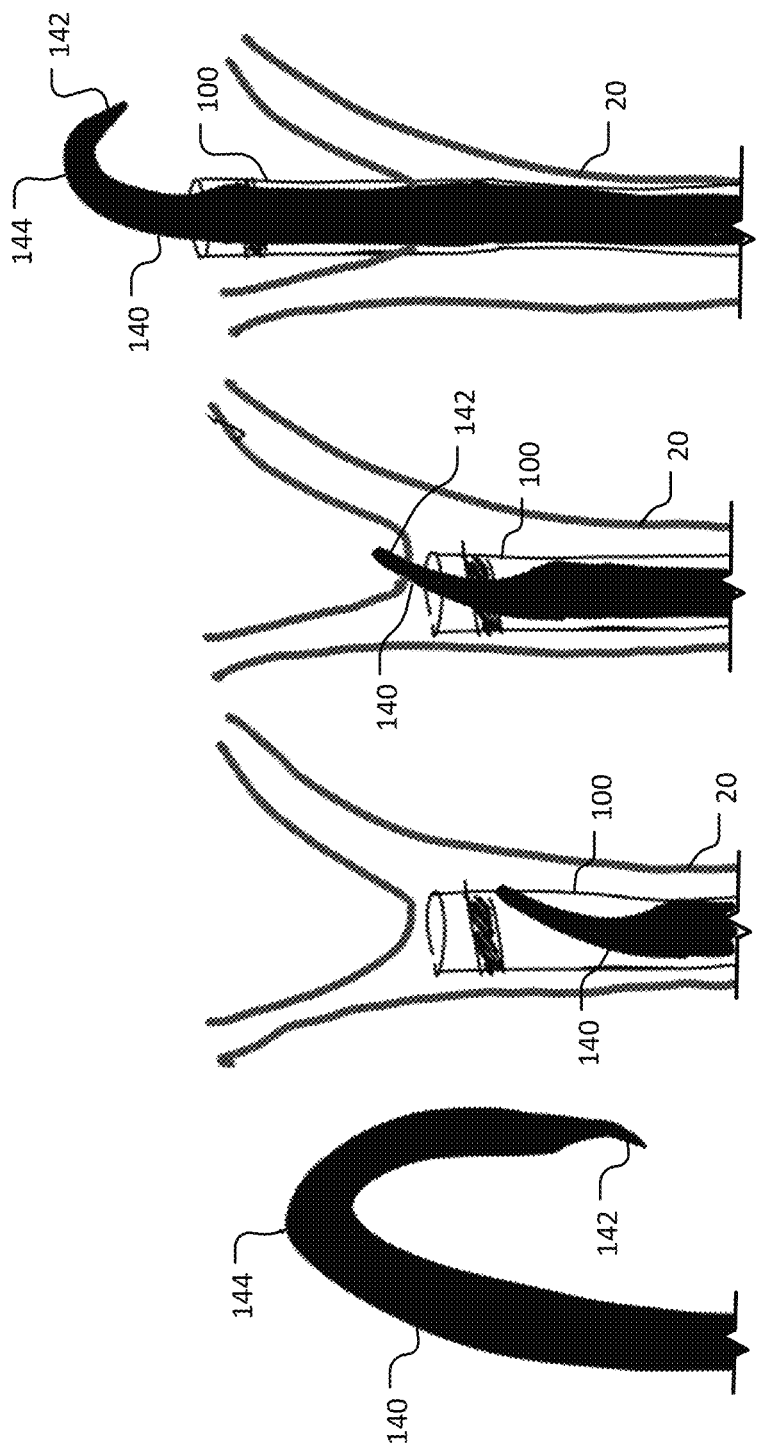

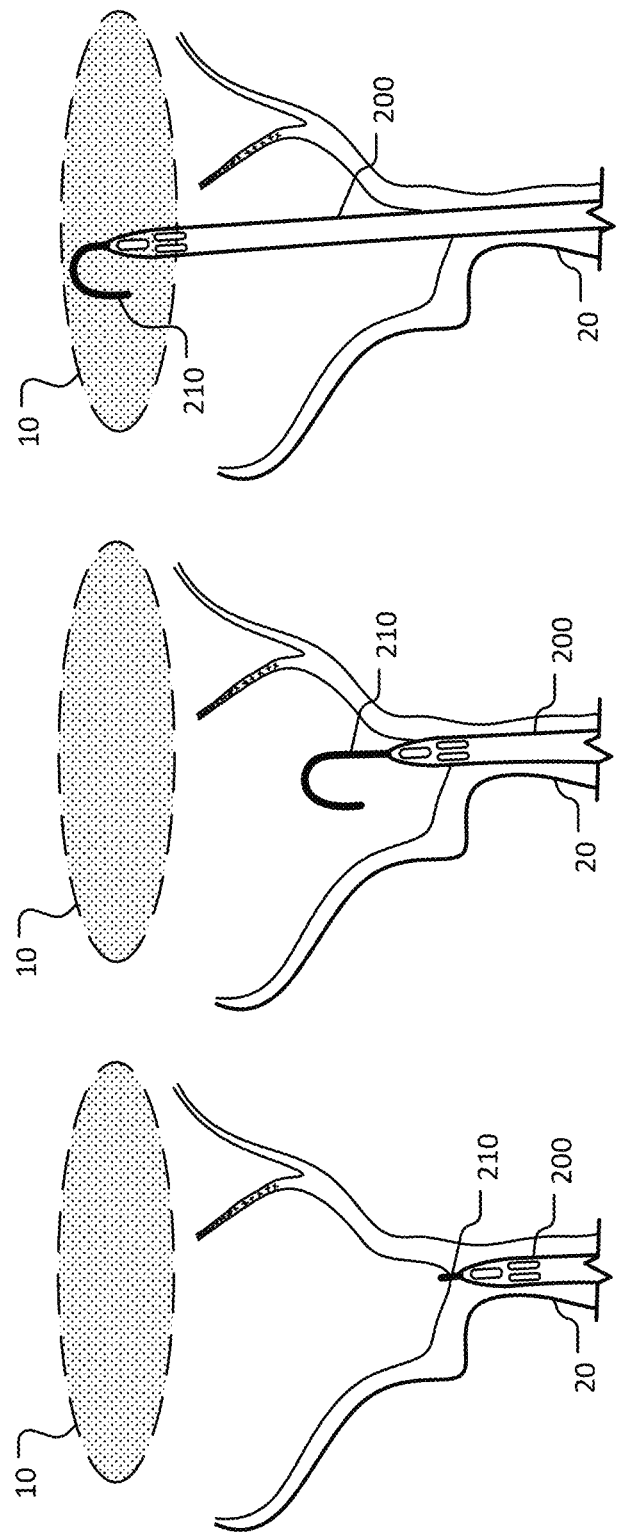

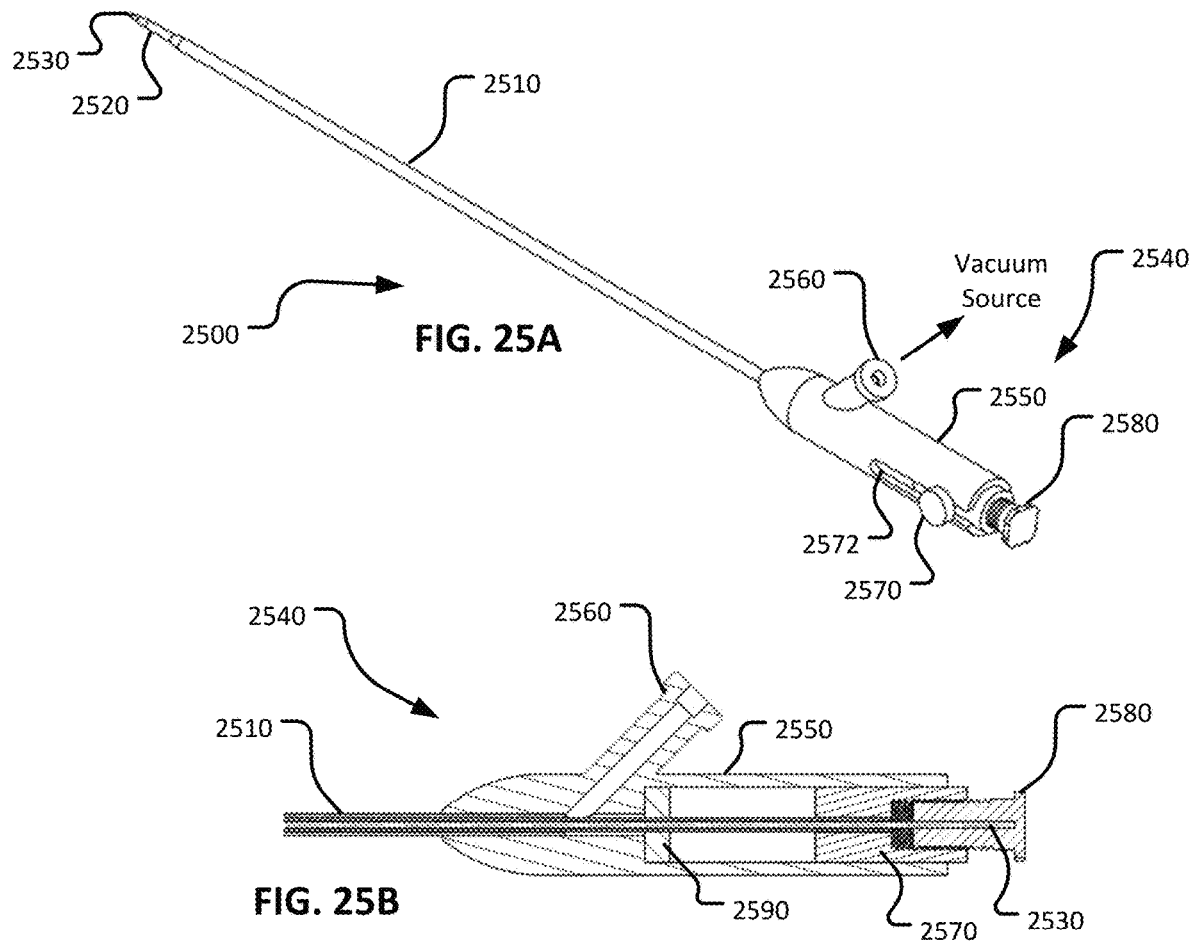
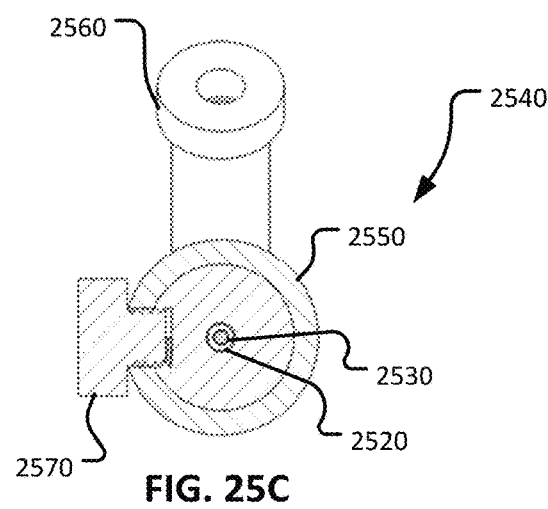

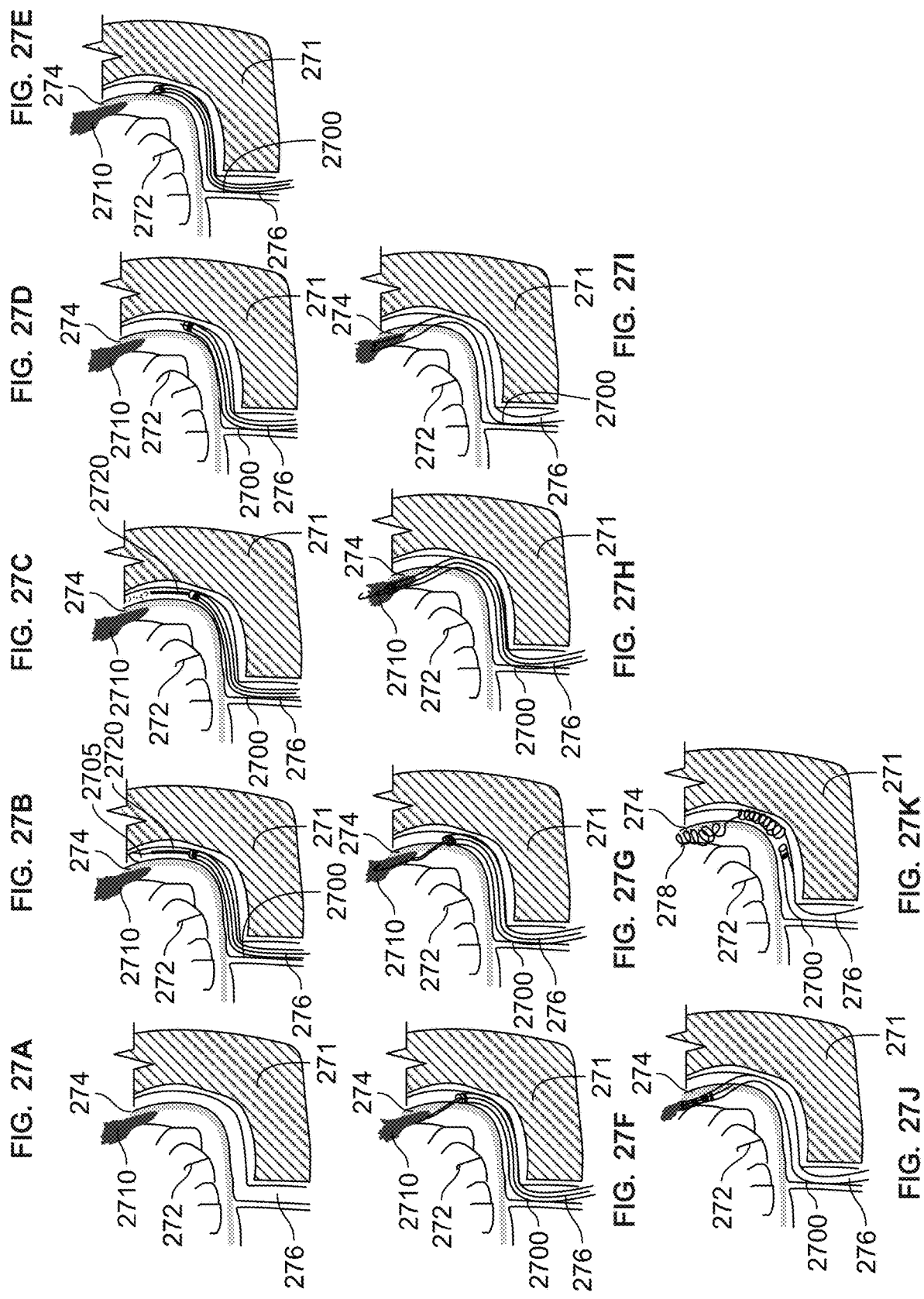

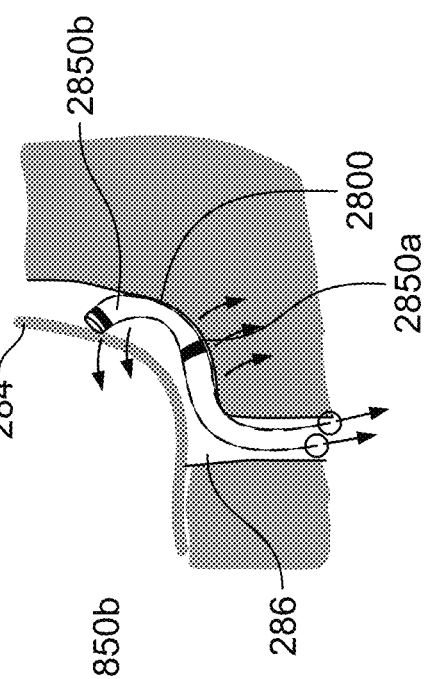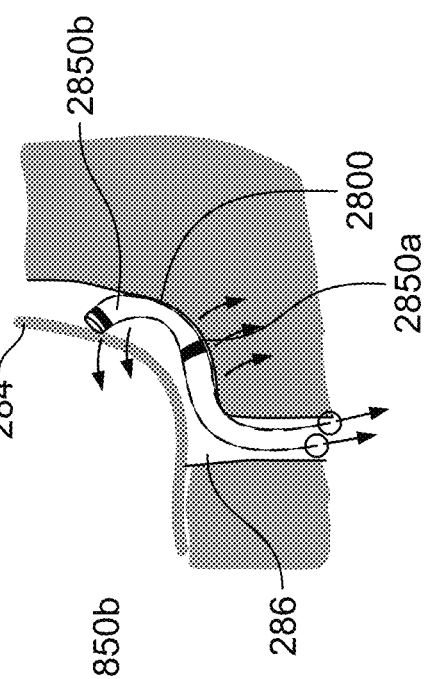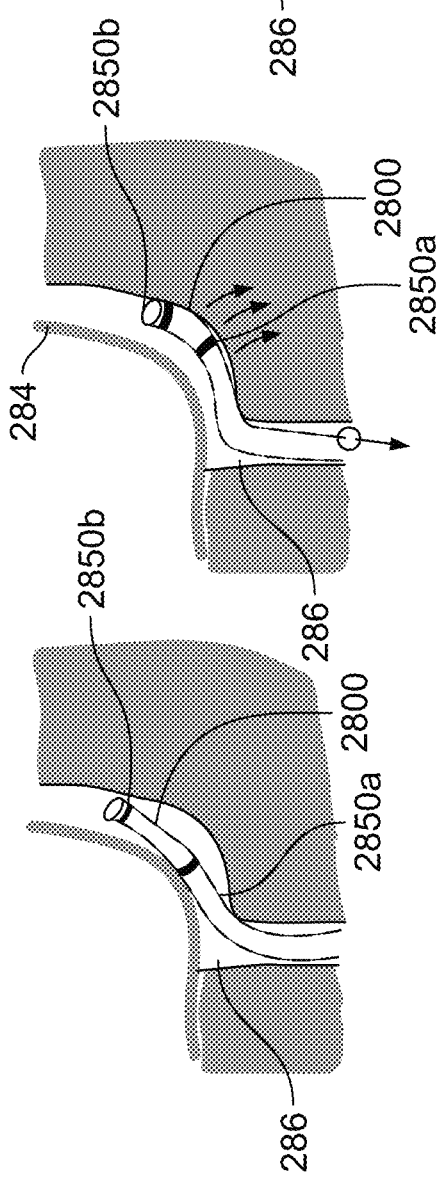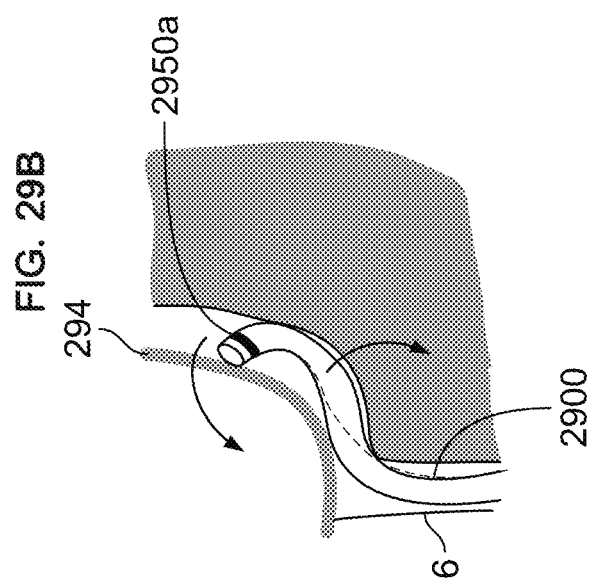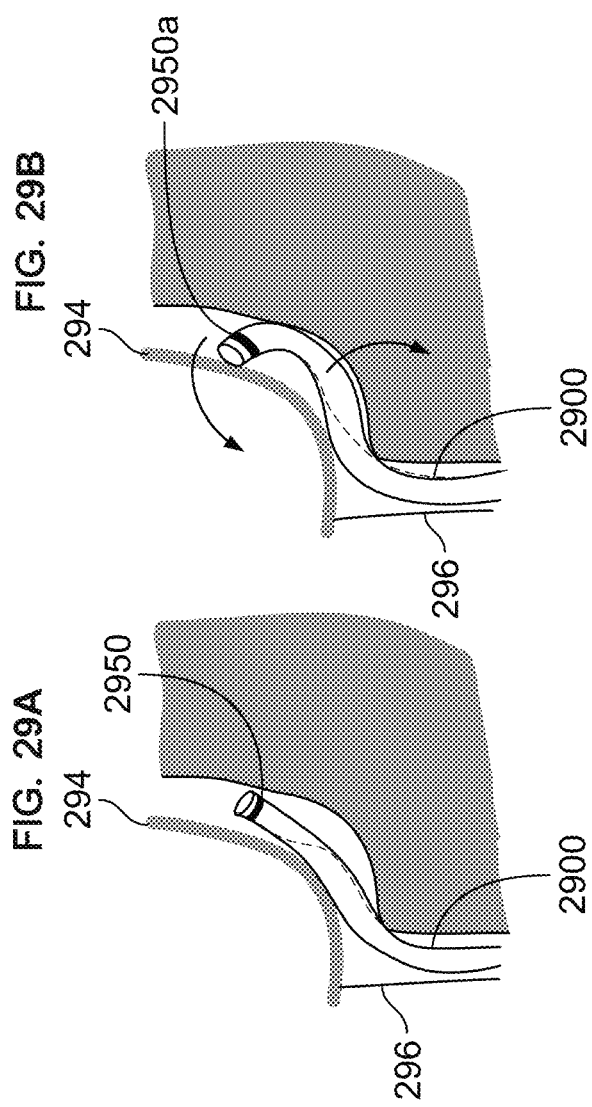

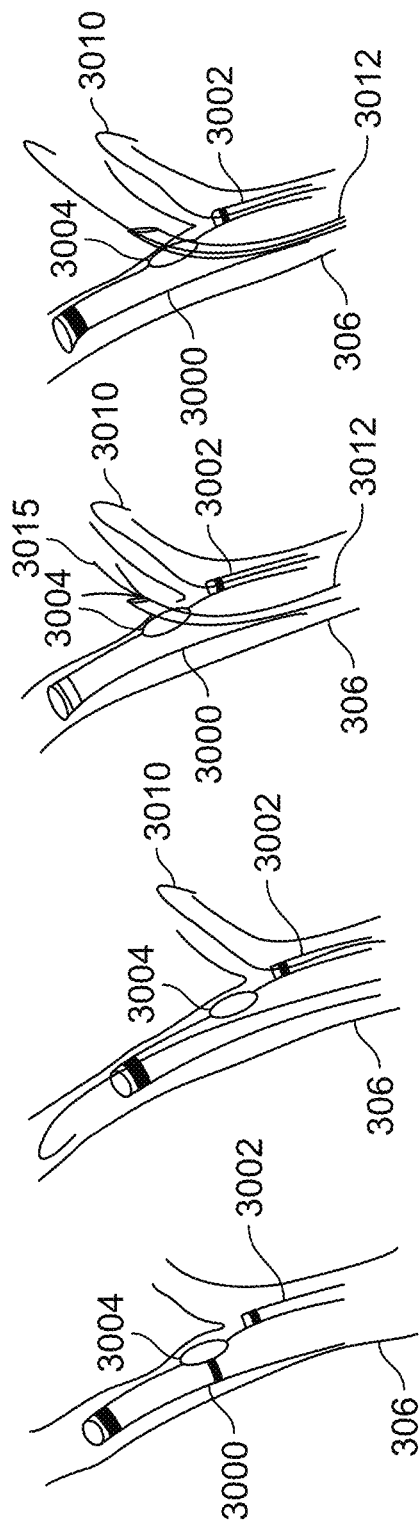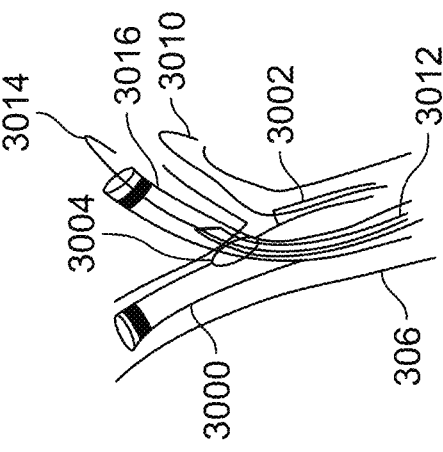

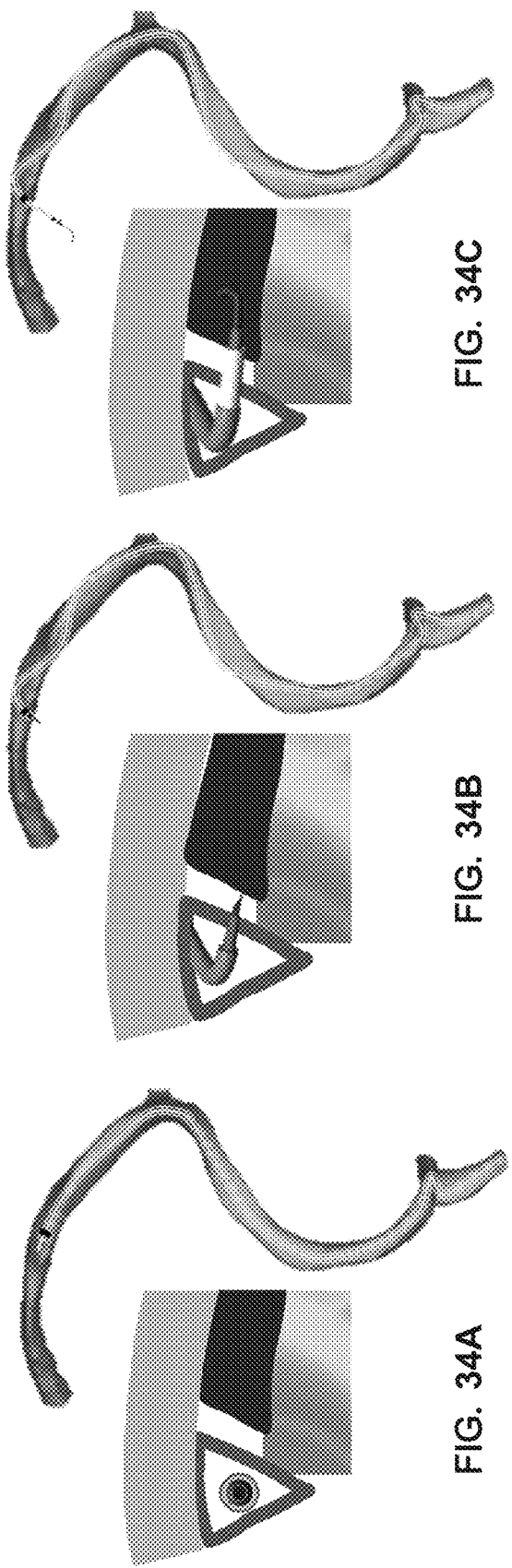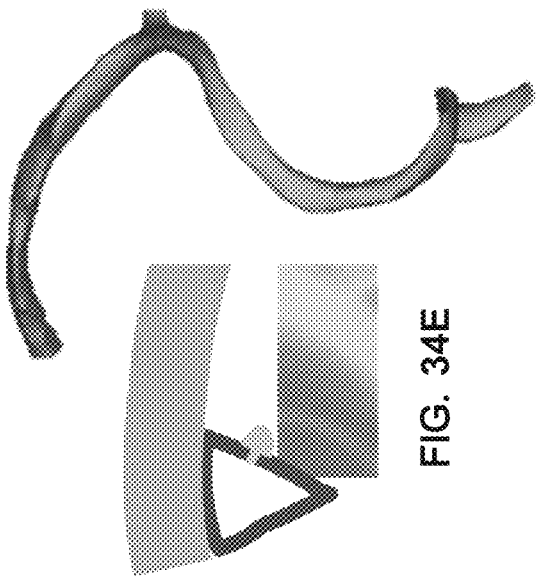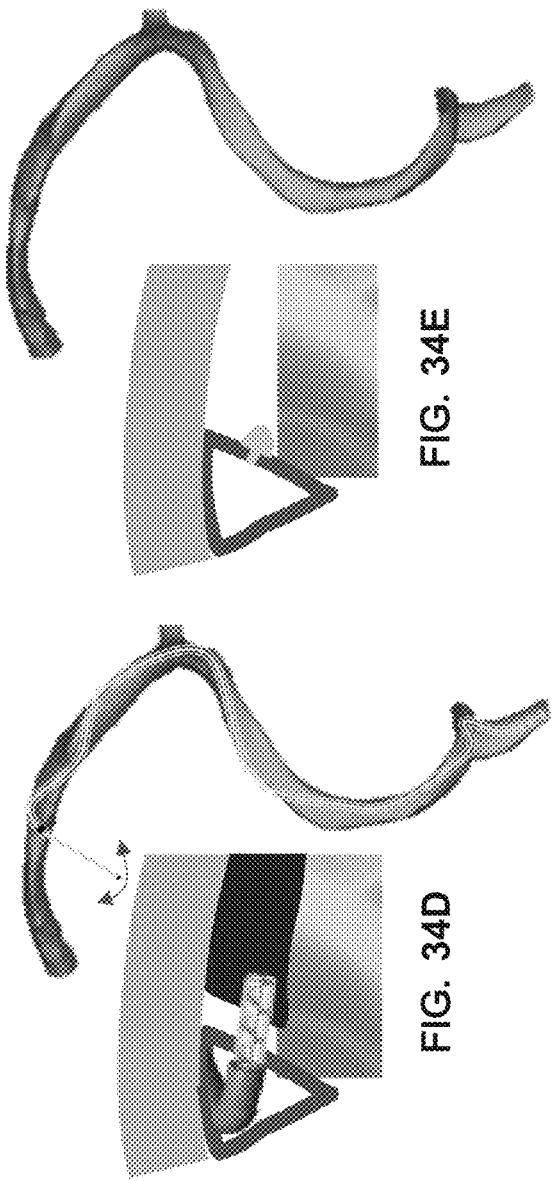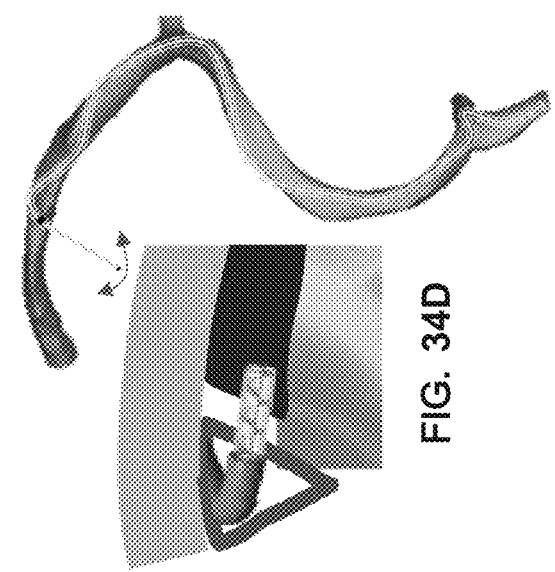

DEVICES AND METHODS FOR TRANSVASCULAR DRAINAGE OF FLUIDS IN AN INTRACRANIAL EXTRAVASCULAR SPACE

CROSS-REFERENCE TO RELATED APPLICATIONS

This application is a continuation of U.S. patent application Ser. No. 17/976,667, filed Oct. 28, 2022, which is a continuation of International Application No. PCT/US2021/029276, filed Apr. 27, 2021, which claims benefit from U.S. Patent Application No. 63/016,613, filed Apr. 28, 2020, the disclosures of each of which are incorporated by reference herein in their entirety.

TECHNICAL FIELD

This disclosure relates to devices and methods for treating intracranial hematoma and access the intradural compartment from a trans-vascular approach. For example, this disclosure relates to devices and methods for embolization of the middle meningeal artery and subdural hematoma drainage in a single endovascular intervention using multimodal catheter-based technology.

BACKGROUND

A subdural hematoma (SDH) is a collection of blood outside the brain generally resulting from head trauma and frequently associated with blood thinners. SDH complicates approximately 11% of mild to severe head injuries that require hospitalization and approximately 20% of severe traumatic brain injuries. If not surgically drained, SDH may cause an increase in the pressure inside the skull, damage the delicate brain tissue, and become life-threatening. Initially, acute SDH (aSDH) are mostly formed by stiff clots, but in the subsequent days, the clots progressively liquefy into a viscous subacute SDH (saSDH), which tends to perpetuate and expand into a chronic SDH (cSDH). The latter condition is becoming a public health problem in aging populations as it is associated with brain atrophy in elderly patients and anti-coagulation with the use of blood thinners. Annually, there are approximately 17-20 per 100000 Americans affected by cSDH. To date, cSDH remains a disabling and deadly disease, with in-hospital mortality of 16.7%, 1-year mortality of 32%, and only 21.10% of patients admitted returning home.

The standard treatment for symptomatic SDH is surgical evacuation. Generally, cSDH are relatively thin and can be drained with two burr holes, while saSDH and aSDH are formed by viscous fluid and/or clots and their evacuation utilizes large bone "windows" called craniotomies. Craniotomies are used in acute-on-chronic SDH (acSDH), which affect >10% of patients with cSDH and are formed by encapsulated liquefied hematoma mixed with solid subdural clots. Despite the effectiveness of initial surgical evacuation, it has been fraught for a failure rate of up to 37%. Even when treatment fails once and patients undergo a second surgical treatment, further recurrences are common; recurrence for cSDH can reach as high as 46%.

Surgical evacuation is commonly combined with the introduction of drains in the subdural space, which remain in place for 2-3 days. Although this strategy was reported to reduce the recurrence rate and the 6-month mortality rate by approximately 50% when compared to surgery with no drains, drains can lead to complications such as brain injury, further hemorrhage from neomembranes, infection without changing the rate of recurrence, and/or clinical outcome.

Open surgical intervention utilizes reversal or discontinuation of anticoagulation and antiplatelet medications, increasing the risk of cardiovascular perioperative risks. Craniotomies can entail general anesthesia, which can be particularly hazardous to elderly patients with other comorbidities. The morbidity and mortality rates associated with craniotomy for SDH continues to be high and has been reported to be as high as 25% and 110%, respectively.

Endovascular middle meningeal artery (MMA) embolization is an emerging endovascular procedure used to reduce postoperative recurrence. Following the injection of embolic agents, the hematoma is then slowly reabsorbed, reducing the mass effect on the brain over a period of weeks to months. A meta-analysis of MMA embolization case series reported a lower recurrence rate for cSDH after embolization compared with conventional management (2.1% vs. 27.7%, OR 087, 95% CI 0.026 to 0.292, P<0.001). MMA embolization is a promising approach for treating cSDH and preventing recurrence in high-risk patients with aSDH, saSDH, and acSDH (i.e., coagulopathy or requiring blood thinners).

Although "Two-step" management is effective (surgical evacuation for rapid brain decompression with endovascular MMA as a preoperative or postoperative adjunct), this strategy still carries all the aforementioned risks and discomfort of surgery and requires two different procedures. This is inconvenient for patients, prolongs the length of hospital stay and recovery time; thus, increasing healthcare costs. A fully endovascular procedure capable of embolizing the MMA to prevent SDH expansion and evacuate SDH to provide immediate relief of brain compression is an urgent unmet clinical need.

An integrated endovascular approach to treat chronic SDH requires concurrent MMA embolization and drainage of the fluid. Based on the teachings described herein that includes the anatomy of the MMA, the location and viscosity of cSDH, and the strength of the arterial wall of the MMA and the underlying dura, MMA embolization and trans-arterial cSDH is feasible by the devices and methods herein disclosed.

An endovascular approach to evacuate acute, subacute and acute on chronic typically SDH requires catheters with lumen larger than the ones that could accommodate the MMA. In addition, embolization of the MMA is of a lesser importance compared to cSDH. Based on the teaching here described that includes the anatomy and strength of the superior sagittal sinus, the transverse-sigmoid complex and the superior petrosal sinus, trans-venous SDH evacuation is feasible by the devices and methods herein disclosed.

The devices and methods for trans-arterial and trans-venous access to the intracranial compartment will enable delivery of therapeutics drugs and devices within the intracranial compartment.

SUMMARY

This disclosure describes devices and methods for accessing the intradural compartment and treating subdural hematomas. For example, this disclosure describes devices and methods for embolization of the middle meningeal artery and chronic subdural hematoma drainage in a single endovascular intervention using multimodal catheter-based technology.

Described herein are devices and methods to navigate intracranial venous sinuses from a peripheral approach and access the intradural compartment to evacuate subdural hematomas. Also described herein are devices and methods for transvascular access to the supratentorial intradural compartment. The intradural compartment is composed of the subdural space, the subarachnoid space with their expansions (e.g., cisterns), the brain tissue, and the brain ventricles (e.g., fluid filled cavities inside the brain). The supratentorial compartment is considered the intracranial space above the tentorium. The devices and methods disclosed herein also describe access into the epidural space from a transvascular approach.

In one aspect, this disclosure is directed to a system for drainage of intracranial extravascular fluid, thrombus or particulate matter. The system includes: (i) a suction catheter defining a first lumen and having a distal tip portion configured for insertion into a vascular channel; (ii) a shaft defining a second lumen and slidably disposable within the first lumen, a distal end portion of the shaft having a curved shape when unconstrained and being flexible so as to have a linear shape when radially constrained within the first lumen; and (iii) a stylet slidably disposable within the second lumen and having a beveled tip configured for penetration of a wall of a middle meningeal artery.

Such a system for drainage of intracranial extravascular fluid, thrombus or particulate matter may optionally include one or more of the following features. In some embodiments, the system also includes system a micro-catheter slidably disposable within the first lumen and having a distal tip portion configured for insertion into a branch vessel of the middle meningeal artery.

In another aspect, this disclosure is directed to a method for trans-arterial drainage of a subdural hematoma of a patient. The method includes: (a) advancing a suction catheter within the vasculature of the patient until a distal tip of the suction catheter is located within a middle meningeal artery of the patient, the suction catheter defining a first lumen; (b) advancing a shaft defining a second lumen and a stylet within the second lumen through the first lumen of the suction catheter; (c) advancing the stylet distally beyond outlets of the first and second lumens so that a beveled distal tip of the stylet creates a puncture through a wall of the middle meningeal artery and dura; (d) advancing the shaft over the stylet and through the puncture so that a distal tip portion of the shaft takes on a natural curved shape; (e) advancing the suction catheter through the puncture; (f) advancing the shaft with the distal tip portion having the curved shape and the suction catheter toward the subdural hematoma until an open distal end portion of the suction catheter is in the subdural hematoma; and (g) draining fluid from the subdural hematoma using the suction catheter with vacuum and possibly other thrombectomy enhancement methods. Such a method for drainage of a subdural hematoma of a patient may optionally include one or more of the following features. The method may also include: (h) advancing a micro-catheter within the first lumen until a distal tip of the micro-catheter is located within the middle meningeal artery; and (i) injecting an embolic material via the micro-catheter to occlude the middle meningeal artery, which is generally performed before arterial perforation. In some embodiments, the method may also include withdrawing the suction catheter, shaft, and stylet from extending through the puncture; and delivering a plug, coil or particles through the first lumen to block the puncture.

The devices and methods described herein provide access to the intracranial compartment enabling the permanent or temporary delivery of therapeutics and devices and performance of multiple interventions and can include features to: a) penetrate the dura to remain in the subdural space; 2) penetrate the dura to transverse the subdural space into subarachnoid space, the brain tissue and brain ventricles.

In another aspect, this disclosure is directed to a method for trans-venous drainage of a subdural hematoma of a patient. The method includes: (a) advancing a suction catheter within the vasculature of the patient until a distal tip of the suction catheter is located within an intracranial vein (like a superior cerebral vein) or dural venous sinus, the suction catheter defining a first lumen; (b) advancing a shaft defining a second lumen and a stylet within the second lumen through the first lumen of the suction catheter; (c) advancing the stylet distally beyond outlets of the first and second lumens so that a beveled distal tip of the stylet creates a puncture through a wall of the vein and/or sinus; (d) advancing the shaft over the stylet and through the puncture so that a distal tip portion of the shaft takes on a natural curved shape; (e) advancing the suction catheter through the puncture; (f) advancing the shaft with the distal tip portion having the curved shape and the suction catheter toward the subdural hematoma until an open distal end portion of the suction catheter is in the subdural hematoma; and (g) draining fluid from the subdural hematoma using the suction catheter.

Particular embodiments of the subject matter described in this document can be implemented to realize one or more of the following advantages. First, the devices and methods described herein for embolization of the middle meningeal artery provide an effective strategy to reduce chronic subdural hematoma recurrence after surgery and as primary treatment of chronic subdural hematoma, especially useful in patients in whom anticoagulation or antiplatelet therapy cannot be stopped. In the endovascular procedure described herein, the middle meningeal artery is embolized to decrease the blood supply to the "leaky" membranes; and the chronic subdural hematoma is drained, reducing the mass effect to the brain without the need of opening the skull through surgery.

Second, devices and methods described herein advantageously combine middle meningeal artery embolization and subdural hematoma drainage procedures in a single minimally invasive endovascular intervention procedure.

Third, the new techniques and apparatuses described herein circumvent open cranial surgery and all the related discomfort and complications while providing immediate brain decompression and prevention of hematoma recurrence.

Fourth, because the endovascular procedure described herein does not require reversal or discontinuation of anticoagulation, peri-operative risks and complications are decreased, leading to improved clinical outcome.

Fifth, the minimally invasive intervention described can be performed under conscious sedation (and potentially as outpatient) and with minimal discomfort, significantly shortening hospitalization time and accelerating the recovery time of patients.

Sixth, the devices and methods described herein advantageously uses the larger sizes of veins and dural venous sinuses to access the intradural compartment closer or directly on top of the SDH or with larger bore catheters. This may be needed to drain fluid with high viscosity, ingests clots, or delivery therapeutic matter and implants that would otherwise not fit through the arteries of the dura.

Seventh, the devices and methods described herein provide access to the intracranial compartment enabling the performance of multiple interventions including drainage of hematoma or other fluid collections, drug and cell delivery, implantation of electrodes or tubes, biopsies.

Unless otherwise defined, all technical and scientific terms used herein have the same meaning as commonly understood by one of ordinary skill in the art to which this invention pertains. In addition to treatment of subdural hematomas in its liquid, gel or solid form (or a combination), the methods and materials herein described can be used in the treatment of other intracranial collections such as epidural hematomas, cysts, hygromas, infection or any other fluid in any other location of the body. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Experimental findings to support embodiments are herein disclosed. Other features, objects, and advantages of the invention will be apparent from the description and drawings, and from the claims.

DESCRIPTION OF THE DRAWINGS

FIG. 10 is a schematic illustration of another example shaft that has a distal end portion with a double "J" configuration.

FIG. 11 shows the shaft of FIG. 10 in a suction catheter.

FIG. 12 shows the shaft of FIG. 10 puncturing the wall of the middle meningeal artery.

FIG. 13 shows the advancement of the suction catheter and shaft of FIG. 12.

FIG. 14 shows another example embodiment of a suction catheter and shaft.

FIGS. 15 and 16 show the advancement of the suction catheter and shaft of FIG. 14.

FIGS. 25A-25C are schematic illustrations of an embodiment of the device.

FIGS. 27A-27K are schematic illustrations of a subcomponent including an anchoring element to performate a dura, drain an SDH, and close the arteriotomy.

FIGS. 28A-28C are schematic illustrations of a catheter including two actuators for directing the distal catheter end.

FIGS. 29A and 29B are schematic illustrations of a catheter including one actuator for directing the distal catheter end.

FIGS. 30A-30E are schematic illustrations of a catheter including an aperture and a secondary catheter for annex wire anchoring.

FIGS. 34A-34E are schematic illustrations of accessing the subdural space though the wall of the SSS and draining an SDH.

Like reference numbers represent corresponding parts throughout.

DETAILED DESCRIPTION

Figure 1A:
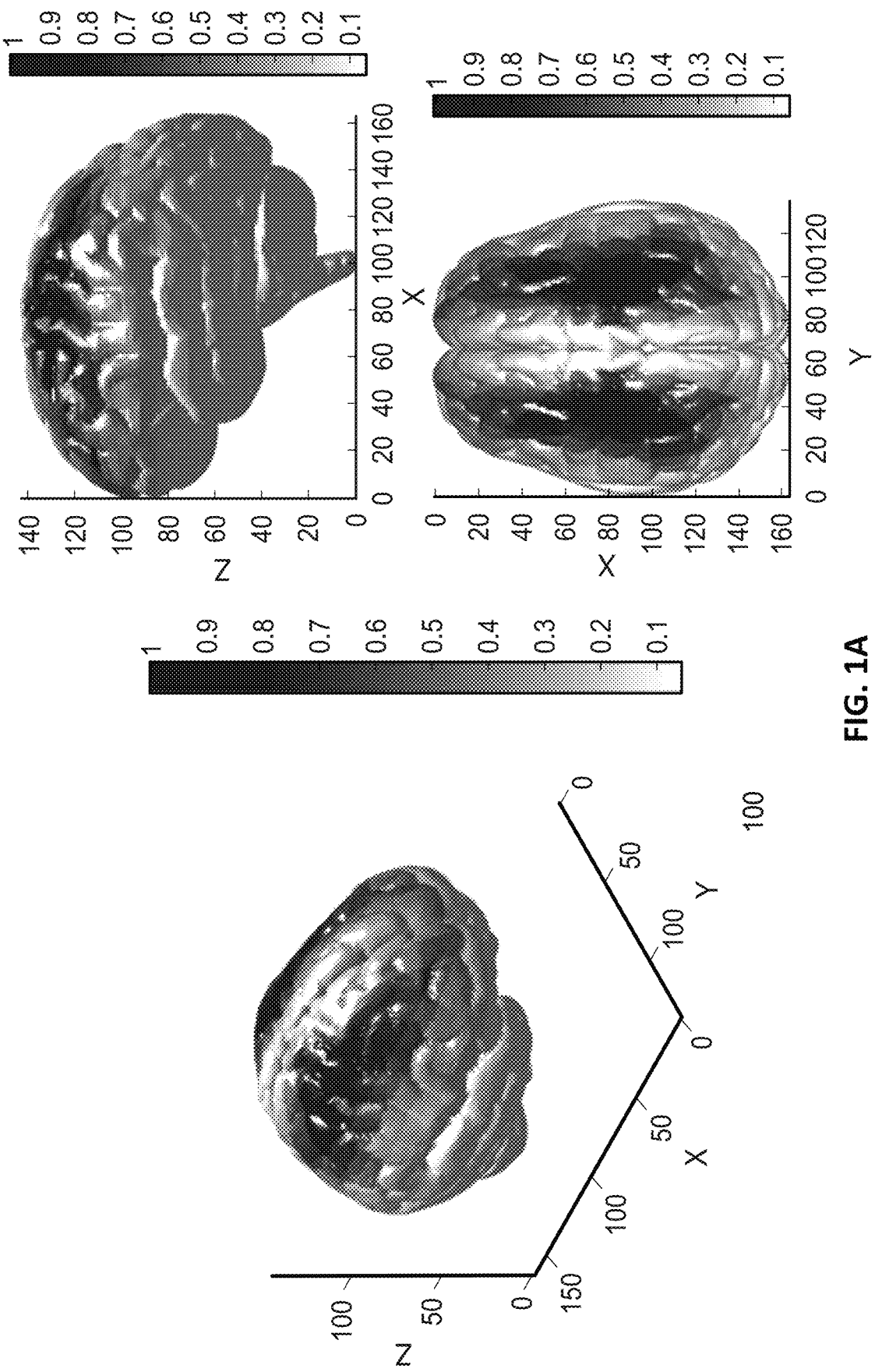
FIG. 1A are computer generated images depicting areas of a human brain in which subdural hematomas commonly occur.

The device and method here disclosed is an entirely new class of platform to enter the intradural compartment from a vascular lumen. This system would enable trans-vascular neurosurgery including drainage of SDH without opening the skull. A minimally invasive procedure offering immediate relief of brain compression and prevention of subdural hematoma re-accumulation, ideally done with a single approach and without the need of stopping anticoagulation, is an unmet clinical need. Accordingly, this disclosure describes devices and methods for treating subdural hematoma in such a fashion.

This disclosure describes devices and methods that include middle meningeal artery embolization and subdural hematoma drainage in an endovascular intervention by a catheter-based technology for trans-arterial hematoma drainage. The device navigates into the MMA from peripheral arterial access and enables the delivery of embolizing agent; provides access to the subdural space from the intra-vascular compartment; reduces blood extravasation while the passageway is patent; enables navigation within the intracranial compartment without brain perforation or damage; allows drainage of subdural collections; and facilitates arteriotomy (e.g., perforation of the arterial wall and/or dura) closure and artery occlusion upon the removal of the catheter system.

This disclosure also describes devices and methods for navigation into the dural sinuses, including the superior sagittal sinus and the superior petrosal sinus, from a peripheral venous approach and perforation into the subdural space for hematoma drainage. The device includes trans-venous use which navigates into the dural sinus from peripheral venous access; provides access to the subdural space from the intra-vascular compartment; prevents blood extravasation while the passageway is patent; enables navigation within the intracranial compartment without brain perforation or damage; allows drainage of subdural collections; facilitates durotomy closure upon the removal of the catheter system.

Referring to FIG. TA-D, a subdural hematoma (SDH) is a type of bleeding in which a collection of blood—usually associated with a traumatic brain injury—gathers between the inner layer of the dura mater and the arachnoid mater of the meninges surrounding the brain. It usually results from tears in bridging veins that cross the subdural space. Subdural hematomas may cause an increase in the pressure inside the skull, which in turn can cause compression of and damage to delicate brain tissue. SDH are located between the brain and the dura mater (e.g., the dura) and typically facing the convexity of the cerebral hemisphere and in proximity to the vascular structures of the dura, including the MMA, the superior sagittal sinus (SSS), inferior sagittal sinus (ISS), the superior petrosal sinus (SPS), the transverse-sigmoid junction or the transverse sinus (TS).

Distribution of SDH was computed by analyzing CT scans from 71 patients with each case including scan at 9 different levels: 1) axial plane: 1 cm from the vertex, top of corpus callosum, foramen of Monroe, mid-brain, 2) coronal plane: sphenoid wing, forum rotundum, $4^{th}$ ventricle, tentorial notch, and torcula. The possibilities of SDH presence at the surface of the brain on each 2D plane were then calculated and used to compute the probability of SDH presence along the peripheral of the 3D brain with spatial interpolation. The results are shown in FIG. TA which is a contour map of the probability of SDH presence at different locations of human brain in 3D isometric view (left), lateral view (top right), and superior view (bottom right). The color legend bar denotes the probability on a scale from 0 to 1 in 0.1 units. The units of the x- and z-axes is millimeters (mm).

Figure 1B:
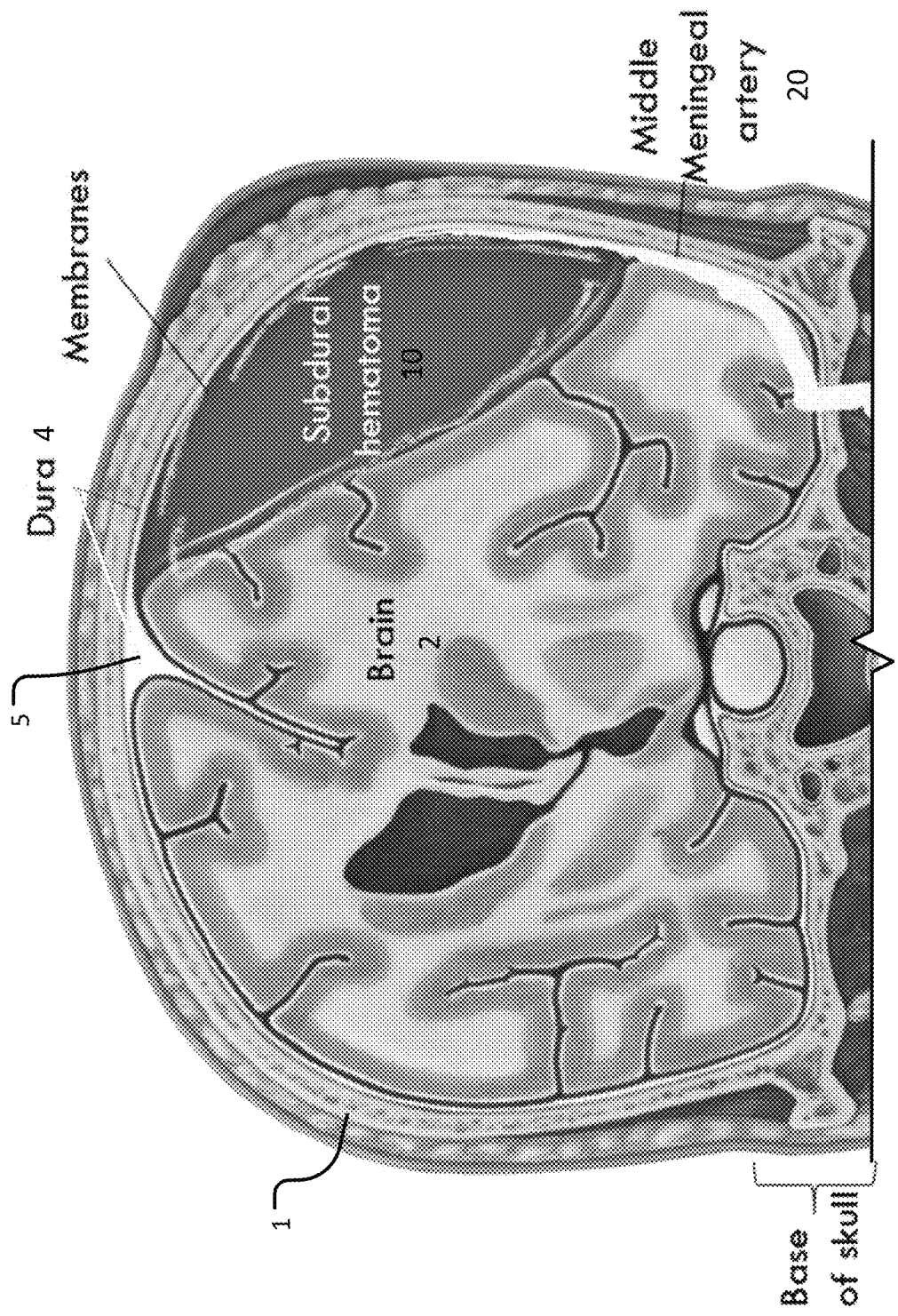
FIG. 1B shows a diagram of an example subdural hematoma.
Figure 1C:
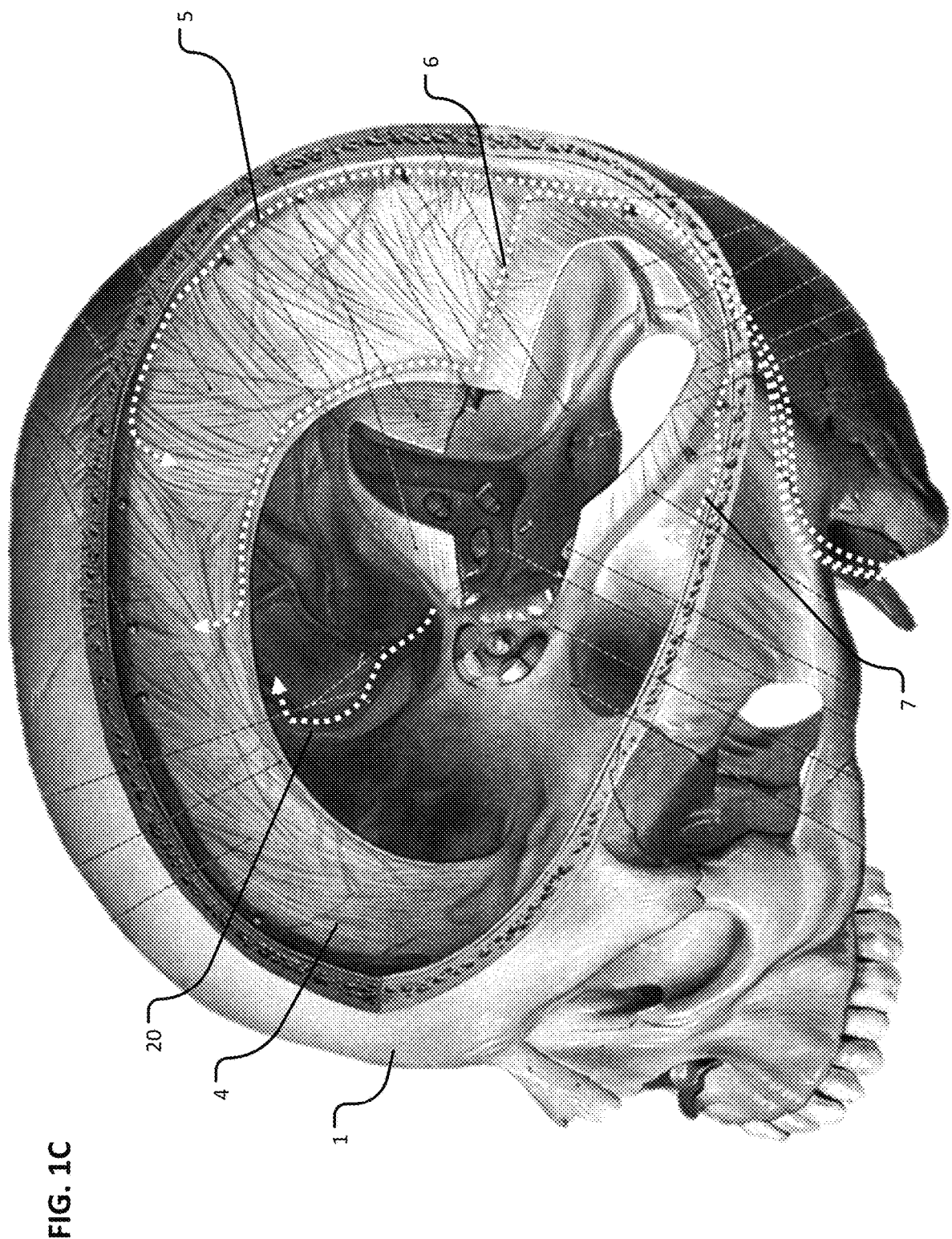
FIG. 1C is an image depicting a number of example pathways of subdural hematoma drainage.
Figure 1D:
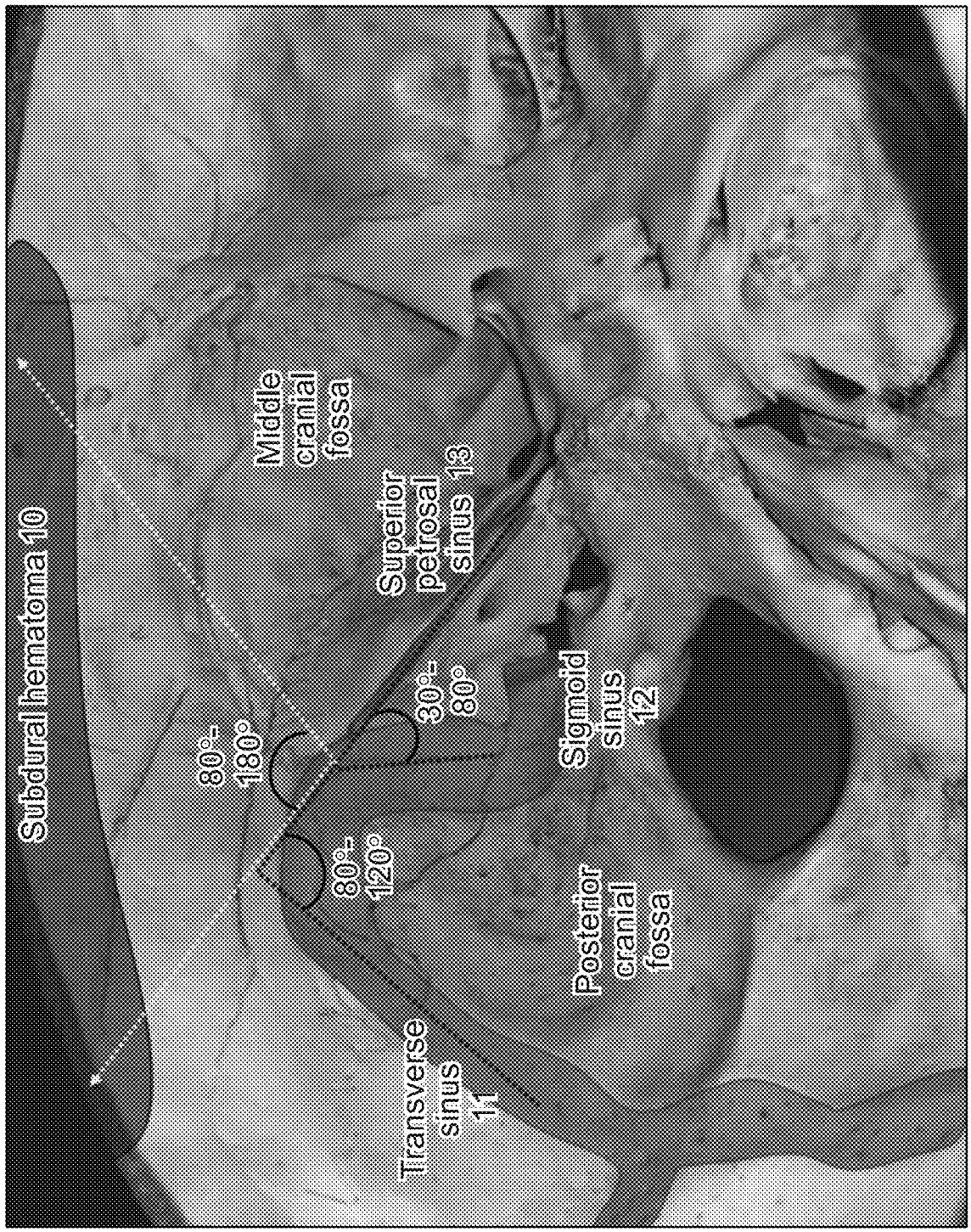
FIG. 1D is an image depicting the transverse sinus, sigmoid sinus, and superior petrosal sinus and a typical location of a subdural hematoma.

FIG. 1B-D show example access routes of the devices and methods disclosed herein to access the subdural space and drain subdural hematomas from a trans-arterial and trans-venous route.

Referring now to FIG. 1B, the MMA 20 is typically the third branch of the first portion of the maxillary artery, one of the two terminal branches of the external carotid artery. FIG. 1B is an image showing a coronal section of the head including the skull 1, brain 2, the dura 4, and with a left-sided subdural hematoma 10 and the relationship to the middle meningeal artery (MMA 20) and superior sagittal sinus (SSS 5).

FIG. 1C is an image showing a posterolateral view of the skull 1 with the vasculature of the dura 4. Dotted lines represents pathway of SDH drainage through the middle meningeal artery (MMA 20), the superior sagittal sinus (SSS 5), the inferior sagittal sinus (IPS 6), the superior petrosal sinus (SPS 7).

There is one MMA 20 in each side of the head. After branching off the maxillary artery in the infratemporal fossa, it runs through a bony canal called foramen spinosum to enter the intracranial compartment which can measure 0.3 cm to 2.8 cm. Upon entering the intracranial compartment, the MMA 20 is deflected anteriorly and laterally at an angle of 60 to 120 degrees from the longitudinal axis of the foramen spinosum and runs on the epidural side of the dura 4 (between the dura 4 and the skull 1).

The artery runs in a bony groove of the internal surface of the calvaria which typically surrounds the artery in <180 degrees of its circumference. The main trunk of the MMA 20 measures 24 mm±10 mm, and then bifurcates into a frontal and a parietal branch. Other minor branches are present. The mean diameter of the main trunk of the MMA 20s is 0.9 mm±0.3 mm, but it is generally larger in cases of cSDH with a mean diameter of the 1.48 mm±0.48 mm.

The SSS 5 is a midline vein without valves that courses along the falx cerebri from the vicinity of the crista galli to the confluence of sinuses at the posterior cranium. The superior sagittal sinus faces both cerebral hemispheres for a typical length of 31 cm to 38 cm, and receives 12 to 20 venous tributaries from each side (left and right cerebral hemispheres). The sinus has a triangular shape with a typical width of 3 mm to 18 mm and a height of 3 mm to 14 mm. The typical cross-sectional area of the SSS 5 ranges 15 mm$^2$ to 90 mm$^2$, and the angle between the sinus wall and a midline typically ranges 25° to 65°. The structural analysis of the SSS 5 and subdural space (SDS) in non-contrasted head CTs of 100 patients undergoing surgical evacuation of SDH 10 showed that the SSS 5 has a typical width of 9.6 mm (SD 2.4), atypical height of 5.6 mm (SD 1.6), and a typical area of 34.5 mm$^2$ (SD 13.8). The minimal width of the parasagittal subdural space (i.e., between the SSS 5 medially and the SDH 10 laterally) was 5.3 mm (SD 3.3), and the distance between the SSS 5 and the SDH 10 via the subdural space was 19.8 mm (SD 14.1).

Typically, the sinus is larger closer to the confluence of the sinuses on the back of the head. At the confluence of the sinuses, the lumen of the SSS 5 continues into the transverse and sigmoid sinus, and then drains into the jugular vein. The SSS 5 is surrounded by dura 4 mater and separated from the brain by the arachnoid and subarachnoid space filled with cerebrospinal fluid. In elderly patients the brain undergoes atrophy resulting in widened spaces between the sinus and the brain. In a cohort of 90 patients with chronic SDH 10, we found that the space between the surface of the brain and the dura 4 covering the skull 1 in a parasagittal location is 1 mm to 20 mm, typically 2 mm to 8 mm. The distance between the SSS 5 wall and the SDH 10 ranged between 0 mm and 60 mm, with >90% of the patients within 40 mm, and >75% of patients within 20 mm.

FIG. 1D is an image showing an oblique view of the left middle and posterior cranial fossa. The transverse sinus 11, the sigmoid sinus 12, and the superior petrosal sinus 13 are highlighted along with the typical location of the subdural hematoma 10 is highlighted in red. The angles between each sinus, 11, 12, and 13 are marked with black dotted lines. The angles of the trajectory for transvascular perforation from the junction of the three sinuses, 11, 12, and 13, is marked in gray dotted arrows.

The superior petrosal sinus (SPS 13) is part of the dural venous system that typically receives blood from the cavernous sinus and superior petrosal venous complex and drains into the transverse sinus 11. The SPS 13 connects with both the cavernous sinus and transverse-sigmoid junction in 60% of cases, only laterally with the transverse-sigmoid junction without connecting with the cavernous in 37%, and only the cavernous sinus without connecting with the transverse-sigmoid junction in 3%. In addition, the SPS 13 is a bilateral structure. Therefore, in 97% of cases it is possible to access the SPS 13 though a transjugular approach (the transverse sinus 11 drains into the sigmoid sinus 12, which in turn continues and jugular bulb and then internal jugular vein and the skull 1 base). The sinus runs in a groove in the temporal bone called superior petrosal sulcus, and the tentorium cerebelli is attached to the edges of the SPS 13. The connection of the SPS 13 to the transverse sinus 11 or transverse-sigmoid junction occurs in the most posterior and lateral part of the superior petrosal sulcus, and it is an anatomically strategic point for perforation (from the proximal SPS 13, transverse sinus 11 or transverse sigmoid junction) into the subdural space to reach the cerebral convexities. The angle between the SPS 13 and the transverse sinus 11 is generally 80 degrees to 120 degree in an axial plane. The angle between the SPS 13 and the sigmoid sinus 12 is typically 30 to 80 degrees. The SPS sinus is typically 1 mm to 5 mm in diameter. Most of SDH 10 over the cerebral convexity will be accessed if the transvascular perforation and subdural space navigation is done at an angle of 80 degrees to 180 degrees from the longitudinal main axis of the SPS 13.

Referring to FIGS. 19-22, needle penetration tests were performed and the results displayed in box-and-whisker plots with penetration force on the y-axes and sample identification on the x-axes. The median value is the central line, the box encompasses the first and third quartiles, and dotted lines extend to the minimum, and maximum values respectively.

The needle penetration tests were performed through the wall of the MMA 20 and dura 4 was conducted with a stainless-steel beveled needle (distal bevel 21 degrees, proximal bevel 14 degrees) with an outer diameter of 0.014" and with an angle of attack of 10-15 degrees. For example, a 20G needle with a 1¼" length manufactured by Jelco such as an IV Catheter Radio-opaque, REF 4056, MOD11.

Figure 19:
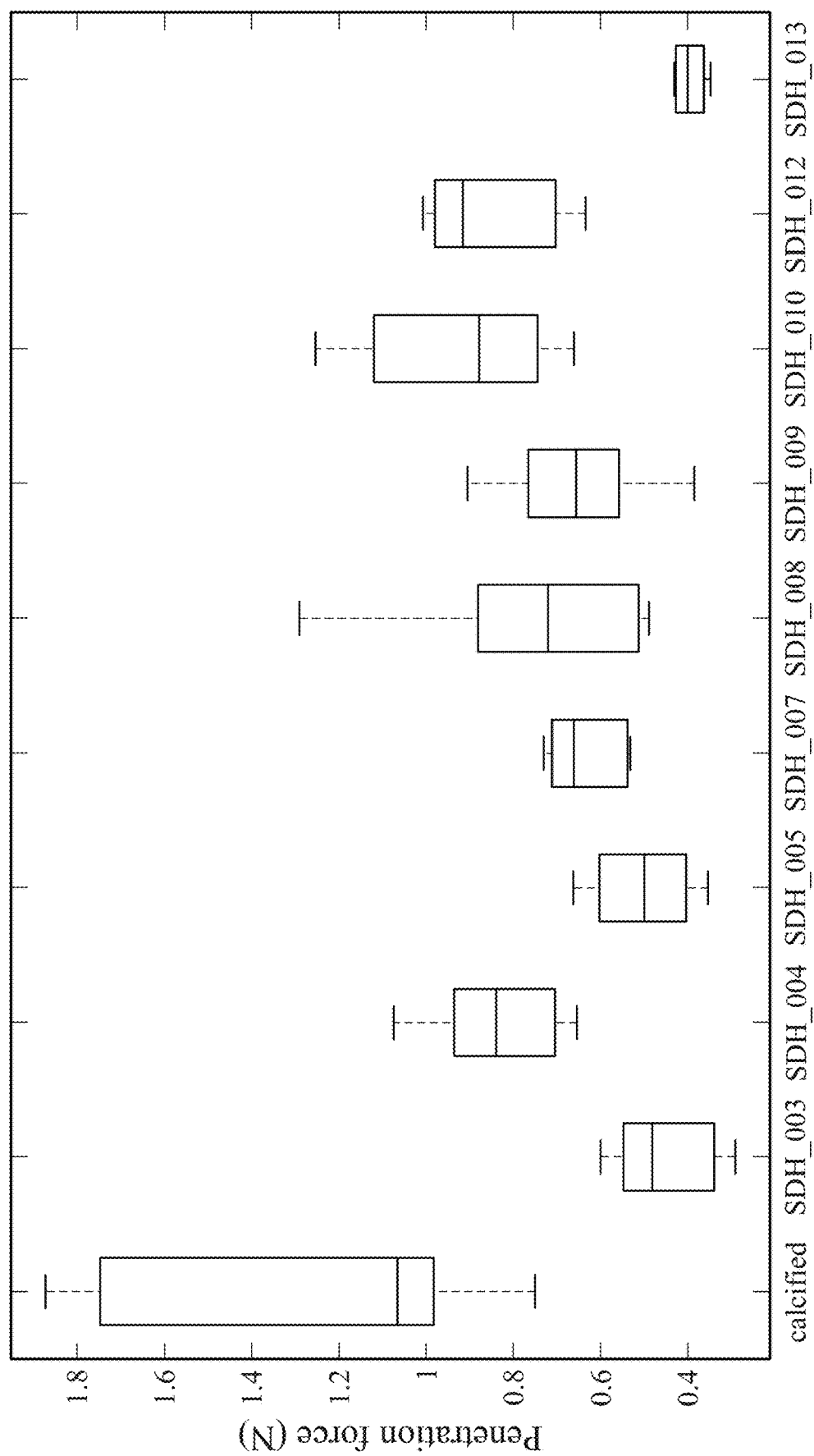
FIG. 19 is a box plot the cutting force to penetrate the MMA and the dura of the middle cranial fossa with a needle.

FIG. 19 represents the cutting force to penetrate the MMA and the dura of the middle cranial fossa with a needle.

Figure 20:
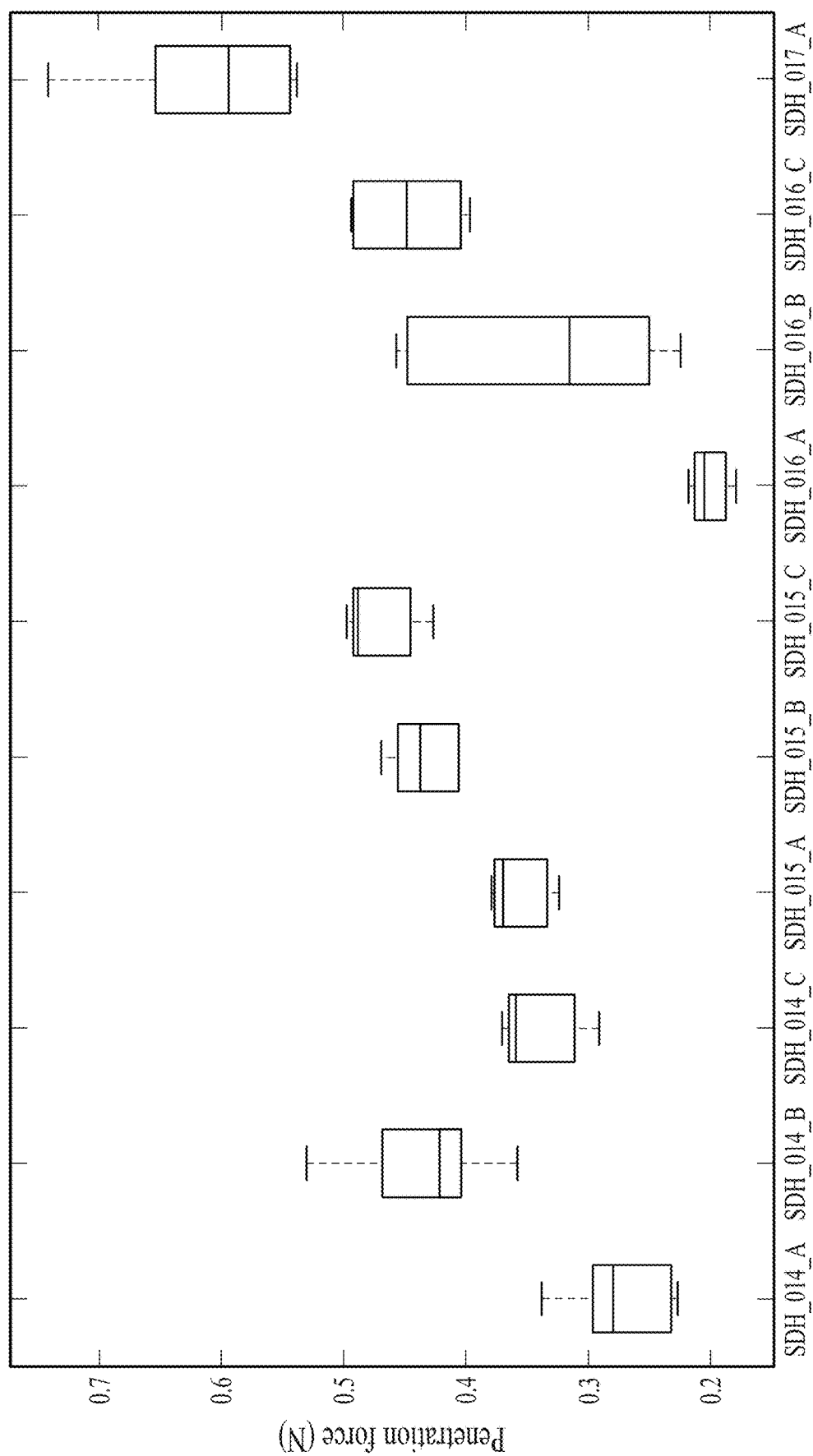
FIG. 20 is a box plot representing the cutting force to penetrate the MMA and the dura underlaying the frontal and parietal bones (i.e., convexity) with a needle.

FIG. 20 represents the cutting force to penetrate the MMA and the dura underlaying the frontal and parietal bones (i.e., convexity) with a needle.

Figure 21:
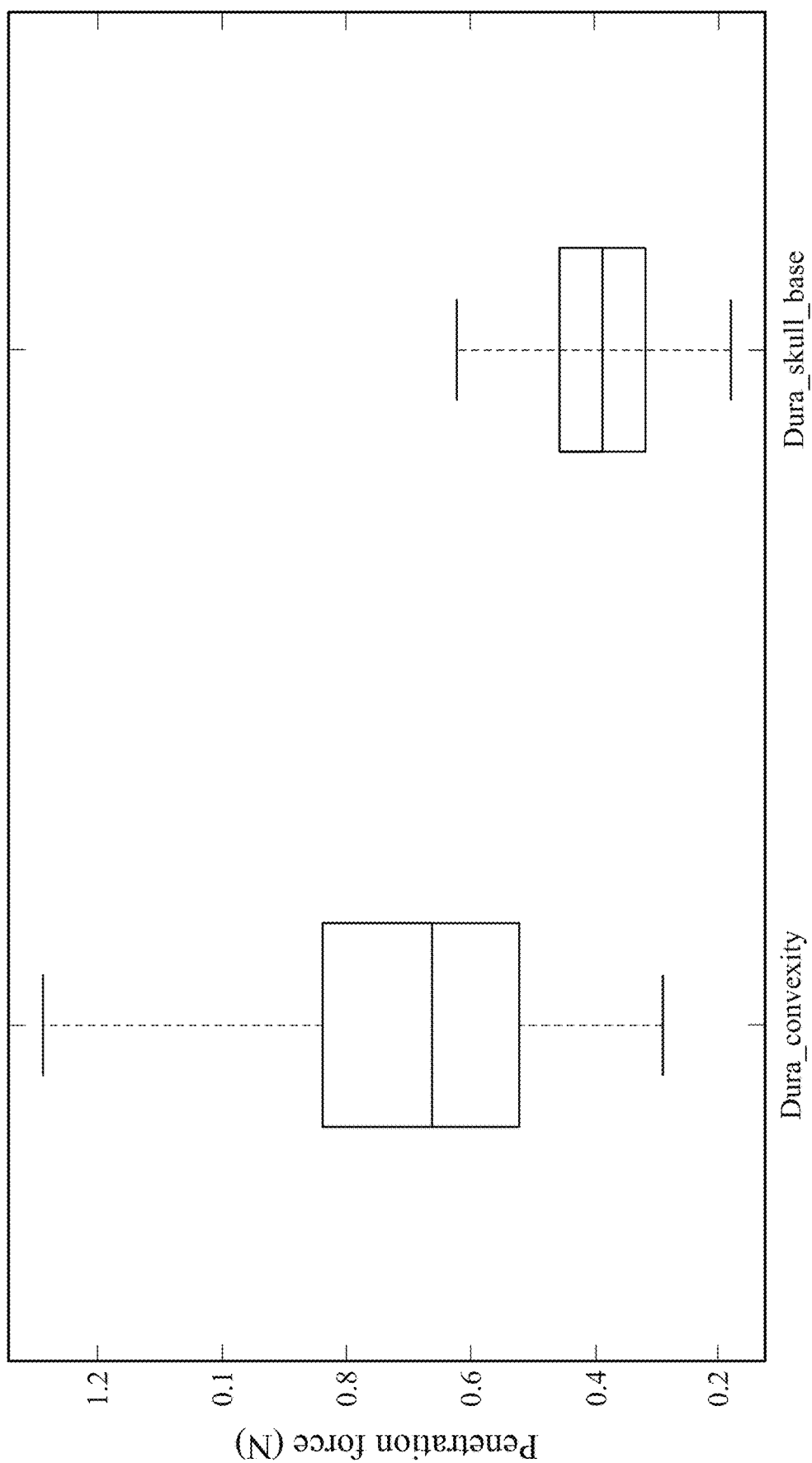
FIG. 21 is a box plot representing the cutting force to penetrate the MMA and the dura of the frontal and parietal regions (convexity) vs the middle cranial fossa (skull base) with a needle.

FIG. 21 represents the cutting force to penetrate the MMA and the dura of the frontal and parietal regions (convexity) vs the middle cranial fossa (skull base) with a needle.

Figure 22:
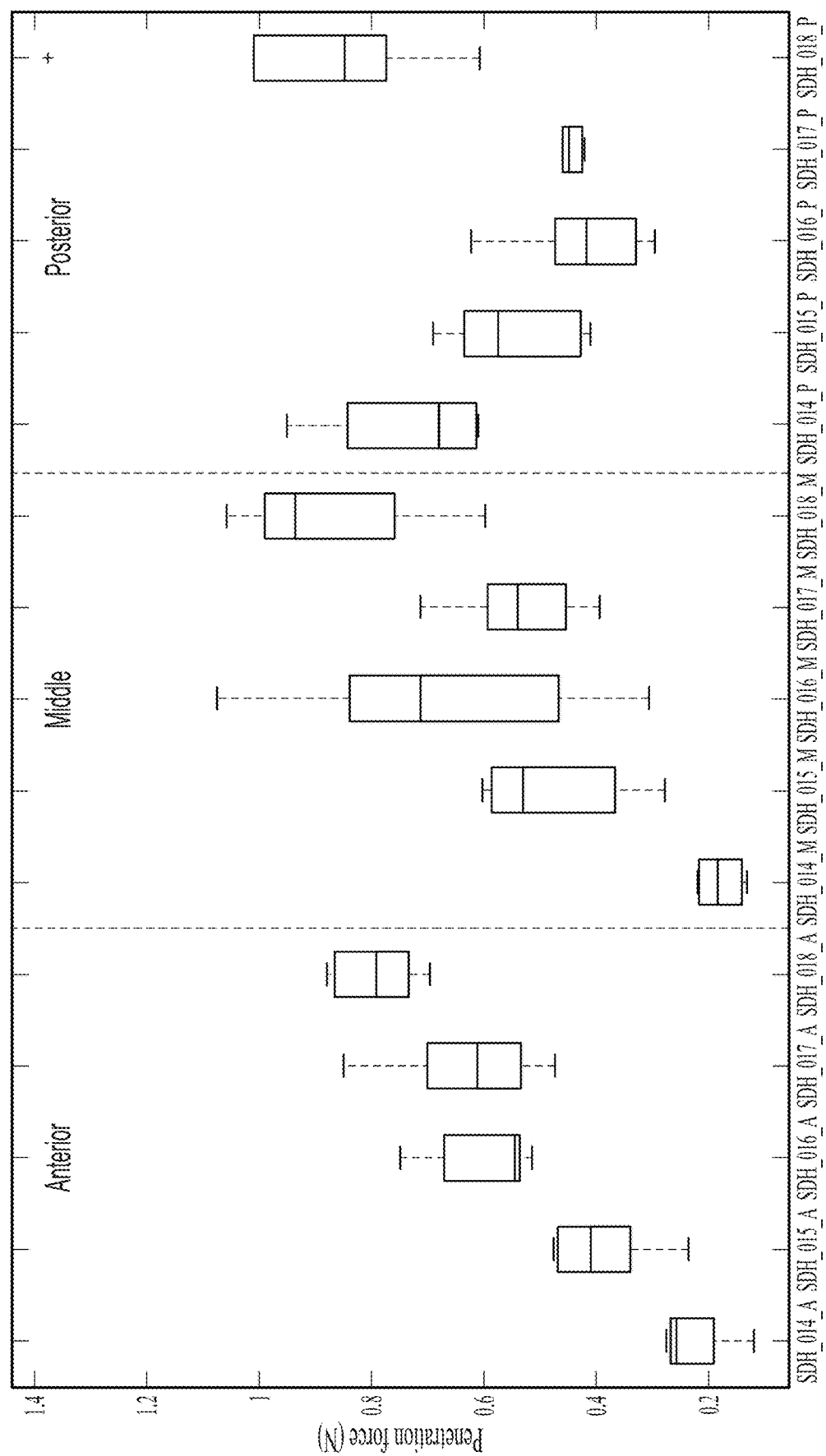
FIG. 22 is a box plot representing the cutting force to penetrate the lateral wall of the anterior, middle and posterior third of the superior sagittal sinus with needle.

FIG. 22 represents the cutting force to penetrate the lateral wall of the anterior, middle and posterior third of the superior sagittal sinus with needle.

As shown in FIGS. 19-22, the required cutting forces to penetrate from the arterial lumen to the subdural space are as follows: 1) MMA 20/dura 4 overall: 0.75 N (standard deviation (SD) 0.33N); 2): MMA 20/Non-calcified dura 4: 0.68 N(SD 0.24N); 3) MMA 20/Calcified dura 4: 1.29 N(SD 0.48N). The MMA 20/dura 4 of the middle cranial fossa required a cutting force of 0.39N (SD 0.12N).

Penetration of MMA 20 wall and non-calcified dura 4 with same needle and an outer beveled shaft (distal bevel 23 degrees, proximal bevel 9 degrees) with an outer diameter of 0.028" required a cutting force of 1.8 N to 2.2 N. Penetration of MMA 20 wall and non-calcified dura 4 with same needle and an outer shaft as above and a non-tapered catheter with an outer diameter of 0.045" required a cutting force of 2 N to 8 N. Penetration of MMA 20 wall and non-calcified dura 4 with same needle and an outer shaft as above and a tapered catheter (inner diameter at the taper of 032" to final outer diameter of 0.045") required a cutting force of 1.5 N to 2.5 N.

Needle penetration test (with the needle of 20G 1¼" Jelco IV Catheter Radio-opaque, REF 4056, MOD11) through the wall of the SSS (including dura 4) with an angle of attack of 10-15 degrees required the following cutting forces: 1) SSS overall: 0.57 N(SD 0.25N); 2) anterior third of the sinus: 0.53 N(SD 0.22N); middle third of the sinus: 0.56 N(SD 0.28N); 3) posterior third of the sinus: 0.61 N(SD 0.24N). Using a tri-axial telescoping perforating system formed by a needle (0.042") mounted on a trocar (OD 0.083") and a catheter (ID 0.088"/OD 0.106"), 6N of force was required to perforate though the SSS into the subdural space.

Figure 23:
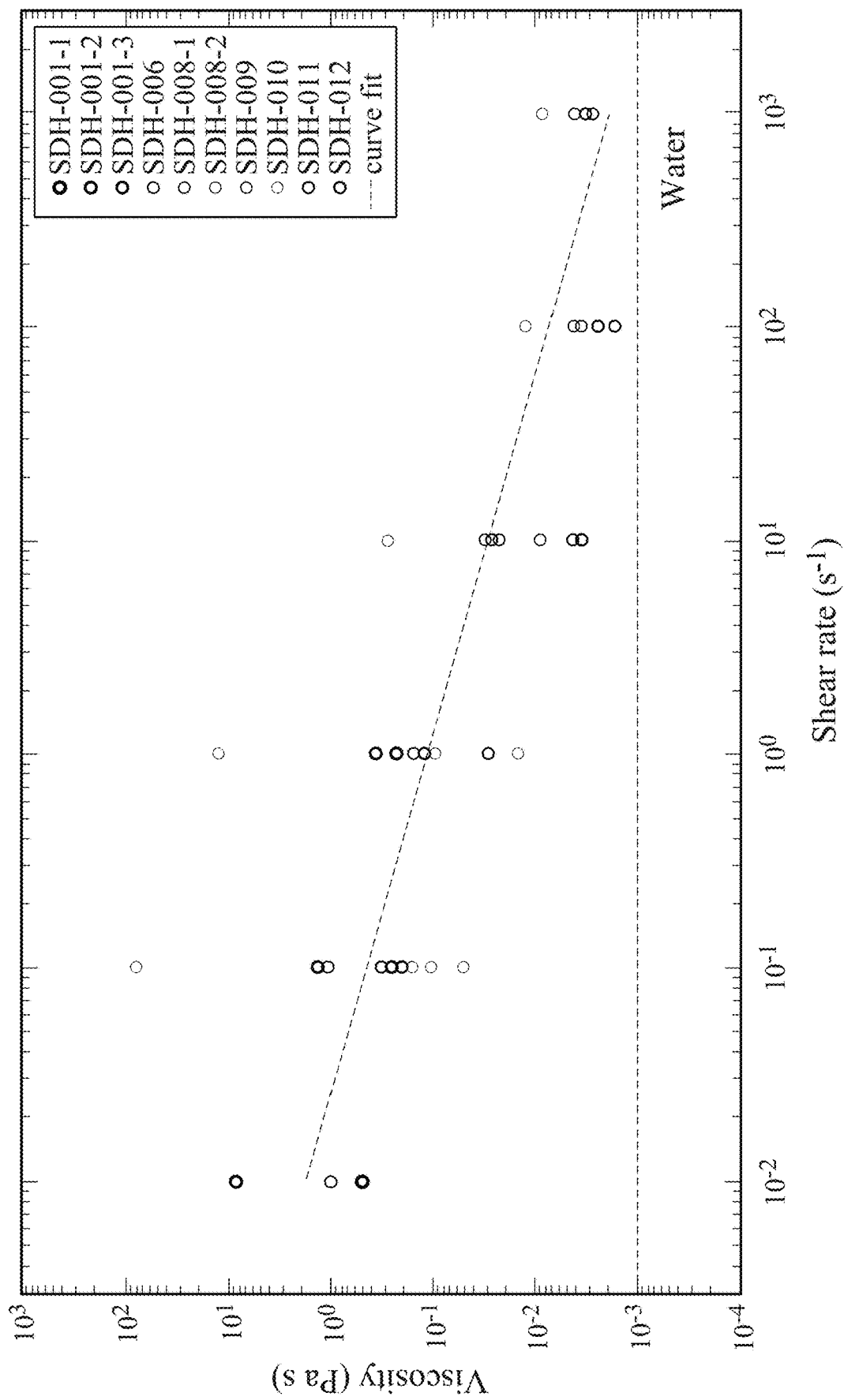
FIG. 23 is a logarithmic line chart comparing viscosity and shear rate for multiple samples of chronic subdural hematomas from different patients.

Referring to FIG. 23, ten cSDH were collected during evacuation surgery in ten patients and were tested on a rheometer (DHR-1 Hybrid, TA Instruments) to evaluate the viscosity under different shear rates (e.g., $\gamma$=10hu −2, $10^{-1}$, 1, 10, 100, and 1000 $s^{-1}$) at 37° C.

FIG. 23 is a logarithmic line chart with viscosity on the y-axis in Pa·s, and shear rate in $s^{-1}$ on the x-axis. A sample key is inset in the upper right and a curve fit is shown as a dashed line having a negative slope and the viscosity of water is shown as a horizontal dashed line at $10^{-3}$ Pa·s (labeled "water").

A non-Newtonian shear-thinning behavior was observed. A power-law was used to estimate (e.g., fit) the viscosity as $\mu = K\dot{\gamma}^{n-1}$, where $\mu$ is the viscosity, $\dot{\gamma}$ is the shear rate, and K and n are material constants and equal to 0.113 Pa·s and 0.410, respectively. The fit is shown as the dashed line correlated with the sample points.

Figure 24:
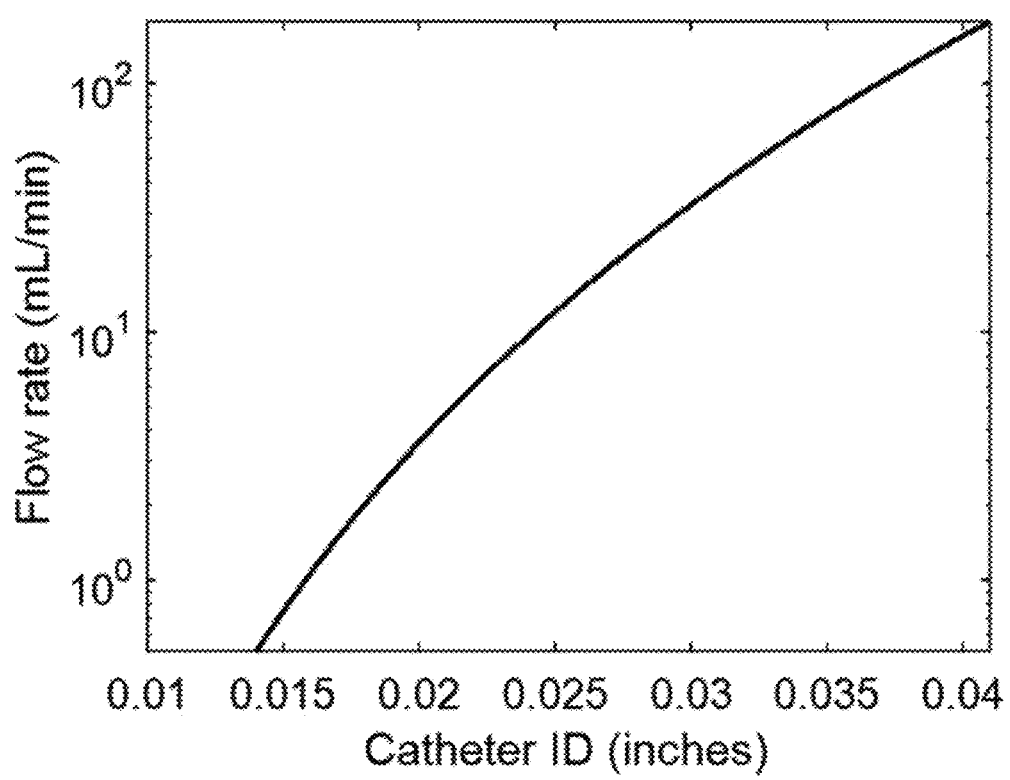
FIG. 24 is a line chart comparing logarithmic flow rate of chronic subdural hematoma fluid to catheter ID.

Referring to FIG. 24, for non-Newtonia fluid going through a tube under a pressure gradient, the flow rate Q is calculated by $$Q = \frac{\pi D^3}{8/n + 24}\left(\frac{\Delta PD}{4LK}\right)^{1/n},$$

where D is the catheter ID, ΔP is the pressure difference between the arterial pressure at the catheter distal end and the vacuum pressure at the promixal end, L is the catheter length. FIG. 24 is a line chart comparing logarithmic flow rate in mL/min on the y-axis to catheter ID in inches along the x-axis. The aspirational flow rate of SDH fluid is shown as a curved line as a function of catheter ID, assuming −45 kPa vacuum pressure is generated by manual pull of a syringe and the catheter is 1.4 m in length.

From the equation, the flow rate is in proportion to $D^{5.44}$, therefore, the ID should be selected as large as possible while maintaining catheter access to the MMA 20. A catheter with 0.027" ID can generate an aspirational flow rate of 18 mL/min. We found that cSDH can be aspirated at a clinically relevant rate by a syringe though a 150 cm long catheter with an ID 0.027". Catheters with 0.027" ID can be navigated into the MMA 20.

Figure 2:
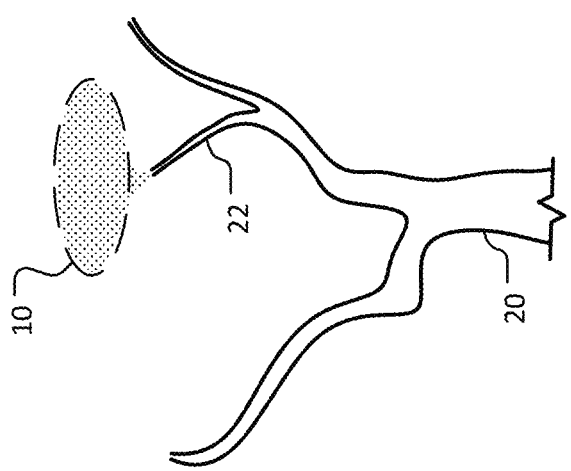
FIG. 2 is a schematic illustration of a subdural hematoma being formed from a bleeding branch vessel of the middle meningeal artery.

FIG. 2 is a schematic illustration of a subdural hematoma 10 being formed from a bleeding membrane and/or branch vessel 22 of the middle meningeal artery 20. After branching off the maxillary artery in the infratemporal fossa, it runs through the foramen spinosum to supply the dura 4, the outer meningeal layer, and the calvaria. In cases of cSDH, the MMA 20 also supplies blood to pathological membranes responsible to expand and perpetuate the collection.

In order to identify bleeding vessels such as the bleeding branch vessel 22, an imaging procedure can be performed. For example, in some embodiments an x-ray (fluoroscopy) and/or computed tomography (CT) imaging procedure can be performed to identify bleeding vessels that are contributing to the subdural hematoma 10. In such a case, a contrast material (e.g., iodine-based contrast materials) can be injected intravenously and used to enhance the x-ray and/or CT images.

Figure 3:
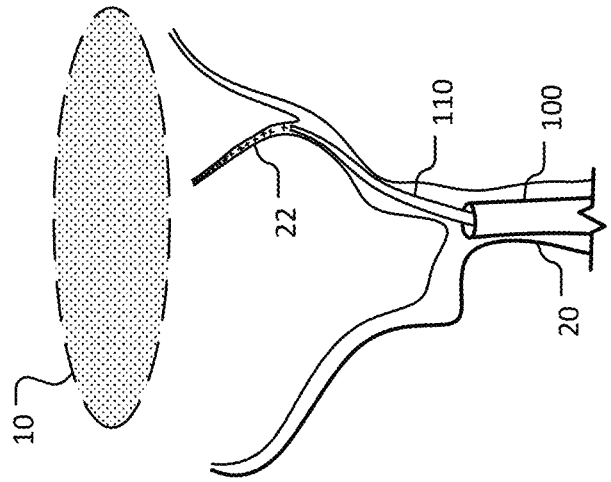
FIG. 3 is a schematic illustration of an example microcatheter that is injecting embolic material to stop the hemorrhage from the branch vessel.

FIG. 3 is a schematic illustration of an example micro-catheter 110 that is injecting embolic material (e.g., liquid embolic agents, micro particles, etc.) to embolize the membranes and stop or prevent the hemorrhage from the branch vessel 22 and the membranes that the branches irrigate. The micro-catheter 110 is advanced via a suction catheter 100 that can be installed into the patient's vasculature through an access points such as the femoral artery (groin) or the radial artery (wrist) or any other suitable vascular access point. Typically, the suction catheter 100 will be delivered into the internal maxillary artery through the lumen of a guide catheter (typically 5 French or 6 French, e.g., 5F or 6F) that is introduced into a sheath placed in the peripheral arterial vasculature of the patient, typically the femoral and radial artery; less commonly, the brachial artery and carotid artery.

Based on the results herein disclosed, the following design specification can be considered a preferred embodiment: the suction catheter 100 has a distal OD less than or equal to 0.060" to navigate MMA 20, and a distal ID greater than or equal to 0.020" to drain the SDH 10, a working length of greater than or equal to 125 cm to enable trans-femoral and transradial interventions. The suction catheter 100 is able to advance through a minimal curve angle of 70° without kinking to enter the intracranial compartment through the foramen spinosum. The suction catheter 100 has sufficient column strength to generate greater than 1 N forward load without kinking, ovalizing, or herniating into the parent lumen or branching artery to perforate the MMA 20/dura, and generates aspiration force >20 inHg without collapsing to aspirate the SDH 10 with a syringe while not collapsing or kinking at the perforation site through the MMA 20 wall and dura.

Figure 4:
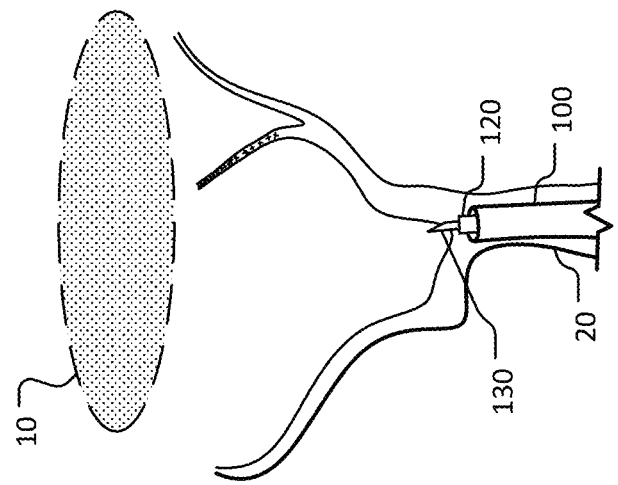
FIG. 4 is a schematic illustration of an example stylet piercing a perforation in a wall of the middle meningeal artery.

FIG. 4 is a schematic illustration of an example stylet 130 piercing a perforation in a wall of the MMA 20 in a direction toward the subdural hematoma 10. The stylet 130 can have a beveled distal tip portion to assist with the penetration of the wall of the MMA 20. The stylet 130 is advanced through a lumen of a shaft 120 that is, in turn, advanced through a lumen of the suction catheter 100.

The shaft 120 is compatible with (e.g., ID greater than) 0.014" microwires which are advanced over a wire into the MMA 20. The shaft 120 ID is greater than 0.012" to inject PVA particles sized 150-250 μm and has a distal OD less than 0.006" smaller than the catheter's ID to avoid the catheter's edge to catch the dura 4. The shaft 120 includes a uni-directional deflection to direct stylet towards subdural space The stylet 130 includes a distal OD of less than 0.003" smaller than the shaft 120 ID to avoid the shaft 120 edge catching on the dura 4. The stylet 130 advances through the shaft 120 with a minimal curve angle of 70° to enter the intracranial compartment through the foramen spinosum. The stylet 130 includes a sharp beveled needle at the distal end for trans-arterial perforation of less than 1 N cutting forces, and a closure device having a diameter compatible with delivery through the catheter with a minimal curve angle of 70°. This allows the stylet 130 to enter the intracranial compartment through the foramen spinosum via pushing or detaching. All subcomponents are radio-opaque (e.g., provide sufficient x-ray attenuation to be visualized on conventional fluoroscopy), or have at least one or more radio-opaque region. Alternatively, the components can include one or more fluoroscopic markers, such as gold, platinum, platinum iridium, tantalum, bismuth, and tungsten-filled polymers.

In some embodiments, markers are applied in the back end of the perforating elements to indicate the relative location at the front end. Markers can display rotational orientation or relative depth of each element of the device.

In some embodiments, the back end of the stylet 130 and shaft 120 are coupled by an assembly that enables adjustments of the relative length of these elements. Examples of the assembly can include a threaded screw operated by knob or a wheel. This assembly beneficially retracts the stylet 130 into the distal shaft 120 to prevent the beveled tip of the stylet 130 to damage, e.g., scratch and/or catch, the inner surface of the suction catheter 100 during advancement especially at the angulation of the foramen spinosum. This assembly exposes the cutting bevel of the stylet 130 to a set distance distal to the shaft 120 for depth-controlled penetration.

Figure 5:
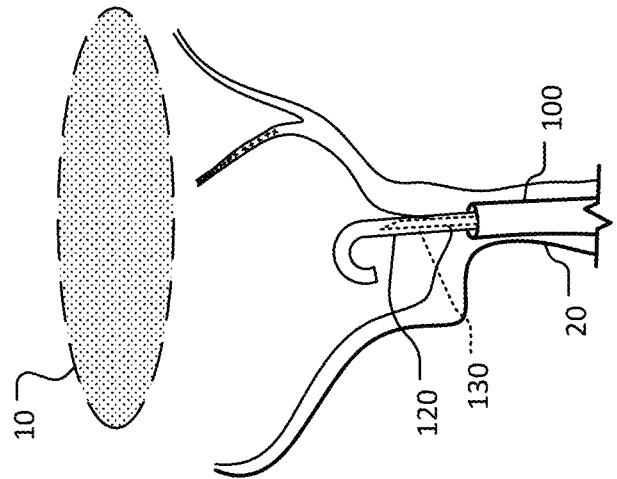
FIG. 5 is a schematic illustration of an example guidewire being advanced through the wall perforation and toward the subdural hematoma.

FIG. 5 is a schematic illustration of the shaft 120 being advanced through the wall perforation of the MMA 20 and toward the subdural hematoma 10. The shaft 120 is advanced over the stylet 130 and has a suitably high pushability (e.g., column strength). The flexible distal tip portion of the shaft 120 has a natural, unconstrained curved shape (e.g., J-shape) so that the shaft 120 can be advanced atraumatically toward the subdural hematoma 10. Based on advancement of microcatheters 110 with an OD of 0.040" over a tip of a 0.014" microwire though the subdural space in cadaveric human heads, subdural navigation is feasible and does not result in macroscopic brain damage, e.g., atraumatically. During advancement in the subdural space, the J or U shape is parallel to the brain surface. This decreases the risk of unwanted brain penetration. If the advancement of the shaft 120 disposes the shaft 120 between the brain surface and the SDH, the shaft 120 is rotated to direct the J or U shape towards the SDH and then advanced.

Although the shaft 120 has an unconstrained J or U shape, while the distal tip portion of the shaft 120 is over the stylet 130, the rigidity of the stylet 130 causes the distal tip portion of the shaft 120 to be straightened (e.g., as depicted in FIG. 4). In some embodiments, the shaft 120 is a coiled-wire reinforced micro-catheter. By changing the relative position of the stylet 130 over the shaft 120, the stiffness and shape of the shaft 120 are modified.

Figure 6:
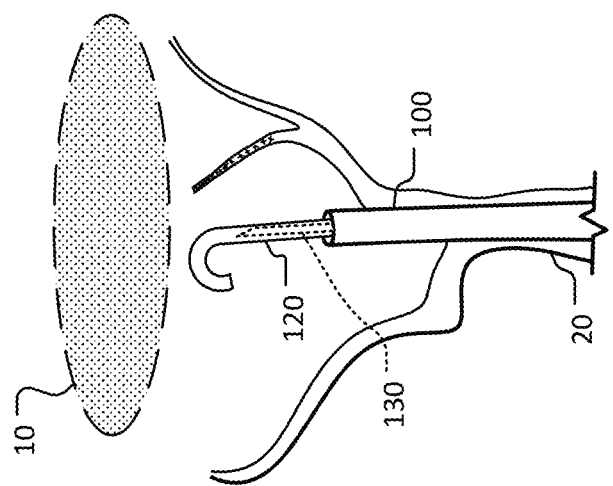
FIG. 6 is a schematic illustration of an example suction catheter being advanced over the guidewire, through the wall perforation, and toward the subdural hematoma.

FIG. 6 is a schematic illustration of the suction catheter 100 being advanced over the shaft 120, through the wall perforation of the MMA 20, and toward the subdural hematoma 10. The suction catheter 100 can be a wire-reinforced tube. The suction catheter 100 will be advanced until the distal tip portion of the suction catheter 100, with its open port, is positioned in the subdural hematoma 10. The advancement of the catheter 100 can be facilitated by irrigation of solution into the subdural space. The shaft 120 and catheter 100 can be coated by lubricious substances like Teflon® or similar.

Figure 7:
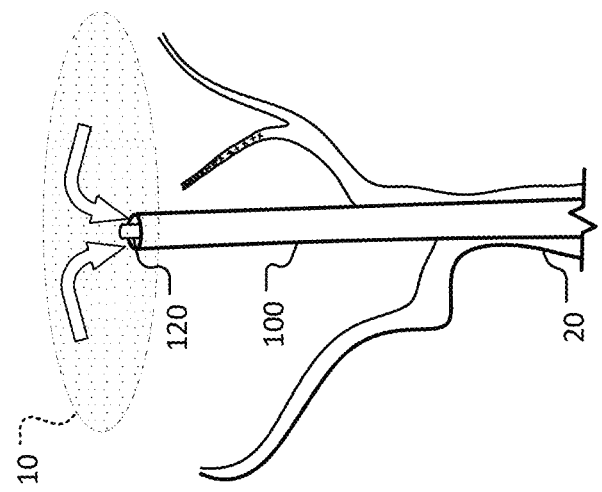
FIG. 7 is a schematic illustration showing the distal tip portion of the suction catheter in the subdural hematoma to drain the subdural hematoma.

FIG. 7 is a schematic illustration showing the distal tip portion of the suction catheter 100 positioned in the subdural hematoma 10. From here, suction can be applied using the suction catheter 100 to aspirate blood and/or other fluids to at least partially drain the subdural hematoma 10. The wire reinforcement of the suction catheter 100 can help to prevent the suction catheter 100 from collapsing while vacuum is being applied to aspirate the subdural hematoma 10. The applied vacuum can be continuous, dynamic, cyclical, and pulsatile, at low and/or high frequency. Pulsatile pressure induces clot fatigue and fracture facilitating aspiration removal. Fluid drainage can occur spontaneously by a pressure gradient between the intracranial compartment and the atmosphere. Vacuum can be applied either using syringes or pump.

Figure 8:
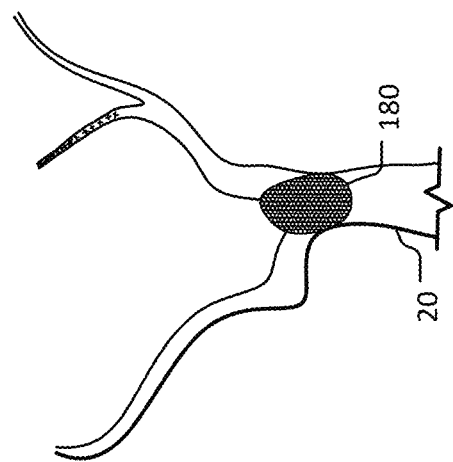
FIG. 8 is a schematic illustration of the suction catheter delivering a collagen plug to occlude the wall perforation and middle meningeal artery branch vessels.
Figure 9:
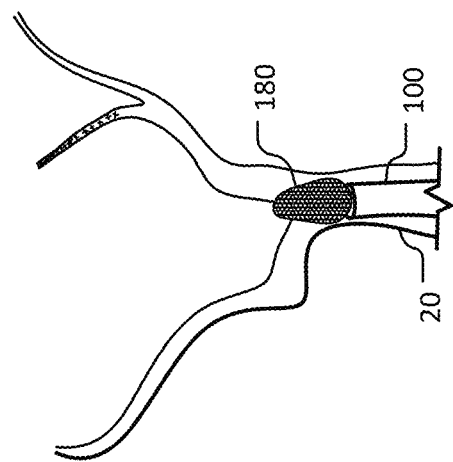
FIG. 9 shows the collagen plug occluding the wall perforation and middle meningeal artery branch vessels in an example final configuration after removal of the suction catheter.

FIG. 8 is a schematic illustration of the suction catheter 100 delivering a hemostatic element 180 (e.g., a collagen material that can be used, for example, to cause rapid hemostasis in a puncture site, or another type of plug material/device) to occlude the wall perforation of the MMA 20 and to occlude branch vessels of the MMA 20. Thereafter, the suction catheter 100 can be withdrawn, as depicted in FIG. 9, to complete the procedure described in FIGS. 2-9 for draining the subdural hematoma 10.

FIGS. 2-9 describe a platform of devices, also referred to herein as an Extra-Vascular Access Catheter (EVAC). As described above, the EVAC devices includes at least the suction catheter 100 and a perforating element that can be formed by the micro-catheter 110, and the shaft 120. However, two of these components could be merged into a single component by design to achieve similar procedural steps, or more components could be added.

The EVAC device is a platform that provides access to the subdural space from the intra-vascular compartment, prevents blood extravasation while the passageway is patent, enables navigation within the intracranial compartment without brain perforation or damage, allows drainage of subdural collections, and ensures passageway closure (and artery occlusion if needed) upon the removal of the EVAC device.

Referring to FIGS. 25A-25E, an embodiment of the EVAC device 2500 is shown. The EVAC device 2500 shown in FIG. 25A is, in some embodiments, the suction catheter 2510 subcomponents (e.g., a micro-catheter, shaft 2520, or stylet 2530) herein described are actuated directly by hand, or at least partially by a handle assembly 2540. In one embodiment of the handle assembly 2540, the suction catheter 2510 is attached, at an end proximal to the user, to a handle housing 2550 including a port 2560 connected to a vacuum source for SDH 10 suction.

Inside the handle housing 2550 and co-axially with the suction catheter 2510, the shaft 2520 is assembled at the proximal end to a slider 2570, which when operated by pushing or pulling the slider 2570 slides along a slot 2572 on the handle housing 2550 and creates corresponding co-axial translational movement of the shaft 2520 within the suction catheter 2510. The shaft 2520 distal end is positioned relative to the suction catheter 2510 distal end using the slider knob 2570. The slider 2570 is rotatably tightened against the handle housing 2550 in a setscrew manner (e.g., using a setscrew, or rotated into the handle housing to freeze the shaft 2520 translation motion) to maintain the shaft 2520 position within the suction catheter 2510. In some embodiments, the shaft 2520 has a beveled cutting tip with a hollow lumen to dispose an atraumatic microwire.

The handle housing 2550 proximal end receives a stylet knob 2580 to which the stylet 2530 is assembled. FIG. 25B shows a cross-section view of the components of the handle assembly 2540 including the nested assembly of the suction catheter 2510, shaft 2520, and stylet 2530. The stylet 2530 terminates and affixes within the stylet knob 2580 at the proximal end. The stylet knob 2580 controls the relative position of the stylet 2530 through rotation driving the stylet knob 2580 into or out of the handle housing 2550.

A ring seal 2590 is arranged at the proximal ends of the suction catheter 2510 and the shaft 2520 which reduces vacuum leakage and the introduction of air into the system. In one embodiment, each of the suction catheter 2500, shaft 2520, and stylet 2530 has a liquid port to infuse fluid such as saline lubrication and dilution of SDH. In an alternative embodiment, these ports can also be connected to a vacuum source to enhance SDH aspiration, such as port 2560. In various alternative embodiments, discrete markers or rulers are labeled on the slider 2570 and/or stylet knob 2580 to indicate the relative positions of the distal ends of the shaft 2520, the suction catheter 2500, and/or the stylet 2530. In another embodiment, a spacer with inner threads, such as a nut, can assembled between the stylet knob 2580 and slider 2570 to reduce the maximum protrusion of stylet 2530 from the shaft 2520 distal end and provides a hard stop.

FIG. 25C is a transverse cross-section view of the handle assembly 2540 through the handle housing 2550 and slider 2570 and perpendicular to the longitudinal axis of the handle housing 2550, stylet 2530, and shaft 2520. The rotatable connection of the slider 2570 is shown on the left. The slider 2570 is rotated until the slider 2570 contacts the handle housing 2550 and maintains the shaft 2520 positioning with respect to the handle housing 2550.

The EVAC device 2500 is navigated into the MMA from a peripheral access and is used to deliver intra-arterial embolization material for microvasculature occlusion of membranes. Then, the EVAC device 2500 is used to intentionally perforate the arterial wall, advance through the subdural space (e.g., between the brain, the dura, and the skull), and drain the chronic subdural hematomas (cSDH). During access, a hemostatic element is deployed, delivered or injected across the arterial perforation and or the lumen of the MMA closing the extravascular passageway.

It should be understood that the devices, systems, and methods described herein are not exclusively for drainage of fluid, clots and particulate matter from the subdural space. Instead, the methods and systems described herein can be adapted to obtain safe access and drain fluid and clots in the epidural space, for example, such as for evacuation of acute epidural hematomas, cystic fluid and pus. In these cases, the system can also include elements to macerate clots (e.g., rotating elements, vibrating elements, fluid jet, etc.), disposed inside, outside, or both of the evacuation catheter. In addition, the methods and systems described herein can be adapted to obtain access to any intracranial target in the intradural compartment, including the subarachnoid space, the cisterns, the brain tissue and the brain ventricles.

It should be understood that the devices, systems, and methods described herein are not exclusively for drainage of fluid or particulate matter through the arteries. Instead, the methods and systems described herein can be adapted and used to obtain safe access to the subdural or epidural space and drain fluid, particulate matter and clots though veins, the dural venous sinuses and any other natural corridor.

It should be understood that the devices, systems, and methods described herein can be used to obtain safe and stable transvascular access to any extravascular space and then close the arteriotomy or venotomy site.

Variations and Other Embodiments and/or Features

In some embodiments, the shaft 120 has diathermy, electrocautery or any other electrical feature to facilitate arterial wall penetration and entry into the subdural hematoma. Diathermy, laser and electrocautery can also be used to cut and or coagulate the membranes surrounding the subdural hematoma, the septations inside the hematoma, or any bleeding source. Diathermy, laser and electrocautery can also be used to close the transvascular passageway and the vascular lumen such as the MMA. A monopolar or bipolar cautery can be used as a separate component or integrated into the suction catheter 100 and/or shaft 120. In some embodiments, the shaft 120 can act as a monopolar (at least a segment of the shaft, generally the tip) and the shaft 120 and the catheter 100 (at least a segment, generally at the distal end) can act as a bipolar during coupled action.

In some embodiments, the shaft 120 or the suction catheter 100 can be coupled with thermoablation.

Referring now to FIGS. 26A-26F, in some embodiments, at least one of the penetrating elements (stylet 2630, shaft 2620, and suction catheter 2600) has radiofrequency (RF) ablation tip. RF energy can be applied to rapidly increase tissue temperature to convert fluid to steam (i.e. vaporization) resulting in focal tissue disruption and void. Vaporization may result in a fenestration from the vascular lumen to the intradural compartment. This is beneficial to decrease the cutting force for perforation and requiring reduced column strength compared to mechanical needles including cutting edges. The resulting tissue void would also reduce the likelihood of edge catching along the trans-vascular passageway. In addition, atraumatic RF needles tip would be less likely to damage the shaft and suction catheter.

In some embodiments, RF energy is used to facilitate ingress into the SDH through the surrounding membranes, perforation of septations associated with mixed-aged SDH and chronic SDH, and to unclog the apertures of the draining tubular element (e.g. suction catheter).

In some embodiments, RF ablation energy can also be delivered by the same or additional RF element to coagulate tissues at the penetration site and arterial closure if needed at the conclusion of the intervention. In some embodiment, the RF element tip includes two or more electrodes with connecting wires extending from the distal end to the proximal end of the RF element and connected by an electrical joint within a hub to a RF generator. These wires are typically made of conductive metals such as stainless steel, copper, and silver and are insulated with plastic layers such as PTFE or by embedding inside the wall of the shaft or the suction catheter. The electrodes are uninsulated and are made of or coated with conductive and biocompatible metal with high radiopacity such as stainless steel, silver, gold or platinum. In some embodiments, one or more electrodes are connected individually to a RF generator to work in parallel in a monopolar manner and share the same grounding pad. In another embodiment with two electrodes, one of the electrodes is connected to the RF generator while the other one of the electrodes is connected to the ground to work in a bipolar manner. In another embodiment, a single or a plurality (>2) of electrodes can be assembled to the RF element and configured to work in monopolar or bipolar manner thereof. In a bipolar system, the current is preferentially concentrated between the two electrodes.

In some embodiments, a bipolar configuration can be obtained by an electrode in the suction catheter and one electrode in the perforating element. The perforating element may acquire a shape upon emergence from the suction catheter to direct the tip to the arterial wall and dura. The penetrating element and the suction catheter can be concurrently advanced maintaining the distance between electrodes and delivery of current to the tissue, or the perforating element can be advanced while maintaining the suction catheter stationary resulting in an increased distance between electrode with a drop in tissue disruption and decreased likelihood of brain penetration.

In some embodiments, the electrode of the energy delivery device has one of the following shapes: bullet, cone, truncated cone, cylinder, sphere, dome, ring, semi-annular, ellipse, bevel, and arrowhead. The shapes can be at least partially electrically insulated for preferential current delivery and directional perforation. The electrically exposed area of the electrode is no greater than 16 mm$^2$, and typically in a range from 2 mm$^2$ to 10 mm$^2$.

In some embodiments, the RF perforating element consists of a substantially tubular member made from an electrically conductive material including stainless steel, copper, titanium and nickel-titanium alloys. The tubular element is proximally coupled to the RF generator and has an electrical insulator disposed thereon to deliver energy to an uninsulated segment or electrode at the distal region with minimal dissipation. The distal end of the tubular element can be open or closed. The tubular element can be tapered, coupled to a hand-held actuator, and can be scored to increase flexibility as described herein. In some embodiments, two or more tubular elements can be coupled to form the RF perforating element.

Figure 26C:
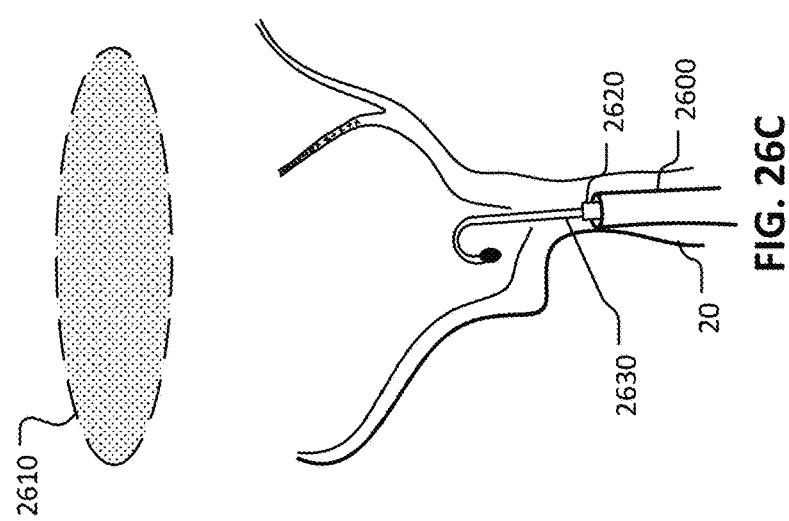
FIGS. 26A-26F are schematic illustrations of a subcomponent including an RF energy element to drain an SDH.
Figure 26B:
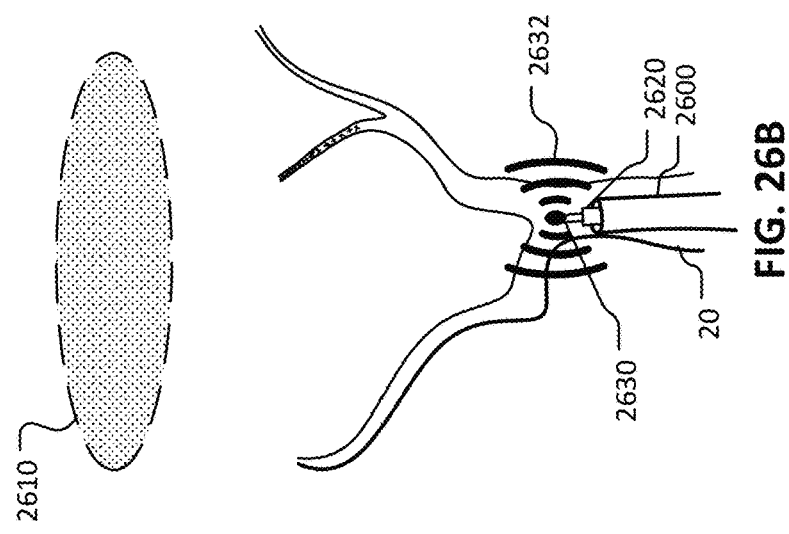
Figure 26A:
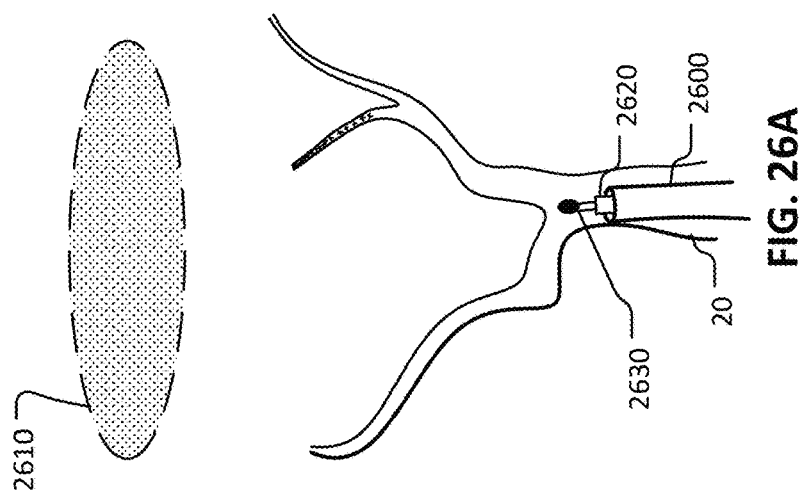

FIGS. 26A-26F depict the RF ablation device and steps to remove an SDH 2610 using such device. FIG. 26A is a schematic illustration of an example RF stylet 2630 positioned near a wall of the MMA 2620 in a direction toward the subdural hematoma 2610.

Radiofrequency energy is generated by a generator and delivered by one (in a monopolar arrangement) or more (e.g., a plurality) of electrodes (e.g., two electrodes in a bipolar array) attached to the distal end of the penetrating member. The electrodes are connected to an electrical wave generator via conductive wires embedded inside or attached to the wall of the penetrating member extending from the distal end to the proximal end of the penetrating member. The conductive wires are electrically insulated along the whole length except at the very tip. The electrical wave generator generates a high frequency electrical waveform in a range from 300-600 kHz (e.g., 400 kHz to 600 kHz, 500 kHz to 600 kHz, 300 kHz to 500 kHz, or 300 kHz to 400 kHz) and in a range from 120-220 V (e.g., 140 V to 220 V, 160 V to 220 V, 180 V to 220 V, 200 V to 220 V, 120 V to 200 V, 120 V to 180 V, 120 V to 160 V, or 120 V to 140 V).

In some embodiments, the penetrating member if formed by a stylet 2630 with RF capacity and an atraumatic blunt or rounded distal end, as shown in FIG. 26A. In FIG. 26B, the stylet 2630 is shown penetrating through the MMA 20 while delivering RF energy 2632 and is followed by coaxial advancement of a shaft 2620 and then a suction catheter 2600 (FIG. 26B). The stylet 2630 can be used to then advance atraumatically through the subdural space, or be exchanged by a wire.

Figure 26F:
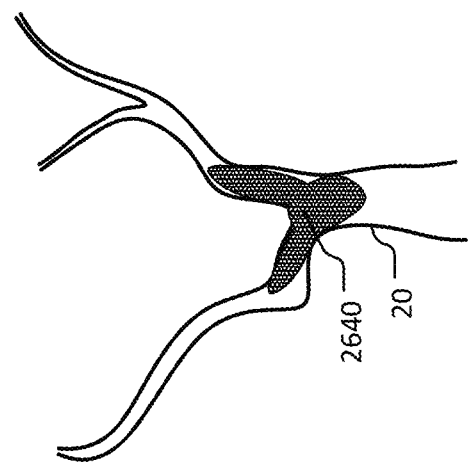
Figure 26E:
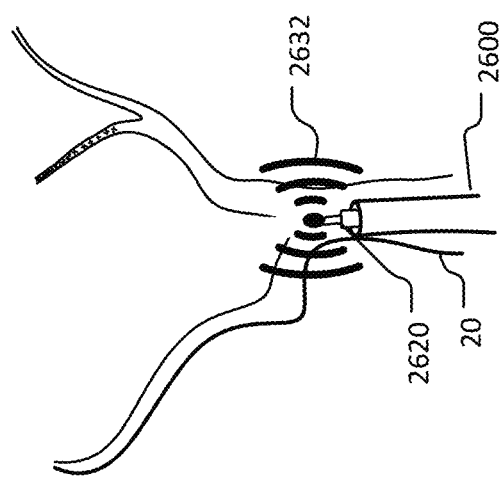
Figure 26D:
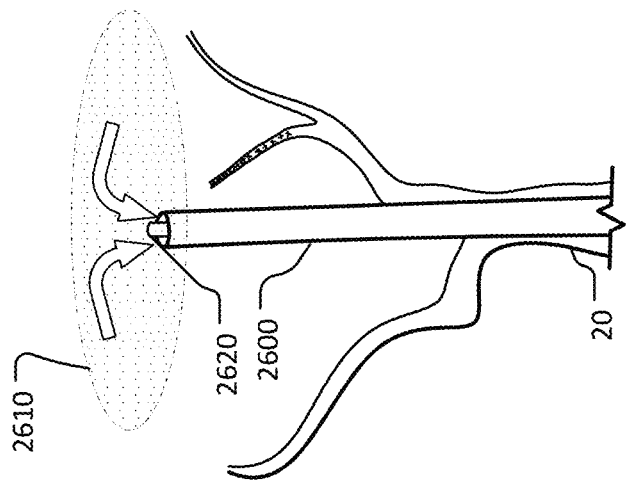

In some embodiments, as shown in FIG. 26C, the RF stylet 2630 acquires a curve or a pigtail shape upon emergence from the shaft 2620 or the suction catheter 2600 (FIG. 26D). This may be beneficial to prevent unintentional pullback into the vascular lumen and to prevent brain perforation during device advancement into the subdural space.

In other embodiments, the shaft 2620 has RF capacity. The shaft 2620 is advanced trans-arterially under fluoroscopic guidance to the perforation point, and is then pushed through the arterial wall and dura into the subdural space while delivering RF energy 2632. Then, a wire can be pushed through the shaft 2620 into the subdural space followed by advancement of the suction catheter 2600.

FIG. 26D is a schematic illustration showing the distal tip portion of the suction catheter 2600 positioned in the subdural hematoma 2610. From here, suction can be applied using the suction catheter 2600 to aspirate blood and/or other fluids to at least partially drain the subdural hematoma 2610, as described above.

FIG. 26E is a schematic illustration showing the suction catheter 2600 retracted through the MMA 20 wall and RF energy 2632 applied. In some embodiments, RF energy 2632 is applied to the opening on the MMA 20 wall via the electrode to induce thermal coagulation (e.g., clotting) to close the perforation.

FIG. 26F is a schematic illustration showing the MMA 20 including a clot 2640 which forms from the applied RF energy 2632 disrupting the walls of the MMA 20.

In some embodiments, the penetrating system includes one or more apertures I the distal segment fluidly coupled to channels to inject contrast through the injection port to confirm the perforation of the targeted tissue, saline solution to cool the surrounding tissue to reduce the thermally affected zone during radiofrequency perforation, or saline solution to increase the lubricity and width of the subdural space.

In some embodiment, monopolar electrode is used, and another grounding pad is attached to the peripheral of the patient head in a direction along the vector pointing from the distal end of the penetrating member to the targeted tissue under the guidance of fluoroscopy. This is beneficial to enable directional radiofrequency perforation using minimum energy and creating minimum thermal injury to the surrounding tissues.

In another embodiment, the RF energy 2632 can be applied continuously or in pulses.

In another embodiment, one or more thermocouples are attached near the distal end of the penetrating member (e.g., near RF stylet 2630) to monitor the tissue temperature at and/or near the targeted site. The temperature signal is transmitted to the electrical wave generator and the waveform parameters, such as duration and duty cycle of pulsed RF energy 2632, is modulated via by the electrical wave generator. For example, the electrical wave generator includes an algorithm to modulate the waveform parameters based upon at least the temperature signal from the one or more thermocouples, such as proportional-integral-derivative (PID) algorithm and/or Kalman filtering algorithm.

In another embodiment, the penetrating member includes one or more sharp edges, such as a bevel, and perforates the vessels and dura of the MMA 20 which reduces the RF energy 2632 to perform the penetration. In alternative embodiments, the RF stylet 2630 has an atraumatic non-cutting tip.

In some embodiments, the RF element, which can be the stylet 2630, shaft 2620, catheter 2600, or the combinations thereof, includes a combination of one or more electrode, temperature sensor, and/or pressure sensor. In one embodiment, two pressure sensors are placed at the distal end of the RF element to sense the contact pressure between the tip of the RF element and the tissue (e.g., first pressure sensor) and/or the pressure of fluid surrounding the RF element such as the blood or SDH fluid (e.g., second pressure sensor).

The first pressure sensor is placed at the tip of the RF element and the second pressure sensor is placed 0.2-2 mm proximal to the first pressure sensor. Such distance is selected to distinguish different stages in the perforation process. When the RF element is navigating to the vascular perforation point, both the first and second pressure sensor measure the nominal blood pressure.

When the RF element is advanced to push against the target tissue with good wall apposition, the contact pressure is high, reflected by a high reading from the first pressure sensor. Meanwhile, the second pressure sensor is not in contact with the tissue and only measuring the nominal fluid pressure.

During tissue perforation, the contact pressure between the first pressure sensor and the tissue is reduced from high to nominal while the contact pressure between the second pressure sensor and the tissue is increased from nominal to high. After the tissue is perforated, both the first and second pressure sensors measure the nominal fluid pressure in the subdural space. In another embodiment, multiple pressure sensors are placed in a circumferential manner and the average pressure measurement is used to reduce the bias due to the non-perpendicular contact angle between the RF element tip and tissue.

In another embodiment, such pressure measurement thereof is used to activate and/or terminate the application of RF energy 2632. In a typical perforating procedure, the device is first advanced to the vascular perforation point, and the RF element position and deflection angle is then adjusted until good wall apposition of the RF element against the tissue is confirmed by the pressure measurement. The RF energy 2632 is activated, and the RF element starts to perforate the tissue until the tissue is perforated and confirmed by the pressure measurement. In another embodiment, such pressure measurement thereof is used to give signals (in a form of light, sound, or other signal) to the operating clinicians to inform the progress.

In another embodiment, one or more temperature sensors are placed at the distal end of the RF element to monitor a temperature value during RF activation and feed the temperature value to the RF generator to provide a signal corresponding to a high temperature, or a low temperature. The RF generator can receive the temperature measurement and regulate the RF energy 2632 by tuning the device impedance, voltage, duty cycle, pulse width, and/or a combination thereof using control functions such as proportional-integral-derivative (PID) algorithm, and/or Kalman filtering algorithm, to terminate the RF energy 2632 for safety.

In some embodiments, the shaft 120 can have one or more mechanism to straighten the tip and one or more mechanism to increase the stiffness of at least one segment of the shaft 120 (like pulling micro-wires inside, or a coil pull system).

In some embodiments, at least a segment of the suction catheter 100 and/or the shaft is deflectable and/or steerable. Deflection (e.g., steering) refers to the movement of the distal catheter segment (e.g., the end) independent of the rest of the catheter. Steerability refers to the ability to rotate the distal catheter segment (e.g., clockwise and/or counterclockwise with respect to the rest of the catheter) by torque transmission along the length of the device.

The torque causing the deflection can be transmitted by one or more shafts connected to a pull or anchor ring near the device tip. The distal catheter segment rotates one or more directions (e.g., rotational, or flexing within a plane) upon actuation and return to the original shape (e.g., linear). The deflection can be symmetrical, asymmetrical, loop curves, or compound. Deflection can occur in one or more planes and be on plane and off planes.

FIGS. 27A-27K are schematic illustrations depicting the use of a deflectable catheter. The skull 271, brain 272, dura 274, and the MMA 276 are shown with an SDH 2710 between the dura 274 and brain 272.

For example, in some embodiments, the suction catheter 2700 includes one or more pull wires slidably positioned in a wall of the suction catheter 2700. By pulling on the wires, the distal end segment of the suction catheter 2700 can be laterally deflected. In some embodiments, the distal end segment includes the terminal 0.5 cm or more of the catheter 2700 (e.g., 1 cm, 1.5 cm, or 2 cm). In addition to using the deflecting capability to steer the suction catheter 2700, the deflecting capability can also be actuated to anchor (e.g., maintain the position of) the suction catheter 2700 against an internal wall of a vessel, such as the MMA 276.

Anchoring the suction catheter 2700 against an internal wall of the MMA 276 enhances the pushability of the shaft 2720 and/or stylet 2730 and decreases the kickback (e.g., the likelihood of pushing) the suction catheter 2700 out of the MMA 276. While the suction catheter 2700 is anchored against an internal wall of the MMA 276, the ability to push the shaft 2720 and/or stylet 2730 within the lumen of the suction catheter 2700 is enhanced.

In such embodiments, the suction catheter 2700 can be advanced into the intracranial MMA 276 over the shaft 2720 which was advanced over a wire 2705 as shown in FIG. 27A and FIG. 27B. After removing the microwire 2705 and embolizing the MMA 276 by injection of embolization agent though the shaft 2720 (FIG. 27C), the stylet 2730 is advanced to the distal end of the shaft 2720 (FIG. 27D).

Stylet 2730 advancement can be facilitated by retracting the shaft 2720 proximal to the foramen spinosum and then advancing the shaft 2720 and the stylet 2730 concurrently to the distal MMA 276 lumen. The rotatable suction catheter 2700 is oriented (e.g., by rotation or deflection) by visualizing a radio-opaque fluoroscopic element with fluoroscopy.

The orientation of the catheter 27 with respect to the dura 274 and subdural space is determined and the pull microwire is actuated resulting in deflection of the distal end segment of the suction catheter (FIG. 27D). Altering the orientation of the catheter 2700 and anchoring within the MMA 276 lumen maintains the catheter 2700 position within the MMA 276.

The stylet 2730 and shaft 2720 are advanced (concurrently or subsequently) through the catheter 2700 and penetrate the subdural space, as shown in FIG. 27E, and advance into the subdural space, as shown in FIG. 27F. The stylet 2730 can be exchanged for a microwire 2705 with an atraumatic tip and, in some embodiments, can include a shape, such as a J shape as described above. The stylet 2730 advances into the subdural space and into the subdural hematoma 2710 (FIG. 27G).

The shaft 2720 advances over the microwire 2705. The wire 2705 can be less stiff (e.g., flexible) in distal regions and more stiff in proximal regions to provide stability and support to the advancement of the shaft 2720 and suction catheter 2700. Then, the suction catheter 2700 is advanced through the arterial wall over the shaft 2720 and microwire 2705 (or stylet 2730 if not exchanged) into the subdural space and advanced into the SDH 2710 (FIG. 27H). The microwire 2705 is then removed (FIG. 27I) and the SDH 2710 evacuated by aspiration (FIG. 27J). The arteriotomy is closed using a hemostatic element, such as a hemostatic coil 278 (FIG. 27K).

In some embodiment, the shaft 2720 has cutting features at the distal tip which includes a bevel, and a lumen to dispose a wire 2705. In this embodiment, the shaft 2720 is advanced distal to the catheter 2700 distal end and pushed to penetrate the dura 274, followed by coaxial advancement of the microwire through the subdural space. In some embodiments, the suction catheter slides over the shaft 2720 to navigate into the subdural space. In other embodiments, the shaft 2720 is advanced over the microwire though the subdural space followed by coaxial advancement of the suction catheter.

FIGS. 28A through 28C are schematic illustrations depicting a suction catheter 2800 including two actuators 2850 (e.g., a pull wire attached to an anchor), including actuator 2850a and actuator 2850b, respectively. The pull wires of FIGS. 28A through 28C are shown as dashed lines and the anchors as dark bands transverse the catheter 2800 axis. The catheter 2800 is shown advanced into the MMA 286 lumen adjacent the dura 284. In some embodiments, the actuators 2850 are pull wires attached to a ring anchor arranged circumferentially around the inner lumen the catheter 2800. In some embodiments, the actuators 2850 are anchored circumferentially to the outer surface of the catheter 2800. Including two actuators 2850 at two positions within the catheter 2800 provides a means to create a torque between the two actuators 2850 and create higher angle deflections than using a singular actuator 2850.

FIG. 28A is a schematic illustration of a catheter 2800 within the lumen of an MMA 286 adjacent the dura 284. In some embodiments, a first actuator, e.g., actuator 2850a, is anchored more proximally (e.g., further from the distal end of) along the catheter 2800 than a second actuator, e.g., actuator 2850b, which is anchored more distally than the first. The pull wire connecting the first actuator 2850a is slidably disposed along a surface of the catheter 2800 along a first route and the second actuator 2850b pull wire is slidably disposed along the surface along a second route. The first actuator 2850a is actuated which deflects the suction catheter 2800 in the MMA 286 laterally at the location of the ring anchor of actuator 2850a, which in FIG. 28B is next to the foramen spinosum. As shown in FIG. 28C, the second actuator 2850b pull wire is actuated to deflect the suction catheter 2800 tip medially towards the dura 284, for example, in a second, different direction than the first actuator 2850a was deflected.

FIGS. 29A and 29B are schematic illustrations of depicting a single actuator 2950 (e.g., a pull wire attached to an anchor) deflecting the catheter 2900 distal tip. The pull wire of FIGS. 29A and 29B is shown as a dashed line and the anchor as a dark band transverse the catheter 2900 axis. In some embodiments, one or more actuators 2950 can be attached to the catheter 2900 following a pathway, e.g., a linear, curved, "s" shaped, or spiral pathway, along the suction catheter 2900 wall leading to one or more articulation points and/or deflections in one or more directions. This configuration can actively assist in spatially arranging the suction catheter 2900 in an advantageous manner.

For example, the actuator 2950 articulates the suction catheter 2900 to form a curve with a concavity centered at the foramen spinosum (entry point of the MMA 296 to the intracranial compartment). The actuator 2950 articulates the suction catheter 2900 medially and directs the catheter 2900 outlet towards the dura 294 and the subdural space. For example, a spirally-aligned actuator 2950 capable of articulating the suction catheter 2900 to curve the distal segment both medially and laterally will accommodate catheter 2900 insertion and traversing the MMA 296 for directable penetration into the subdural space by following the anatomy and fixation points at the skull base and dura 294.

In some embodiment, articulation of the suction catheter 2900 can be achieved with one or more actuators which can provide actuators 2950 or 2850, such as pull wires, notches, preset curves, shapes, and/or any other mechanism obvious by the ones skilled in the art. In some embodiments, the actuators, such as the pull wires or other articulating elements, are present in the shaft.

In some embodiments, one or more passive (e.g., non-articulable) wires can be used to stabilize and provide direction to the suction catheter 2900.

In some embodiments, insufflating a balloon, deploying a stent, or other expandable element disposed in a distal vascular segment and mechanically connected to one or more of the telescoping elements can enhanced pushability of the perforating element and decrease kickback.

In some embodiments, enhanced pushability of the shaft 120 and/or stylet 130, decrease the kickback of the suction catheter 100 and directionality can be achieved by advancing over a wire a delivery sheath with a branching annex into an arterial bifurcation. FIGS. 30A through 30E are schematically illustrations depicting a suction catheter 3000 including a second catheter 3002 affixed to the exterior surface at an arterial bifurcation, such as a bifurcation in the MMA 306. The second catheter 3002 has a smaller inner lumen then the first catheter 3000.

The MMA 306 typically is located in the epidural side of the dura and that typically has a bifurcation in a plane parallel to the dura. A catheter 3000 including a second catheter 3002 can include an annex to hold the MMA 306 bifurcation and stabilize the catheter 3000 position provides 3-dimensional orientation to perforate the MMA 306 wall and dura in a perpendicular medialized trajectory.

FIG. 30B depicts the annex 3010 as a wire having a J-shaped distal end, though the annex 3010 can be a hypotube, catheter, stent, balloon, or other deployable element sufficient to provide an arresting tension to the catheter 3000 and second catheter 3002. In embodiments in which the annex 3010 is a wire, it can travel in the main catheter 3000 lumen or in the second catheter 3002 lumen arranged or affixed to the main catheter 3000 wall. The annex 3010 is disposed as an independent component or as a deployable appendage from the delivery catheter 3002.

The catheter 3000 has a pre-made orifice 3004 that provides off-axis opening orientable towards the subdural space allowing access to the perforating element 3012. In some embodiments, the perforating element 3012 is a needle that is advanced though the catheter 3000 to penetrate into the subdural space (FIG. 30C). The shape of the perforating element 3012 can be permanent or composed of a malleable material (e.g., nitinol).

The shape can be also provided by a shaped inner element within the perforating element 3012. The distance that the perforating element 3012 is advanced beyond the suction catheter 3000 or delivery sheath is called the perforation distance (dp). This distance, dp, can be fixed, temporarily fixed, or adjustable by the handle as described herein.

In some embodiments, the perforating element 3012 is hollow and a contrast agent can be injected into the subdural space though the perforating element 3012 lumen. FIG. 30C depicts a perforating element 3012 injecting a contrast agent 3015 into the subdural space. The perforating element 3012 tip position can then be visualized in comparison to the contrast agent to ensure an intradural needle tip location. Alternatively, other fluids can be injected through the perforating element 3012 lumen. For example, injection of fluid, such as water, to increase the size and lubricity of the subdural space.

FIG. 30D depicts a microwire 3014 advanced co-axially through the perforating element 3012 into the subdural space, for example, into an SDH. In some embodiments, a third suction catheter 3016 can be advanced over the perforating element 3012 though the dura and over the microwire 3014, such as to the subdural location of the SDH, as shown in FIG. 30E. The risk of losing access to the subdural space after creation of the transarterial passageway decreases by advancing a wire into the subdural space.

In some embodiments, the suction catheter distal end segment includes a beveled tip, e.g., the opening to the suction catheter includes an ovalized opening and the tip plane can be at an angle with respect to the transverse plane of the suction catheter. In some embodiments, the beveled tip includes a fluorscopic element for orientation.

The suction catheter beveled tip facilitates MMA wall penetration into the subdural space. The suction catheter penetration capabilities are increased when combined with a cutting edge. The beveled tip improves apposition between catheter lumen and penetrating surface. The beveled tip provides improved penetration directionality and facilitates evacuation of an SDH.

As an example, a suction catheter is positioned within the MMA and rotated under fluoroscopic observation (e.g., fluoroscopy) until the beveled tip faces the MMA wall. Penetration is accomplished by any of the embodiments disclosed herein, including but not limited to advancing a stylet and/or a shaft into the subdural space and penetration with the suction catheter, or, alternatively, penetration with a pre-shaped curved needle followed by wire advancement in the subdural space.

In some embodiments, the suction catheter has an actuator (e.g., a pull wire) to position the beveled tip against the arterial wall and orient the tip towards the subdural space which facilitates directional penetration while providing more column strength to minimize kickback. In some embodiments, the depth of penetration of the shaft and stylet can be maintained and adjusted with a handle. A typical depth of penetration includes a range from 1 mm to 10 mm (e.g., from 2 mm to 10 mm, 4 mm to 10 mm, 60 mm to 10 mm, 8 mm to 10 mm, from 1 mm to 8 mm, from 1 mm to 6 mm, from 1 mm to 4 mm, or from 1 mm to 2 mm).

The depth of penetration is adjustable based on, in some examples, images obtained before or during the intervention, such as CT scan image and/or brain MRI image. The stylet and/or shaft advances into the subdural space into a final position and the handle operated to lock the shaft position.

The stylet is removed and contrast injected into the subdural space. The area is imaged using a method described herein to confirm the subdural location of the shaft distal end. A wire is advanced coaxially into the shaft into the subdural space.

In some embodiments, the perforation can be created with a curved (e.g., "S" shaped) perforation element (e.g., a needle) that first medially penetrates the MMA wall and dura and curves laterally away from (e.g., along the surface of) the brain to direct the bevel facing the subdural surface of the dura. The curvature of the perforation element distal segment results in a proximal segment parallel to the MMA lumen, an intermediate segment transitioning at an oblique angle though the MMA wall and dura, and a distal segment within the subdural space that is parallel to the dura and the brain. This embodiment reduces the risk of unwanted brain perforation and, in the case of brain perforation, ensures that wire advancement will follow a trajectory to re-enter the subdural space.

In some embodiments, the actuator articulates the suction catheter to deflect towards the apex of the bevel followed by perforation with any of the elements previously described including needle and shaft.

In some embodiments, the perforation element can be the stylet or a suction catheter. In some embodiments, in cases when the perforation is directed into the SDH, the needle can be connected to a vacuum source to drain the SDH, or the perforation element can be retracted resulting in a passageway between the SDH and the catheter lumen. In some embodiments, the telescoping elements (e.g., the suction catheter, the stylet, the sheath, and/or the microcatheter) includes one or more structural elements (e.g., rails) to increase the element stiffness, minimize unwanted rotation, and maintain the orientation along the plane.

In some embodiments, the device includes an imaging component, such as a tomography component. For example, the device can include an optical coherence tomography (OCT) or an intravascular ultrasound (IVUS) tomography component. In embodiments using IVUS, the following echogenicity appearances for biological components provide orientation. The dura and dural appendages are hyperechoic. The cerebrospinal fluid is hypoechoic. The brain superficial pia mater is a well-defined hyperechoic layer overlying the hypoechoic cortical gray matter, which overlies the hyperechoic white matter. The subarachnoid space contains numerous vessels on Doppler mode of the ultrasound. The subdural collection includes rare or no vessels on Doppler, can have hyperechoic membranes, and can be hyperechoic, hypoechoic, or a combination.

Figure 31C:
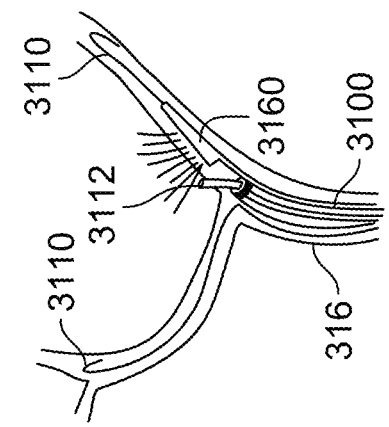
FIGS. 31A-31D are schematic illustrations of a device including an intravascular ultrasound element for imaging an artery and surrounding tissues.
Figure 31B:
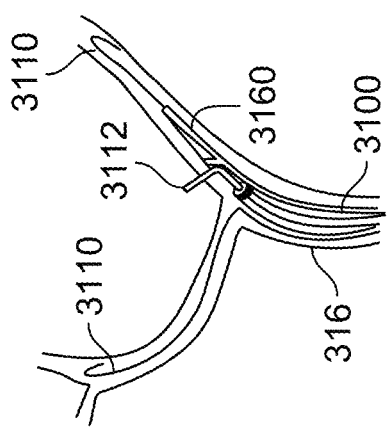
Figure 31A:
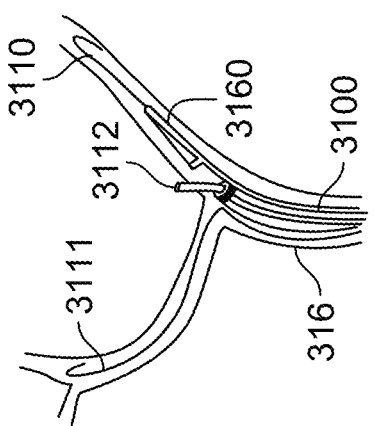

FIGS. 31A through 31D are schematic illustrations of a device including an image component arranged within an MMA 316. FIG. 31A depicts a delivery sheath 3100 anchored by a microwire 3110 and a secondary annex microwire 3111 within the MMA 316. The perforation element 3112 is shown penetrating the MMA 316 wall and the can optionally include a delivery sheath with one or more lumens that is advanced over microwire 3110 into the distal MMA.

The delivery sheath 3100 be rotated to direct an opening in the distal end to the penetration point. Typically, the delivery sheath 3100 has higher inner and outer diameter proximally and tapers (e.g., lower inner and outer diameter) distally. This increases delivery sheath 3100 flexibility aiding in entering the foramen spinosum and the intracranial MMA 316.

The opening can be at the distal end of the delivery sheath 3100 or in the lateral wall (e.g., such as opening 3004) proximal (e.g., within 5 cm of) to the distal end. Leveraging the bifurcation of the MMA 316 in the outer surface of the dura, the delivery sheath 3100 advances in the dominant branch (e.g., the right branch of FIGS. 31A) and the annex microwire 3111 is advanced into the second branch of the MMA 316 bifurcation (e.g., the left branch of FIG. 31A). This orients the delivery sheath 3100 in space and disposes an opening towards the perforation point perpendicular the plane of the bifurcation and medially (e.g., towards the brain).

The orientation of the delivery sheath 3100 can be guided by rotating the device to follow radiopaque markers and/or fluoroscopy. Alternatively, the imaging component 3160 (e.g., the OCT or IVUS component) can be used to image the MMA 316 branch lumen and rotating the device to orient the delivery sheath 3100 and microwire 3110 with corresponding angular markers, such as detected biological markers within the MMA 316.

One or more penetrating elements (perforating element 3112, stylet, shaft, or suction catheter) are advanced towards the opening and the MMA 316 wall and dura perforated. The perforating element 3112 can be made of a memory material (e.g., nitinol) which curves upon aperture egress, or the aperture can be coupled to an angled surface to provide an angle of attack to the dura greater than 1 degree (e.g., greater than 2 degrees, greater than 5 degrees, or greater than 10 degrees). The perforating element 3112 can be pre-shaped from a memory material (e.g. nitinol) and advanced to penetrate into the subdural space and enable co-axial advancement of a microwire to the SDH.

A suction catheter can be advanced over the perforating element 3112 though the dura and then over the wire though the subdural space to the location of the SDH. The perforating element 3112 can be alternatively be exchanged for a suction catheter which will be advanced over a wire from the intravascular space to the SDH. In some embodiments, the device perforates the dura on top of the SDH. In these cases, after advancement of the perforating element 3112 and piercing of MMA 316 wall and dura, the perforating element 3112 will enable drainage of SDH.

In some embodiments, the perforating element 3112 is reinforced by a stylet for penetration though the dura. After penetration, the stylet can be removed providing a lumen to the perforating element 3112 to drain the SDH. In some embodiments, after penetration with the perforating element 3112 into the SDH, a length of exchange wire can be advanced (into the subdural space though the perforating element 3112 and the device can be removed and exchanged over the wire for a suction catheter. The exchange wire length is in a range from 250 cm to 300 cm. The suction catheter advances over the wire though the arteriotomy site into the subdural space and accesses the SHD. The wire is removed and the SDH drained.

Figure 31D:
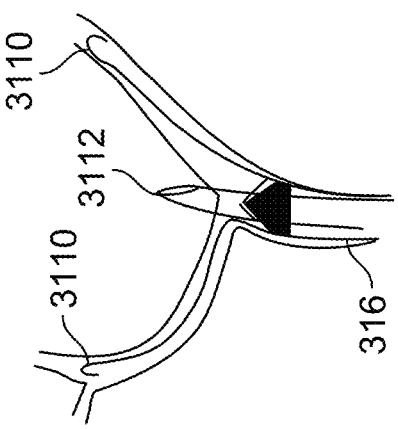

Referring now to FIG. 31D, an embodiment which maximizes the size of the suction catheter is shown. The suction catheter is delivered though the lumen of the delivery sheath 3100. The delivery sheath 3100 advances into the MMA 316 bifurcation and is oriented by use of a wire in each branch of the MMA 316.

The delivery sheath 3100 has an opening in the distal end which enables the advancement of a perforating element towards the MMA 316 wall and dura. In some embodiments, the direction of the perforating element can be provided by using a pre-shaped perforating element 3112 with a curved orientation and is oriented with fluoroscopy to perforate the MMA 316 wall medially and perpendicularly.

Orientation can be also provided by a rail system connected to the inner or outer surface of the delivery sheath 3100 and/or the perforating element 3112. In alternative embodiments, the perforating element 3112 advances towards a deflecting surface fixed in the ID of the delivery sheath 3100 resulting in advancing of the perforating element 3112 towards the opening and perforating point.

In some embodiments, the perforating elements herein described is used to perforate through membranes and septations associated with mixed-aged SDH and chronic SDH.

In some embodiments, the perforating element 3112 is fluidly connected with one or more apertures at or near the distal end which allows injecting of fluid, including a contrast agent, or saline.

In some embodiments, the perforation process and ingress in the subdural space monitored by including one or more sensors in the device, including pressure sensors, e.g., potentiometric pressure sensors, inductive pressure sensors, capacitive pressure sensors, strain gauge pressure sensors, fiber optic pressure sensor, variable reluctance pressure sensors, microelectromechanical system pressure, and piezoelectric pressure sensors.

A piezoelectric pressure sensor includes piezoelectric film disposed in the OD of the perforating element 3112 in proximity to the distal end to capture a pressure signal, the signal including a pressure peak associated with penetration through the MMA 316 wall and by pressure drop upon accessing the subdural space. Pressure sensors can also sense the pressure waveform (e.g., arterial, intracranial, or venous perforation waveforms) upon penetration from the vascular lumen into the intracranial compartment.

In some embodiments, the perforation process and ingress in the subdural space is monitored by measuring spectroscopy values of tissues.

Figure 39:
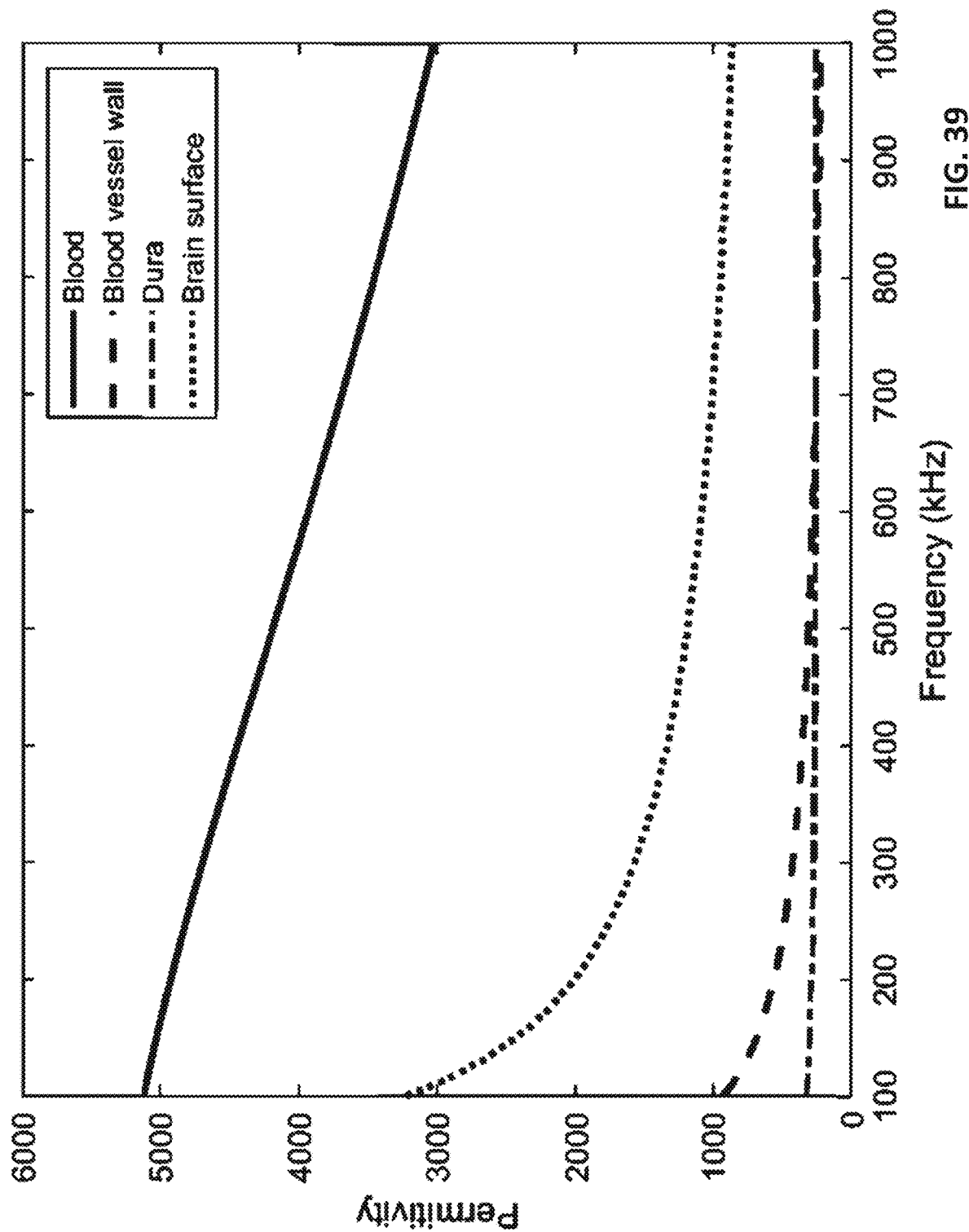
FIG. 39 is a line chart comparing the permittivity of blood and cranial tissue at different radiofrequencies.

In some embodiments, the perforation process and ingress in the subdural space is monitored by measuring an impedance value and/or a permittivity value of tissue and fluids. FIG. 39 is a line chart comparing the permittivity value on the y-axis to the frequency in kHz of the electrical signal (e.g., the RF energy) on the x-axis. FIG. 39 includes four example tissues (e.g., blood vessel wall, dura, or brain surface) or fluid (e.g., blood) represented by lines of FIG. 39. The individual lines represent the permittivity of the example tissue or fluid with respect to the applied energy frequency, according to the key inset in the upper right. Blood (solid line) has the highest permittivity across the depicted frequencies, with a brain surface (dotted line) having lower permittivity than blood, the blood vessel wall (dashed line) having lower permittivity than the brain surface, and the dura (dash-dotted line) having the lowest permittivity up to approximately 720 kHz and the blood vessel wall having the lowest permittivity above approximately 720 kHz.

Permittivity is an intensive (e.g. independent from the volume or mass of object or tissue) electrical property of tissue. Tissue with higher permittivity has lower impedance when transmitting alternating current, or in the invention described here, RF current. Blood has higher permittivity compared to the brain surface, followed by the blood vessel wall and dura in the RF frequency range (e.g., in a range from 100 to 1000 kHz).

In atypical operating RF energy frequency range (e.g., 300-600 kHz), the permittivity of blood is 4 times higher than that of the brain surface and over 10 times higher than that of the dura and blood vessel wall. Such large difference in permittivity can be used to detect the location of the RF element. During RF penetration, the RF element is sensing a low permittivity (or high impedance) from the dura and the vessel wall. Once the dura and vessel wall is perforated, an increase in permittivity (or decrease in impedance) is measured as the RF element goes into the subdural space and contacts the brain or SDH. Such impedance signal is fed to the RF generator to automatically reduce or shutoff the RF power and/or notify the operating clinicians in a manner of sound, light, vibration or a combination thereof. After completing the intradural intervention, the apparatus including the RF element is pulled back into the vascular lumen and again surrounded by blood. This results in an increase of permittivity (or decrease in impedance). Such permittivity and/or impedance signal is fed to the RF generator to modify (e.g., raise, lower, initiate, or terminate) the RF power to a coagulation mode, and/or provide a notification to the operating clinicians in a manner of sound or light or a combination thereof.

In some embodiments, the perforation process and ingress in the subdural space is monitored by including a force sensor at the proximal end of the perforating element to measure a thrust force associated with penetration through the MMA 316 wall.

In some embodiments, the perforation process is followed by measuring pressures at the tip of the perforating element by channel fluidly coupled to a pressure transducer which can be outside the patient.

In some embodiments, the perforation process is followed by recording electroencephalographic (EEG) activity with an electrode (e.g., EEG measuring device) disposed at or within 20 mm from the front end of the penetrating element and electrically coupled to an EEG recorder which can be outside (e.g., external to) the patient. In some embodiments, the EEG measuring device can function as the RF energy delivery device, such as RF stylet 2630. In this embodiment, an EEG interface device operating as a splitter enables concurrent connection of the device to an RF generator and an EEG recorder. This embodiment facilitates continuous EEG recording concurrently with RF energy 2632 delivery.

The construction of the stylet, shaft or catheter to achieve these features comprises one longitudinal element selected from the group consisting of a hypotube, single solid rod, multiple roads, bundle, tubing (with one or more lumens), shaft strands, cable (two or more wires running side by side, bonded, twisted or braided), coil, braid or combinations thereof.

In some embodiments, the device subcomponents can be made of metal or metal alloy (including but not limited to stainless steel, nitinol, silver, titanium, copper, cobalt chromium, nickel chromium, platinum iridium, and others), polymer (including but not limited to nylon or other polyamides, fluoropolymers, polyolefins, polythetrafluoroethylene, high density polyethyene, polyurethanes and polyimides), ceramic, bio-absorbable or dissolvable components, or combinations.

The construction of the device can include inner liners and outer jackets and the manufacturing techniques are known by those skilled in the art. These elements may be necessary to enhance the structural support to the device, facilitate smooth telescoping between components, prevent vacuum leaks by sealing holes, and enhancing the flow of hematoma to be drained and reduce the likelihood of clots and fibrin to clog the suction catheter.

It is beneficial for the elements of the device herein to remain highly flexible to navigate into the intracranial compartment and have sufficient column strength to perforate and advance into the subdural space. In some embodiments, the elements of the device have a tip bending stiffness in a range from 0.0002 lbf·in2 to 0.005 lbf·in2 with a typical value around 0.001 lbf·in2 for navigating to/within the MMA. In some embodiments, the elements of the device have a bending stiffness of 0.006 lbf·in2 to 0.15 lbf·in2 with a typical value of 0.028 lbf·in2 for navigating to/within the SSS. To this end, the elements have sections of varying stiffness. This is accomplished by employing and combining different element construction configurations, materials, ration of materials, thicknesses, amount of material, materials with different durometer, and/or selective reinforcement.

In some embodiments, any of the subcomponents may include a plurality of scorings to increase element flexibility, for example, to transverse the curves of foramen spinosum. The plurality of scorings can take a shape or pattern including but not limited to spiral scoring patterns (continuous or interrupted), radial scoring patterns, bespoke scoring patterns, radial ring patterns, longitudinal scoring, oblique scorings, windows, tabs, or holes. Scorings may be created in the elements by using any suitable scoring methods including laser scoring and etching. Scorings can be in at least a portion (e.g., a segment) of the subcomponent and in some embodiments are preferentially located on one side.

In some embodiments, any of the subcomponents have one of the following profiles along its length: continuous, tapered in distal direction, tapered in proximal direction, multi tapered and combinations thereof.

Generally, subcomponents are larger, stiffer, and have higher torque transmission proximally and will taper distally and have increasing flexibility to enter the foramen spinosum and intracranial MMA.

In some embodiments, any subcomponent, including stylet, shaft or catheter is constructed with two or more layers of high-tensile wire wound at opposing pitch angles resulting in flexible elements with high torsional stiffness.

In another embodiment, the subcomponents, including stylet, shaft, catheter, anchoring element, or protective sheath, can have a railing system along at least a portion of the length with one of the following cross-sectional shapes: circular, oval, square, start, diamond, rectangular, flat, or a combination thereof. The receiving lumen conforms to the shape of the inner member. The receiving lumen ID approximately matches (e.g., within 0.002") the OD of the inner member to restrict non-longitudinal motion or is shaped to allow a limited preset range of rotational motion. In some embodiments, the subcomponents include one or more rail systems per subcomponent, and the rail system can include the full subcomponent length.

Non-circular configurations of the stylet and shaft can limit the relative rotation between subcomponents while maintaining the capacity to telescope along the longitudinal axis (e.g., longitudinally). Such non-circular embodiments help to maintain the trajectory of the perforating element over the guide element towards the perforation target. As one example, the rail system may be beneficial when advancing the penetrating element over a distal anchoring element. In this example, the anchoring element (balloon or stent or other) can be connected to the device by a flat wire. The flat wire can allow element advancement over the wire of the perforating element (or protective sheath) to the perforation point. In other embodiments, radial alignment between telescoping elements can be maintained by coupling longitudinal recesses and fins at the interfacing surfaces.

In some embodiments, deploying a stent or insufflating a balloon disposed in a distal segment of the shaft 120 in the extravascular space can provide improved purchase to push a suction catheter 100 into the extravascular space.

Fluoroscopic elements that are highly visible under fluoroscopy can be located on any of the components in any locations as desired.

In some embodiments, the fluoroscopic elements construction can include elements indicating the direction of the deflecting element. The direction of the deflecting element indicates the plane to which the marker will direct the subcomponent, e.g., the plane of deflection. For example, the marker can be a partial circle with a notch matching the plane of deflection, or the plane of deflection can be marked by the partial radiopaque circle, or by an asymmetry in the marker. Alternative examples of fluoroscopic elements include an arrow-head, ring, or band symbol or structure.

In some embodiments, the fluoroscopic elements provide support to the perforating element in a circumferential fashion.

In some embodiments, the fluoroscopic elements decrease the cutting force required to perforate the MMA and/or dura, such as a fluoroscopic marker including a beveled tip, or cutting tip.

In some embodiments, the fluoroscopic elements can be tapered to decrease the gap with the OD of a telescoping element.

In some embodiments, two or more fluoroscopic elements are present in a subcomponent. For example, the shaft or the catheter can have one fluoroscopic elements distally to indicate the distal end of the device, and another fluoroscopic elements in a more proximal segment to indicate the detachment of the element to close the arteriotomy, including off-the-shelf coils.

In some embodiments, two or more different subcomponents have two or more fluorscopic elements which indicate longitudinal and or rotational alignment between subcomponents. These fluroscopic elements can include symbols (e.g., "bullseye"), forming intersecting shapes (e.g., "T", "L", "+", or "X"), or other way evident by those skilled in the art.

In some embodiments, the distal end portion of the shaft 120 or stylet can have elements (e.g., ridges, fins, wedges) or shapes to maintain the tip of the shaft 120 away from the brain surface. The shape can be permanent, temporary, or reversible. For example, compacting a reversible shaped element composed of a memory material (e.g., nitinol) within a subcomponent and, after emerging from the subcomponent, the element resumes the original shape; alternatively, the shape is resumed after removing a rectifying (e.g., constraining) element.

In some embodiments, the shaft 120 or stylet (or other subcomponent) includes a shaped inner element and the shape of the distal end portion of the shaft 120 or stylet (or other subcomponent) corresponds to the shape of the inner element. The inner element can be a rigid or semi-rigid element within a portion of the length of the subcomponent and be composed of a rigid, or semi-rigid material, such as a memory material.

For example, the inner element and corresponding subcomponent shape can include "S" shapes wherein the distal end portion is directed towards the dura for penetration and a proximal end portion is outside the dura, with a connecting portion angled with respect to the distal and proximal portions. After a distance of advancement (e.g., the length of the connecting portion) wherein the distal end of the outer coaxial element extends through the dura, for example extends through the dura by between 1 mm and 5 mm, the shape is formed directing the tip away from the brain. In some embodiments, the distance of advancement is in a range from 0.1 mm to 15 mm (e.g., from 1 mm to 15 mm, from 5 mm to 15 mm, from 10 mm to 15 mm, from 0.1 mm to 10 mm, from 0.1 mm to 5 mm, or from 0.1 mm to 1 mm). A second curve proximal to the distal most "S" shape can help orienting the curves of the shape parallel to the brain and dura surface.

In some embodiments, one or more subcomponents include one or more anchoring features to anchor the subcomponents to the subdural surface of the dura after penetration, or to anchor to an intradural surface. Examples of these anchoring features include wires (including shaped wires, e.g., pigtail wires), stents, balloons, arrowheads, wings, fins, loop, bend, harpoons, spikes, hooks, and/or barbs. These anchoring features anchor a subcomponent of the device (such as the stylet, or shaft) after penetration and enable more tensional load to be applied to the outer penetrating elements during advancement through the MMA wall and dura. These anchoring features may be compressible (e.g., formed of a low durometer material) to be recaptured.

In some embodiments, the anchoring features are actuatable to anchor the subcomponent upon actuation or activation. Alternatively, the anchoring features are fixed (e.g., static) to provide anchoring coincident upon ingress into the extravascular compartment. In some embodiments, the penetrating element can become the anchor upon actuation or advancement. As an example, the stylet can be used to penetrate through the vascular wall and dura, and upon emergence from an enclosing subcomponent acquires a pigtail shape which coincidently anchors the stylet in the subdural space. The stylet pigtail shape provides an atraumatic tip upon advancement in the subdural space.

In some embodiments, one or more subcomponents have one or more arresting features which minimize the risk of unintentional subcomponent retreat into the artery after perforation of the arterial wall or dura. This is advantageous as retreat may result in bleeding though the arteriotomy. The arresting features include elements that expand and/or deploy resulting in a larger dimeter than the subcomponent carrying these elements (or alternatively expand the subcomponent diameter), and examples of arresting features include barbs, fins, wires, collar, rib, rim, ribbon, and baskets. In some embodiments, the arresting features are recaptured (e.g., retracted). Other limiting feature examples can be elements that reduce the subcomponent diameter along a portion of the subcomponent length such reversible bevels, indentations, or notches. In some embodiments, the arresting features are manually or automatically retractable (e.g., hidable).

In some embodiments, one or more subcomponents include one or more limiting features to limit the longitudinal advancement. For example, the limiting features limit subcomponent penetration depth to within a distance of the dura perforation. The limiting features include elements that expand and/or deploy resulting in a larger dimeter than the subcomponent carrying these elements (or alternatively expand the subcomponent diameter), and examples of arresting features include barbs, fins, wires, collar, rib, rim, ribbon, and baskets. In some embodiments, the limiting features are recaptured (e.g., retracted). Other limiting feature examples can be elements that reduce the subcomponent diameter along a portion of the subcomponent length such reversible bevels, indentations, or notches. In some embodiments, the limiting features are manually or automatically retractable (e.g., hidable).

In some embodiment, the perforating element can have fixed features to limit the penetration depth. This is beneficial when the perforating element is not intended to advance beyond a point but enable an inner element and or an outer element to be advanced distally. As an example, a beveled shaft can be the penetrating element that pierces the arterial wall and dura until and advances into the subdural space and is stopped by a rim. At this point, a microwire is advanced inside the shaft and distally into the subdural space. Then, the suction catheter is advanced over the shaft though the vessel wall and over the microwire though the subdural hematoma while the fixed shaft is providing column support to the remaining advancing elements.

In some embodiments, the perforating element that initially pierces the dura has features that deploy in the unconstrained subdural space to prevent brain perforation.

In some embodiments, one or more device subcomponents could have one or more features to minimize the risk of unintentional pull back into the artery after perforation and to limit the longitudinal advancement beyond a certain point.

In some embodiments, the suction catheter can be telescoped through the subdural space beyond the distal end of the stylet or shaft. In one of these embodiments, the stylet with a beveled tip can be advanced to penetrate the arterial wall and the dura. The shaft can be advanced over the stylet to penetrate the arterial wall and dura. The stylet can be removed, contrast injected though the shaft to ensure a subdural location of the tip and to map the intradural target, and an atraumatic microwire advanced coaxially into the shaft and then distally into the subdural space. The shaft can be advanced over the microwire into the subdural space followed by subsequent coaxial advanced of the catheter. After reaching the target with the distal tip of the suction catheter, the inner elements are pulled out.

In other embodiments, the shaft is constructed to provide proximal support and only perforate the arterial wall and dura over the stylet for short distances (e.g., 1 mm to 20 mm) to facilitate the perforation of the outer catheter, which will then be advanced into the subdural space over the microwire.

In other embodiments, a protective sheath can be added to the telescoping system and be disposed over the perforating subcomponent. The protective sheath can be disposed throughout the length of the perforating subcomponent or be selectively disposed to cover the distal segment of the perforating component. In such cases, the protective sheath is translated longitudinally by one or more pull or push wires. The protective sheath protects the cutting features of the perforating element and the inner surface of the delivery catheter during the advancement of the perforating element to the target. The protective sheath provides orientation for the inner perforating element when the protective sheath is coupled to the anchoring element (balloon, stent, etc.) by a rail system as described herein. The protective sheath enables a perforation element to acquire a memory shape when unsheathed from the protective sheath. The protective sheath can have one or more fluorscopic elements to indicate the location of the perforating element.

In other embodiments, the shaft is constructed with perforating elements described elsewhere herein and actuated to perforate the arterial wall and dura without an inner stylet. The shaft can have a lumen to inject a radio-opaque contrast agent to ensure that the tip opens to the subdural space. The shaft lumen could also be used to infuse saline which would flow with low resistance if injected in the subdural space, and at a higher resistance if injected into the brain parenchyma. An atraumatic stylet or microwire can be coaxially introduced inside and beyond to the shaft into the subdural space. The suction catheter can be advanced over the shaft though the arterial wall and the dura, and then over the stylet/microwire inside the subdural space.

Any of the elements herein described can be telescoped co-axially and/or over the wire rapid exchange system.

In some embodiments, any of the elements or subcomponents herein described can have reinforcements to increase the column strength of that particular element.

In some embodiments, the distal end of the stylet, shaft, and/or catheter includes a commercially available hypodermic needle or vascular access needles. The length of the needle tip reduces the applied force to penetrate the arterial wall and dura and increases the ease of navigation through the curvature at the foramen spinosum. Longer bevels result in lower puncture forces but higher likelihood of not tracking into the intracranial MMA. Bevels with a length less than 1.5 mm obtained from commercially available 28 G needles welded at the distal end of a stylet (e.g., rope-like element with diameter 0.015") can be advanced within a shaft having an ID of 0.016" and an OD of 0.024" through the foramen spinosum inside a catheter having an ID 0.030" and an OD of 0.043" located in the MMA. The needle can include plurality of cuts to increase flexibility while maintaining column strength as described elsewhere.

Generally, arterial navigation is facilitated by maintaining the tip of the needle at the front end of the stylet 1 mm distal to the shaft, flush with the shaft, or within 10 mm of the distal end of the shaft. Needles can be larger, the same size, or smaller than the element they are welded on. Minimal gaps (e.g., a diameter difference of less than 0.2 mm) between the telescoping elements reduce the likelihood of catching at the artery/dural wall.

In some embodiments, the distal part of the shaft 120 includes a balloon. The shaft 120 can be centered or off-centered position and have a parallel or diagonal emergence from the suction catheter 100. The inflation of the balloon can be used to: (i) provide support to the shaft 120 for advancement through the arterial wall and/or in the subdural space, (ii) occlude the arteriotomy of the parent artery to prevent blood extravasation, (iii) enlarge the arteriotomy to facilitate passage of the suction catheter 100 pushed the brain surface insufflated, (iv) provide distal support/anchorage to facilitate over the shaft advancement of the suction catheter 100 into the subdural space, (v) push the brain surface away from the shaft 120 during advancement, and (vi) unclog the catheter 100 of particulate matter.

In some embodiments, the distal part of the shaft 120 includes a balloon to create an extradural, intradural of subdural corridor for suction catheter 100 advancement.

In some embodiments, the shelf between the catheter 100 and the shaft 120 can be tapered. In another embodiment, the catheter 100 can have one or more bevels to direct advancing forces away from the brain surface and towards the SDH. Such a taper design can facilitate advancement through the arterial wall, the subdural space and into the SDH.

In some embodiments, the shaft 120 has a larger diameter tip as a "cap." The diameter of the cap can be smaller or equal to the outer diameter of the catheter 100. The cap can be round or conical with the apex of the cone centered or off centered. The interface between the cap and the catheter 100 can be perpendicular to the main axis, oblique, or a combination. For penetration and advancement modes, the cap can be disposed in proximity or touching the distal end of the catheter 100 by a pull wire to enhance the pushability of the system and conceal the catheter edges (which may facilitate advancement through the arterial wall and the subdural space into the SDH). For aspiration mode, the cap can be separated from the tip end of the catheter 100 by a push wire to open an entry point and aspirate. If the tip of the catheter 100 clogs, the cap be withdrawn by pull wire to unplug the catheter 100.

In some embodiments, the tip end of the catheter 100 can be closed and/or have different shapes. The catheter 100 can have side holes/fenestrations to aspirate fluid. In some embodiments, the catheter end is tapering and has no opening at the tip. This design has no ledge and therefore is highly atraumatic. Some embodiments may have an opening at the end to allow coaxial advancement of a shaft disposed at least partially inside the catheter 100.

In some embodiments, the distal tip of the catheter 100 can have bevel and sharp edges to facilitate the entry into the subdural space and element in the wall to prevent penetration into the brain. Catheters 100 with an oval lumen rather than round can decrease likelihood of brain penetration. Catheters with beveled tip can facilitate drainage of fluid and clots.

In some embodiments, catheters can have a distal funnel to enhance drainage of fluid and clots. The funnel can be open by a balloon system, pull or push wires, or have a braided design or slotted hypotube design that can be introduced in a compressed state and then expand into a funnel after unsheathing.

The lumen of the catheter 100 can be configured to enable irrigation of solutions, drugs, cells, or particles. In some embodiments, the catheter 100 may have additional hollow channels to enable fluid irrigation before, during and after subdural hematoma drainage. The fluid can be directed outside the suction catheter 100, at the tip of the suction catheter 100 or inside the main lumen of the suction catheter 100. Fluid irrigation can decrease the viscosity of the fluid and enhance the drainage.

In some embodiments, the fluid can deliver pharmacological agents to the treatment location, or suspended cells and particles in a solution which is later aspirated by the suction catheter.

In some embodiments, the lumen of the suction catheter 100 can be coated by lubricious substances to facilitate drainage of fluid and particulate matter.

The guidance of the system can be coupled by including components visible by invasive (US, CTO, Angioscopy) and non-invasive (fluoroscopy, US, CT, MR) imaging modalities. This could be coupled with image guided interventions. In some embodiments, the suction catheter 100 or the penetrating element itself can be integrated with invasive imaging modalities for structural visualization.

In some embodiments, the suction catheter 100 can include an integrated camera for endoscopically-assisted transvascular drainage of subdural collection. The camera can provide visualization of the advancement of the catheter 100 over the shaft 120 in the subdural or epidural space. The endoscope functionality can be based in optical fibers, complementary-symmetry metal-oxide-semiconductor, scanning fiber endoscope or any other methods. The optical system can be mounted in the head of the catheter (light source and electric wire can be disposed in the catheter wall), which can be advanced over a wire (which could be the penetrating element) in the extravascular space and into the collection to drain.

In some of these embodiments, the catheter 100 can have drainage fenestrations and can have a steerable mechanism to deflect the shaft of the catheter 100. In this embodiment, upon perforation of the arterial wall the catheter 100 is advanced co-axially.

In some embodiments, saline irrigation can be infused in the subdural space to facilitate advancement of the catheter (e.g., to increase lubricity of the surfaces and create and separate the space) and/or for improving direct visualization with the camera. The system can be advanced and used to enter the collection to drain as described above.

In some embodiments, the penetrating element can have one or more orifices in the distal segment in a range from 0.01 mm to 10 mm from the tip. The orifice can be fluidly coupled to one or more lumens of the shaft or catheter and enable irrigation upon perforation into the subdural space.

In some embodiments, a coring element can be mounted over the balloon of a catheter and generate a passageway through the vascular channel wall. The coring element can be in continuity with the lumen of the suction catheter enabling a stable passageway into the extravascular space. In some embodiments, the balloon mounted over a catheter has a channel in continuity to the catheter lumen. Insufflation of the balloon stabilized the catheter and approximates the opening of the channel to the vascular wall. Extravascular access is accomplished as previously described herein.

In some embodiments, the MMA wall-penetrating element has a pre-shaped curvature that it is acquired upon emergence from the delivery catheter 100. In such a case, the wall-penetrating element is flexible enough to cause minimal or no deformation to the delivery catheter 100, but upon emergence into the vascular lumen it acquires a curvature that is maintained while penetrating through the vascular wall. In some embodiments, the bending radius of the curvature may vary, and can be selected to aim the system towards the location of the target. This embodiment would be beneficial, for example, when the vascular geometry is divergent from the target and the penetration to the vascular wall will not lead to the target. This diverging curvature can be combined with other curvatures in the shaft that only are acquired in the extravascular space. This can be achieved by modifying the bending radius and flexibility of each individual curve.

In some embodiments, the penetrating element can have features to facilitate penetration through the vascular wall and dura including cutting edges, bevels, cutting tips, cone shape, coring punch, and corkscrew shapes. Cutting features can be in the outer edge of the inner edge. The later reverse cutting edge to the inside lumen minimize the gap between two coaxial telescoping elements facilitating perforation at lower forces. Features to facilitate penetration can be one or a combination of multiple features, and it can be combined in any of the device elements including stylet, shaft or catheter. In some embodiments, the rigidity of the catheter 100 and/or penetrating element (e.g., shaft or micro-catheter) can be modified by air or fluid introduction at variable pressures in accessory channels associated with the wall of these elements. The channels can be disposed in any segment the catheter 100 and/or penetrating element (e.g., shaft or micro-catheter) and can be of any length.

For example, the catheter 100 can be made stiff upon saline injection in the wall channel to enhance the support to the penetrating element (e.g., shaft or micro-catheter) to transverse the arterial wall or subdural membrane. Upon advancement in the extravascular space, the distal most segment of the catheter 100 can be made flexible/soft by removing saline solution.

In another example, the penetrating element (e.g., shaft or micro-catheter) can have a multi-durometer construction and be stiff proximally and flexible/soft distally. The distal segment can be associated with a channel to modify flexibility. For penetration through the arterial wall, the distal segment can be stiffened by fluid injection in the inner channel. Upon vascular penetration, the inner channel can be deflated leading to increase flexibility of the penetrating element and save advancement. In some embodiments, this inner channel has an opening in the distal segment that becomes occluded while pushing against or thorough the arterial wall. While occluded, the fluid remains inside the channel conferring maximal stiffness to the penetrating element by positive pressure. Upon penetration into the extravascular space, the channel opening becomes un-occluded and enables rapid release of the fluid of the inner channel leading to a decrease in stiffness. This mechanism increases the safety feature of the device as decreases the chance of brain penetration. The injection of air and fluid in these channels can be also used to deflect the catheters or penetrating elements.

In some embodiments, the catheter 100 and or the penetrating elements (e.g., shaft 130 or micro-catheter 110) are combined with methods and mechanism to sense the extravascular position of at least of segment of the tube, including differential pressure, impedance, and other.

In some embodiment, one or more magnetic component can be added to any component of the EVAC system for magnetic-based movement.

Upon completion of the extravascular intervention, the arteriotomy is closed by one or a combination of the following hemostatic mechanisms: balloon, gel foam, collagen, thrombin, particles (e.g., polyvinyl alcohol, embospheres), coils (e.g., pushable, injectables, detachable), liquid agents (e.g., glue, ethylene vinyl alcohol), sclerosant agents (e.g., sodium teradecyl sulfate, alcohol, algel), plugs (e.g., including self-expandable cylindrical or hourglass shape), stitches, electrocoagulation.

In some embodiments, the hemostatic element has mechanism to prevent accidental retreat during device retrieval. As a mode of example, these elements includes a focal enlargement on the distal segment of the gel foam or collagen pledget and flowering elements that radially expand after being unsheathed.

In some embodiments, at least a segment of any device subcomponents can be detached to close the arteriotomy.

In some embodiments, the hemostatic element (like a coil) can be transected at the desired length by chemical, mechanical, and or electrical mechanisms. This is desirable to deploy the closing element though the arteriotomy and then cut the hemostatic element to prevent long segments of arteries to embolize.

In some embodiments, the perforating element can be coupled with a closure device. The closure device can be released upon removal of the perforating element at the perforation point.

In some embodiments, the arteriotomy is very small and would not result is significant blood extravasation making the hemastatic device not needed.

Referring to FIGS. 10-13, an alternative embodiment of a shaft 140 has a distal end portion with a double "J" configuration. The distal most "J" 142 can be performed can define a cutting edge or a bevel and allows to directionally penetrate the wall of the MMA 20 or subdural hematoma membrane. Disposed in a proximal fashion, there is another "J" or "U" 144 that forms after the shaft 140 emerges out from the catheter 100 and provides an atraumatic shape for advancement into the subdural space. The distal J 142 can be sharper and stiffer than the proximal J segment 144 to enhanced wall penetration. By being flexible, the proximal J segment becomes straightened while radially constrained within the catheter 100. In this embodiment, no stylet is needed. Instead, the distal J 142 tip penetrates and perforates the wall of the MMA 20. The distal preformed J 142 allows a directional penetration through the arterial wall by rotating the shaft 140 until it points towards and perpendicular to the subdural space. Upon penetration, the shaft 140 can be rotated as needed to point parallel and into the subdural space and the shaft 140 advanced outside the catheter 100 until the shaft 140 acquires the shape of the proximal J 144.

Referring to FIGS. 14-16, the depicted embodiment includes a suction catheter 200 and a shaft 210 that is slidably disposed within a lumen defined by the catheter 200. The catheter 200 defines drainage fenestrations in its distal tip portion.

As shown in FIG. 14, the shaft 210 is used to perforate the wall of the MMA 20. Thereafter, the distal tip portion of the catheter 200 is tapered such that, while defining a hole through which the shaft 210 extends, the tip is also configured for advancement through the wall of the MMA 20. In addition, a distal end portion of the shaft 210 has a natural J or U shape so that (as shown in FIG. 15) the shaft 210 provides an atraumatic tip for advancement toward the subdural hematoma 10. Upon entry of the subdural hematoma 10, the shaft 210 can be pulled back and/or removed exposing the fenestrations and lumen of the suction catheter 200.

In some embodiments, the shaft 210 can be composed by one, two or more telescoping elements. This design provides stiffness to penetrate through the MMA 20 and through the subdural membranes, support to advance into the subdural space, an atraumatic leading shape with a J or U shaft 210, and maximal vacuum efficacy when the fenestrations of the catheter 200 are introduced into the subdural hematoma 10. Referring to FIGS. 32 and 33, in some embodiments, the re-introduction of a shaft into the catheter 200 can unclog a catheter 200 that is obstructed by particulate matter. The matter can be pushed outside the catheter 200 or compacted or macerated at the distal end of the catheter 200 by unclogging elements to allow fluid drainage through the suction catheter distal end and/or one or a plural of side windows.

In some embodiments (FIGS. 32A-B), the distal end of the shaft has the configuration of a plunger, brush, arrowhead, disk, and balloon to push the particulate matter out. In some embodiments, (FIGS. 32C-E), the shaft has a straight or shaped configurations, such as "J", "L", "S", sinusoidal, "T", or other eccentric shapes and can move in one or a combination of linear translation, vibration, spinning, and orbiting.

In another embodiment (FIG. 32F), the shaft has an eccentric mass at the distal end to augment the mechanical energy delivered to agitate the particulate matter. In addition, the eccentric configuration generates vibration in the suction catheter and can facilitate dislodging the particulate matter which are sticky to the inner wall of the suction catheter wall due to friction. The eccentric mass can also be a cutting element to macerate the particulate matter.

In alternative embodiments (FIG. 32G), the shaft distal end has an expandable element, which can be expanded manually such as inflating a balloon or opening a stent, or self-expand due to centripetal force under rotational motion. This expandable element can augment the mechanical energy delivered to agitate the particulate matter and can also have a cutting feature to macerate the particulate matter. In another embodiment (FIG. 32H) the shaft is an impeller, auger, or an Archimedes screw to facilitate transportation of the fluid or particulate matter into and outside the suction catheter.

Figure 32A:
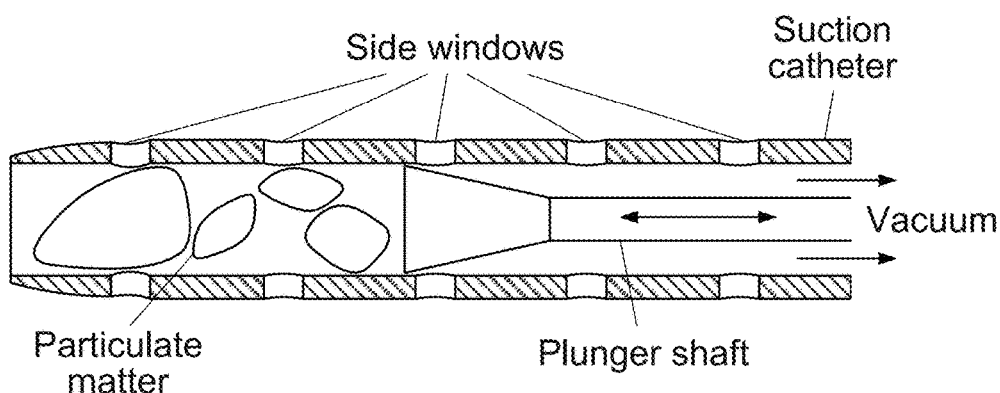
FIGS. 32A-32I are schematic illustrations of various embodiments of the shaft including unclogging elements.
Figure 32B:
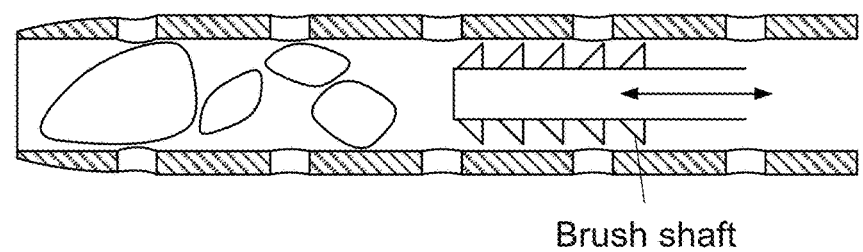
Figure 32C:
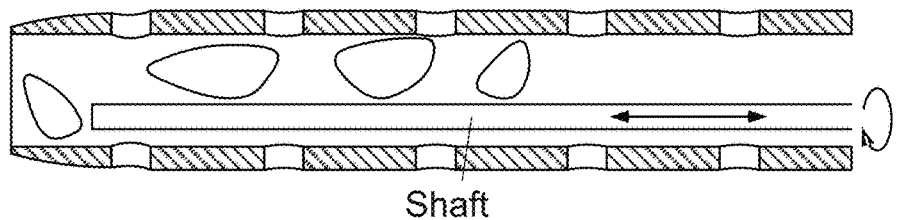
Figure 32D:
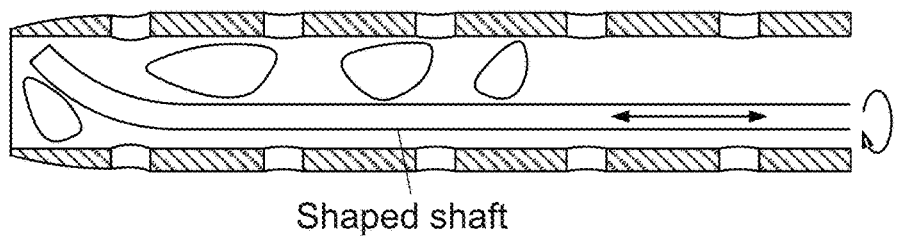
Figure 32E:
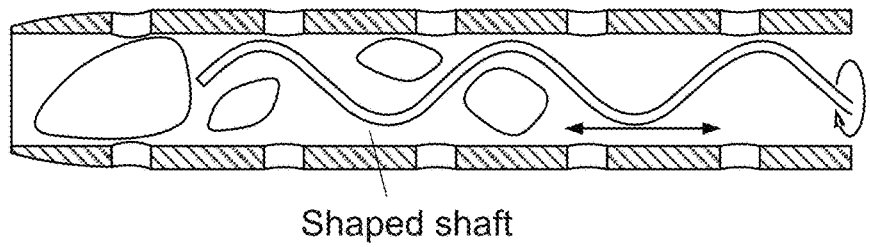
Figure 32F:
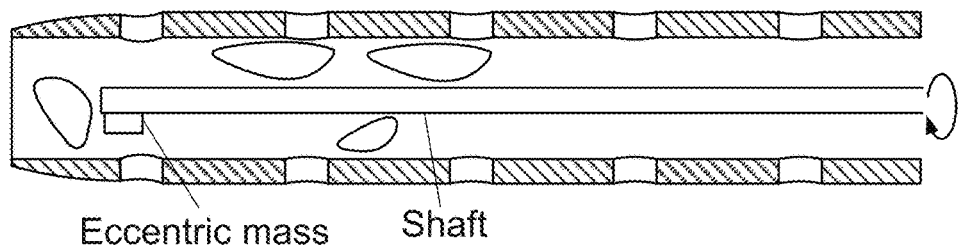
Figure 32G:
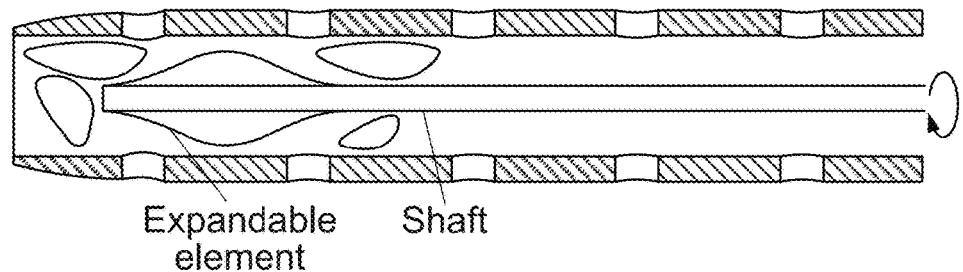
Figure 32H:
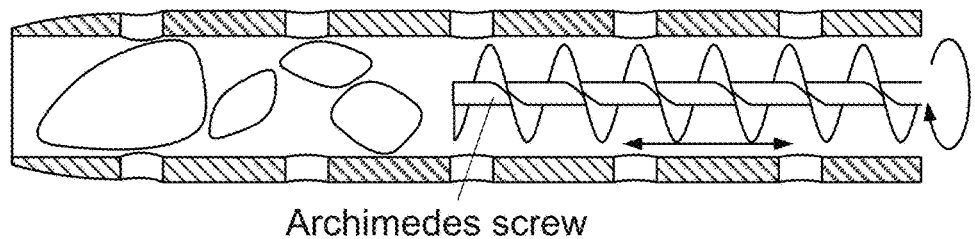
Figure 32I:
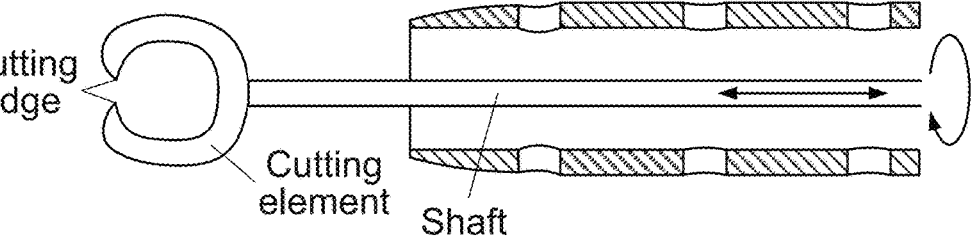

The unclogging elements can be enclosed within the suction catheter to remove the particulate matter and fluid that are already pulled into the suction catheter by vacuum. In some embodiments, the unclogging elements can be extended to be flush with or beyond the distal end of the suction catheter. In some embodiments, the unclogging elements become larger upon emergence from the distal end of the suction catheter. The unclogging elements can be constructed with a memory material (e.g., shape-memory alloy) such as copper-aluminum-nickel and nickel-titanium (nitinol) or actuation by centripetal force due to rotation. For the unclogging elements to be deployed outside the suction catheter, the cutting element can be configured to macerate the clot but not damage the brain or dural surface by having the cutting edges enclosed and blinded to the brain or dural surface but allows contact with the particulate matter (FIG. 32I).

The shaft with such features are longitudinally extended though the extraction device including the suction catheter. The unclogging element facilitates hematoma evacuation and contains the above features preferentially in the distal end of the subcomponent, e.g., within 5 cm from the distal end. The proximal end of the unclogging elements can be attached to a drive unit including an aspiration pump and an electrical motor capable of providing a rotational speed to the unclogging element in a range from 50 rpm to 500,000 rpm.

In other embodiments, the unclogging elements can be actuated by hand to achieve a rotational speed in a range from 1 rpm to 100 rpm. In some embodiments, a fitting assembly of the unclogging elements provides movement of the macerating element relative to the suction catheter. The fitting assembly can include a Luer assembly or a Touhy-Borst valve to maintain a seal around the unclogging element or a surrounding hypotube.

In some embodiments, the shaft is tapered to minimize the occupation of the sectional lumen of the suction catheter and to maximize the suction and suctional flow. In some embodiments, drugs are infused through one or a plural of lumens in this catheter system to facilitate dissolving the particulate matter. In some embodiments, drugs are infused through one or a plural of lumens in this catheter system to lubricate the interfaces between the particulate matter and the suction catheter and the shaft to help the particulate matters to flow proximal along the suction catheter. In some embodiments, fluids are injected to dilute the fluid to be drained.

Figure 33A:
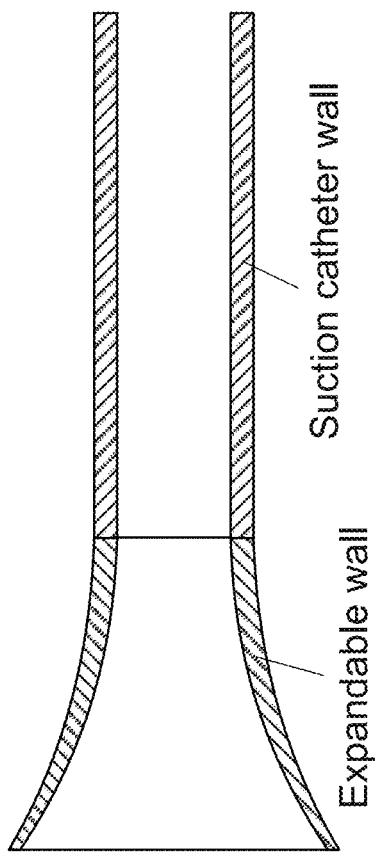
FIG. 33A is a schematic illustration of a catheter embodiment to increase suction force and flow.

Referring to FIG. 33A, in some embodiments, the distal end of the suction catheter, e.g., the portion of the suction catheter within 5 cm from the distal end, wall is expandable to increase the opening area of the suction catheter. The suction force is proportional to the catheter cross-sectional area and the suctional flow is proportional to the square of the catheter cross-sectional area. Increasing the opening area increases the suction force and flow.

In one embodiment, the distal end of the suction catheter is constructed with a polymer jacket with low elasticity and high stretch limit (e.g., such as thermoplastic polyurethane, or silicone). After the suction catheter is delivered to the target, a stent is delivered to the distal end of the suction catheter and opened to deform the polymer jacket.

In an alternative embodiment, the distal end of the suction catheter is made by shape memory alloy, such as copper-aluminum-nickel and nickel-titanium (nitinol) pre-configured during manufacturing to have the expanded funnel shape. The shape memory alloy funnel is attached by one or a plural of pull wires extending from the distal end to the proximal end of the suction catheter. Before activating expansion, the pull wires are pulled to compress the funnel to a cylindrical shape. After the suction catheter reaches target, the pull wires are released to let the shape memory alloy bounce back to take the funnel shape.

In some embodiments, the distal end of the suction catheter can be constructed by materials with high thermal-expansion coefficient. Heat is generated and conducted to this segment, e.g., using one or more electrical resistance wire inside the suction catheter wall or another accessory lumen, to activate expansion. To deactivate expansion, cold fluid such as saline is transmitted through the lumen of the catheter to cool down the distal end of the suction catheter and restore the cylindrical shape.

Figure 33B:
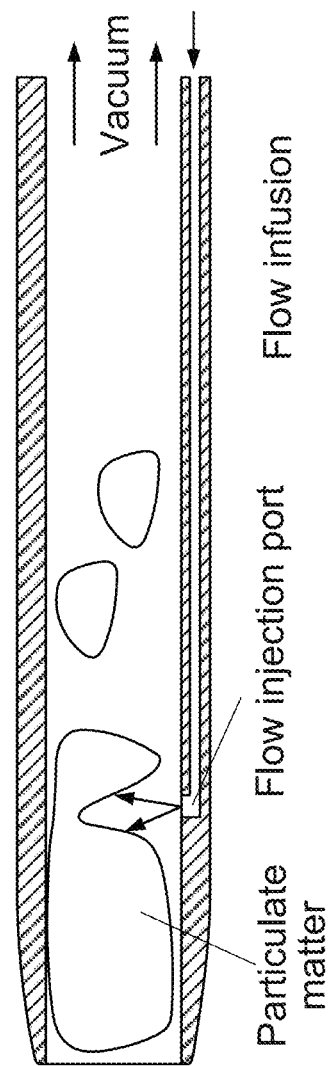
FIG. 33B is a schematic illustration of a catheter embodiment to disrupt particulate matter plugging the distal end of the catheter.

Referring to FIG. 33B, in another embodiment, high-pressure fluid (e.g., saline) can be delivered through a lumen inside the suction catheter wall or a separate lumen adjacent to the suction catheter from a fluid source and enters the suction catheter lumen at or near the distal end through one or a plural of flow injection ports on the inner wall of the suction catheter. This high-pressure flow jet is beneficial as it can macerate the particulate matter inside the suction catheter and also push the fragments of the particulate matter towards the proximal end of the suction end. The flow injection port is oriented so that the flow jet is preferably inclined towards the proximal end of the suction catheter or perpendicular to the long axis of the suction catheter to prevent high pressure flow entering the subdural space. The flow injection pattern can be continuous or pulsed.

In some embodiments, the suction catheter and/or the fitting assembly may have valves to ensure unidirectional flow of fluid away from the subdural space.

In some embodiments, the distal segment of the suction catheter 100 can include wire baskets, balloons, and other elements to prevent particulate matter to clog the suction catheter 100. In some embodiments, the suction catheter 100 can be funnel shaped or equipped with an expandable funnel shaped balloon to enhance fluid and thrombus removal. In some embodiments, a funnel can be created by unsheathing a hypotube with a plurality of cuts or braided stent. In some embodiments, the funnel skeleton can be covered by polymers to be fluidly coupled to the suction catheter.

In some embodiments, the suction catheter 100 can be equipped with a balloon proximal to the distal end. The insufflation of the balloon after entry to the subdural space can be advantageous to prevent bleeding, prevent kickback back into the artery, enhance the pushability of the shaft 120, and atraumatically push the brain expanding the subdural space. In some embodiments, a shaped balloon at the distal segment of the suction catheter 100 could direct the opening to the catheter to be parallel to the brain and dura into the subdural space.

Bleeding may occur in the extravascular space from the same vessel harboring the device or from other vessels. To reduce bleeding or to achieve hemostasis, in some embodiments, one or more subcomponents include cauterization devices and methods including electrocautery, chemical cautery, laser, ultrasonic cautery and balloon.

Figure 18:
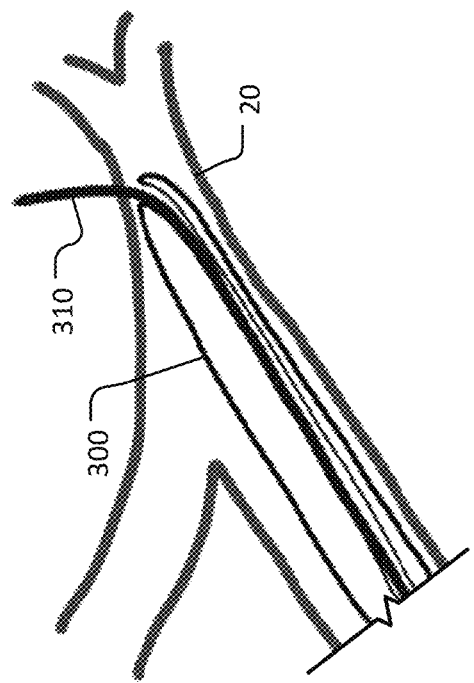
FIG. 18 shows the advancement of the shaft of FIG. 17.
Figure 17:
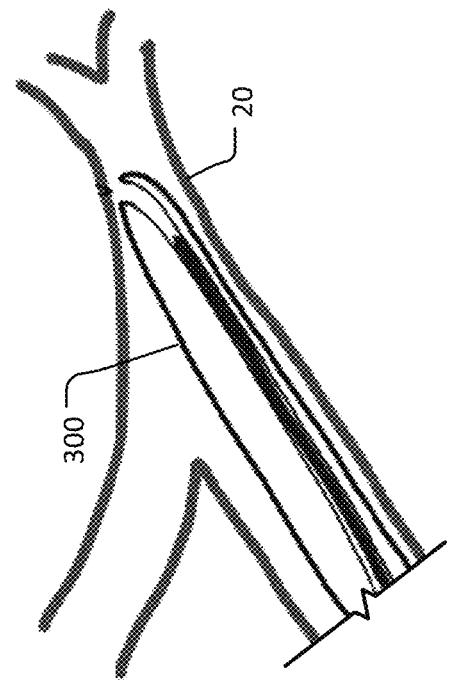
FIG. 17 shows another example embodiment of a suction catheter and shaft. The suction catheter has a lateral opening through which the shaft is advanced.

Referring to FIGS. 17 and 18, in some embodiments, the penetrating element 310 (e.g., shaft or micro-catheter) can be diverged laterally by a diverging surface of the lumen of the catheter 300. In this embodiment, the diverging surface is disposed at or close the outlet of the catheter 300. The angle of the surface in reference to the main axis of the lumen of the catheter 300 where the penetrating element 310 is disposed will define the angle of which the penetrating element 310 will project upon emergence from the delivery catheter 300.

In some embodiments, the suction catheter 100 or venous delivery sheath can be equipped by balloons or stents to anchor the device to the vascular wall and facilitate directional penetration. This would be beneficial when veins and dural venous sinuses are used to navigate into the intracranial compartment and drain fluid, particular matter or clots.

The invention disclosed herein teaches access into the intradural compartment and drainage of SDH though the venous system. In particular, the SSS and the junction of the SPS 13 to the transverse-sigmoid sinus 12 have anatomical features that make them suitable to access to the supratentorial subdural space where SDH are typically located.

In some embodiments, a venous delivery sheath can be navigated from a peripheral venous access into the jugular vein, the sigmoid and transverse sinuses and into the superior sagittal sinus. At that point, the venous delivery sheath can be articulated by any of the embodiments described herein (for example a pull wire) to anchor the catheter in the venous system and direct the distal end towards the lateral wall of the sinus ipsilateral to the collection to drain. The shape of the SSS is triangular with the largest side being the base oriented against the skull. The articulation of the delivery sheath self-orients the device at the base of the triangle (e.g., the skull) and orients the distal end of the device to the lateral wall of the sinus and provides directionality to the perforation elements towards the subdural space.

In some embodiments, directionality and anchoring can be also achieved by deployment of a stent or insufflation of a balloon. At this point, the dural sinus wall can be penetrated by a shaft 120 or an orifice created by thermoablation, coring punch or any embodiment described herein. Then, access to the extravascular space can be obtained and devices navigated from the catheter into the extravascular space, including a suction catheter 100 for drainage of fluid, thrombus and particulate matter. After completion of the intervention in the extravascular space, the device is pulled back into the vascular channel and the orifice closed by a covered stent or any of the embodiments described herein.

In some embodiments, the sheath distal OD is less than 0.118" to navigate into the SSS in >90% of patients. The length is 130 cm to enable trans-femoral vein approach. The sheath has a flexibility allowing the subcomponents to advance through a curve angle of 900 or more to enter the intracranial compartment through the jugular bulb and transverse the transverse-sigmoid junction and the torcula.

The sheath flexibility can achieve a uni-directional deflection having curve angle greater than 90° to direct the inner perforating element to the lateral wall of the sinus and provide distal support.

In some embodiments, the catheter has a distal ID less than 0.070" to facilitate clot ingestion, and a length of 140 cm for trans-femoral use. The catheter is sufficiently stiff to generate 6N of forward load without kinking and ovalizing to perforate SSS/dura and resist aspiration pressures of greater than 20 inHg without collapsing to aspirate cSDH with syringe.

In some embodiments, the catheter has sufficient flexibility to achieve bidirectional deflection to swipe the subdural space and ingest SDH and capable of advancing though a minimal curve angle of at least 90°.

In some embodiments, the trocar is compatible with off-the-shelf 0.035" wires to be advanced over a wire into SSS. The trocar has a distal OD of less than 0.004" smaller than an enveloping catheter's ID to avoid catching the dura. The trocar includes a sharp beveled tip and is capable of generating at least 6N of forward load without kinking for SSS wall and dura perforation. The trocar is able to advance though minimal curve angle of 90°.

In some embodiments, the plug has a diameter compatible with delivery through the catheter (e.g., an OD less than the catheter ID) and is capable of achieving a minimal curve angle of 90°. The plug is pushable or detachable for durotomy closure with patency of the SSS. The subcomponents need to be radio-opaque or have fluoscopic elements.

FIGS. 34A through 34E are schematic illustrations depicting the use of an embodiment to access the subdural space though the wall of the SSS and drain SDH. Each illustration includes a coronal cross section on the SSS and left parasagittal space, and an oblique view of a 3D reconstruction on the left sigmoid sinus. In FIG. 34A, the delivery sheath distal access sheath and catheter are advanced over a wire into the SSS from the femoral vein.

The wire is removed and roadmap venogram is performed (e.g., injecting contrast in the SSS or from the arterial size if there is a catheter in the artery introduced for diagnostic purposes) to select a vein-free segment of the sinus for perforation.

FIG. 34B shows the trocar is coaxially advanced to the distal end of the catheter and the sheath is articulated to provide stability, stiffness and proximal support to the system, and to direct the perforating element to the lateral wall of the sinus. The trocar is then pushed forward to gain access through the sinus wall and dura into the parasagittal subdural space.

FIG. 34C shows wire advanced over the trocar for safe subdural navigation and the catheter is advanced coaxially through the durotomy site into the subdural space over and beyond the trocar. The trocar is removed and the catheter is connected to a vacuum source and articulated anteriorly or posteriorly to swipe the subdural space.

In embodiments in which enhanced evacuation of fluid and clots (e.g., an SDH) is needed, an auger shaft (or a rotational element, or a vibrational element, or any macerating elements described herein) is advanced to the distal end of the catheter and actuated with concurrent vacuum as shown in FIG. 34D.

FIG. 34E shows the catheter system is removed and a hemostatic closure element is deployed at the durotomy site after completion of drainage.

Figure 35C:
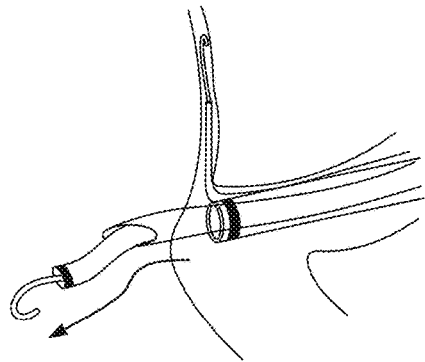
FIGS. 35A-35C are schematic illustrations of anchoring the device with an annex wire in a secondary vascular branch such as the SPS.
Figure 35B:
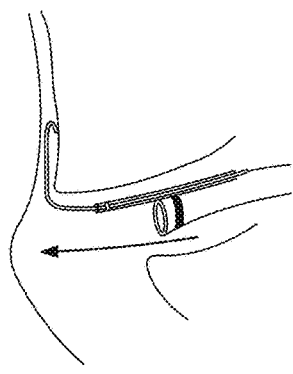
Figure 35A:
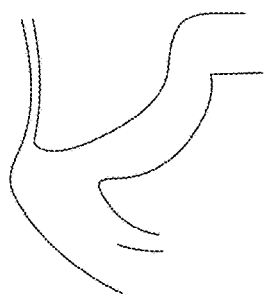

FIGS. 35A through 34C are schematic illustrations depicting the use of an embodiment in which a venous delivery sheath is navigated from a peripheral venous access into the jugular vein and then advanced intracranially into the sigmoid-transverse junction. This can be facilitated by advancing the venous delivery sheath over a standard glidewire and a catheter (for example Sofia 5F or 6F, Microvention). At that point, the venous delivery sheath can be oriented and stabilized by leveraging the anatomy of the region including the SPS.

The venous complex formed by the transverse sigmoid junction and the SPS provide has features enabling safe and effective perforation. For example, these features include but are not limited to an SPS is present and communicates with the transverse sinus in 97% of patients, enabling trans-jugular approaches into the intracranial space; a highly stable position of the SPS between a bony groove and the thick dural tentorium providing ideal place to introduce or deploy an element to anchor and orient the device; the SPS connects at or close to roof the transverse sinus which faces the supratentorial compartment; most of the SDH will be transected if the transvascular perforation and subdural space navigation is done at an angle of 100 degrees from the longitudinal axis of the SPS; the large lumen of the sigmoid-transverse junction enabling access with large bore device for evacuation of thicker fluid or stiffer clots and for delivery of larger devices to the intradural compartment; very close topographic proximity to the cerebral convexity in the supratentorial compartment where the SDH are located.

Figure 36B:
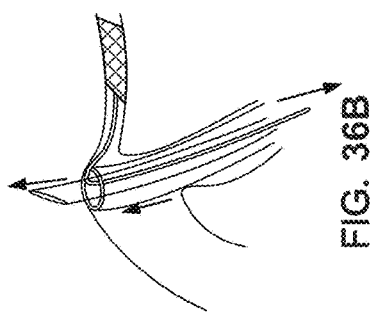
FIGS. 36A and 36B are schematic illustrations of a sheath including an annex that can be advanced over a wire in the SPS.
Figure 36A:
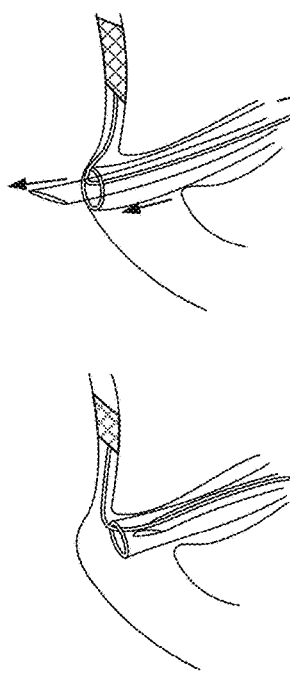

In some embodiments, as shown in FIGS. 35 and 36, the venous delivery sheath has an annex (extension of the sheath, catheter, wire, stent, and balloon) that can be advanced over a wire in the SPS. The annex can orient the venous delivery sheath and provide support while preventing kickback during penetration. In the embodiments with a balloon, the balloon can be at the tip of a microcatheter or a wire. In the embodiments with stents, the stent can be deployed through a microcatheter and remained mechanically attached to a wire.

The wire can be round, square, rectangular or any other shape and is attached to the anchoring element distally which is within the SPS. The perforating element can be advanced over the wire to the distal end of the venous delivery sheath. In some embodiments, the perforating element is a hollow structure with a cutting bevel (needle or catheter) which is advanced over a wire (including in a rapid exchange system).

The rail between the wire and the penetrating element is at least in a distal segment of the perforating element but not at the most distal segment of the perforating element. This embodiment limits the penetration depth into the intradural compartment. The distance between the distal end of the perforating element and the distal most aperture of the rail system where the wire enters the perforating system minus the wall thickness of the sinus results in the penetration depth. This system is advantageous as orients the perforation element, provides distal support (by providing tension to rail system by pulling on the anchoring element while pushing forward the penetrating element) and limits the depth of perforation.

Figure 37C:
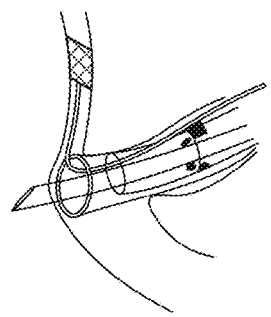
FIGS. 37A-37C are schematic illustrations of a catheter including an anchor element and protective sheath including a rail system.
Figure 37B:
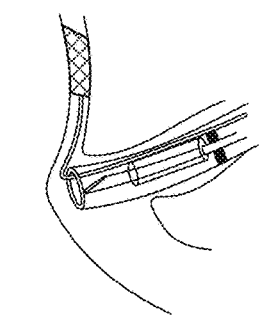
Figure 37A:
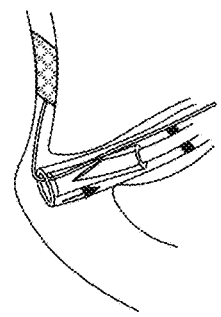

Referring to FIGS. 37A through 37C, in some embodiments, the rail system can be formed by the anchor element and wire and a protective sheath. The protective sheath may be beneficial to prevent catching of the perforating element during advancement inside the venous delivery sheath though the normal anatomical tortuosity of the sigmoid sinus and jugular bulb. Referring to FIG. 37A, in such embodiments, the perforating element covered by the protective sheath is advanced to the distal end of the venous delivery sheath. Referring to FIG. 37B, the protective sheath is pulled back over the anchor wire exposing the penetrating element. Referring to FIG. 37C, the penetrating element is advanced though the sinus wall.

In another embodiment, the protective sheath is advanced to the distal end of the venous delivery sheath, and the penetrating element pushed forward to protrude outside the protective sheath and perforate the sinus wall. In some embodiments, the protective sheath is translated longitudinally by pull or push wires actuated by a knob or wheel in a handle assembly.

In other embodiments, the venous delivery sheath has one or more balloon elements to anchor the sheath to the sinus wall. Balloon elements can be single, multiple, located in the same subcomponent segment or in multiple subcomponent segments, and can be occlusive or non-occlusive.

In some embodiments, a balloon can be insufflated at the distal segment of the venous delivery sheath within the distal sigmoid sinus. A perforating element can be advanced under fluoroscopic guidance though the sinus wall.

The lumen of the perforating element provides a channel to inject saline solution or other lubricious substance in the subdural space, contrast to confirm the subdural location of the perforating element, and/or a wire and suction catheters to navigate into the subdural space and drain the SDH. The perforating element provides a path to introduce other devices and diagnostic or therapeutic matter.

In some embodiments, after gaining extravascular access, one or more implant elements can be placed, fully or partially, in the extravascular space temporarily or permanently (e.g., long-term implants). Implant elements can include electrodes, sensors, transmitter, receivers, grids, ports, catheters (associated with valves and anti-syphon mechanisms), biopsy needles or punches, implantable chemotherapy wafers or radiation seeds.

The perforating element is retracted before, during or after securing hemostasis at the perforation point by a hemostatic element, the anchor element recaptured by advancing a microcatheter and re-sheathing the stent, of deflating the balloon, or pulling back the wire or annex.

The perforation point through the wall of a sinus can be closed by the hemostatic agents previously described, including but not limited to gel foam, collagen, plugs, stitches. Plugs include self-expandable nitinol braid with cylindrical or hourglass shape, or one or more disks or lobes. Detachment of hemostatic agents can be electrochemical, electromechanical, mechanical, rotation of screw attached. In most embodiments for closure of perforation at the sinus wall the sinus main lumen remains open.

Figure 38D:
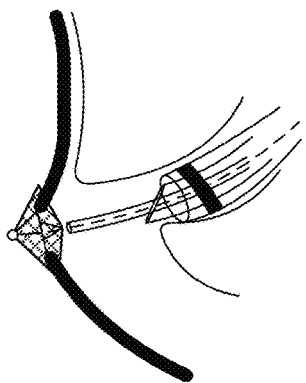
FIGS. 38A-38D are schematic illustrations of a device including a balloon element connected to the shaft.

In some embodiments, the hemostatic element has a mechanism to prevent accidental (e.g., unintentional) retreat during device retrieval. As an example, these elements includes a focal enlargement on the distal segment of the gel foam or collagen pledget and flowering elements that radially expand after being unsheathed. FIGS. 38A through 38D are schematic illustration depicting an embodiment in which a plug is delivered though a plug delivery catheter. In FIG. 38A, the plug element is advanced though the needle into the extravascular space. In FIG. 38B, the distal plug element is unsheathed and expands as a disk or a parachute.

Figure 38C:
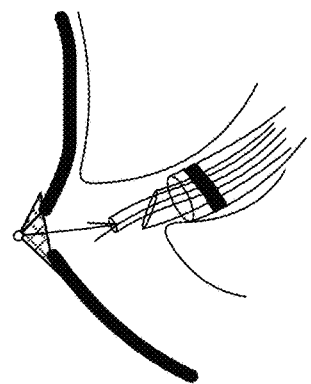
Figure 38B:
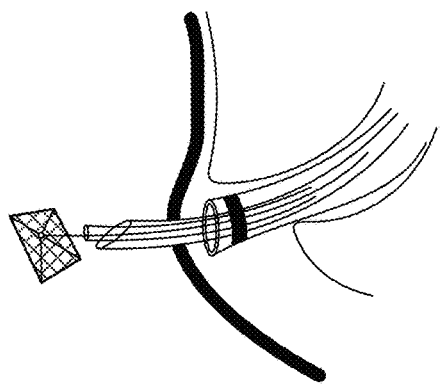
Figure 38A:
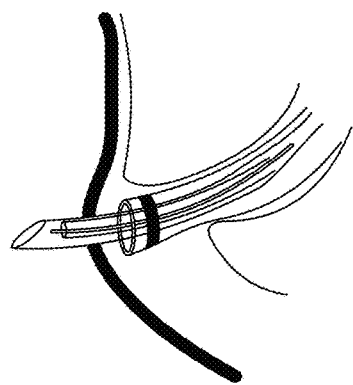

Referring to FIG. 38C, the plug element is mechanically connected by a wire which is pulled to ensure good apposition against the subdural side of the sinus. In FIG. 38D, the plug element delivery catheter is unsheathed and deploys the proximal plug element, which is then pushed forward to ensure good apposition against the intravascular side of the sinus.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. In addition, figures representing embodiments including variations which facilitate the identification and function of each device subcomponents.

What is claimed is:

1. A method for drainage of a subdural hematoma disposed within an intracranial extravascular space of a patient, the method comprising:
    advancing a suction catheter within a vasculature of the patient until a distal end of the suction catheter is disposed within an intracranial vessel of the patient, the suction catheter defining a lumen;
    advancing a perforating element through at least a portion of the lumen of the suction catheter such that a distal end of the perforating element is disposed in the intracranial vessel;
    obliquely opening a wall of the intracranial vessel and dura using the perforating element extending substantially parallel to the intracranial vessel to create a transvascular passageway into the intracranial extravascular space;
    advancing the perforating element within the intracranial extravascular space to the subdural hematoma;
    advancing the suction catheter substantially parallel to the dura and over the perforating element more than 1 cm within the intracranial extravascular space to the subdural hematoma; and
    draining fluid or matter from the subdural hematoma via the suction catheter.

2. The method of claim 1, wherein draining fluid or matter from the subdural hematoma via the suction catheter comprises applying suction to the lumen of the suction catheter.

3. The method of claim 2, further comprising, after applying the suction to the lumen of the suction catheter to drain the fluid or the matter, occluding the transvascular passageway using a hemostatic agent.

4. The method of claim 1, wherein obliquely opening the wall of the intracranial vessel and the dura includes applying energy via the perforating element to the wall of the intracranial vessel and the dura.

5. The method of claim 4, wherein the energy is radiofrequency (RF) energy.

6. The method of claim 1, wherein, after obliquely opening the wall of the intracranial vessel and the dura, a distal portion of the perforating element is configured to have a proximal segment disposed in the intracranial vessel that extends parallel to the intracranial vessel, an intermediate segment that transitions at an oblique angle through the wall of the vessel and the dura, and a distal segment disposed in the intracranial extravascular space that is parallel to the dura and a brain of the patient.

7. The method of claim 1, wherein the perforating element has a distal portion with a preset curvature, and
obliquely opening the wall of the intracranial vessel and the dura causes the perforating element to transition from a radially constrained configuration in which the distal portion is radially constrained within the intracranial vessel to an unconstrained configuration in which the distal portion assumes the present curvature in the intracranial extravascular space.

8. The method of claim 1, further comprising actuating one or more macerating elements to facilitate drainage of the fluid and the matter from the subdural hematoma.

9. The method of claim 1, further comprising, after draining the fluid or the matter through the lumen of the suction catheter, occluding the transvascular passageway using radiofrequency (RF) energy.

10. The method of claim 1, further comprising injecting, via the suction catheter, one or more of a solution, a drug, a cell, or a particle into the intracranial extravascular space.

11. The method of claim 1, further comprising delivering, via the suction catheter, one or more devices into the intracranial extravascular space.

12. The method of claim 1, further comprising capturing, via an imaging element coupled to the suction catheter or the perforating element, image data of one or both of the suction catheter or the perforating element or patient anatomy.

13. The method of claim 1, further comprising monitoring the opening or advancement of the suction catheter or the perforating element by measuring an impedance value or a permittivity value of tissue and fluids.

14. The method of claim 1, wherein the intracranial vessel is a middle meningeal artery (MMA).

15. The method of claim 1, wherein the intracranial vessel is a dural venous sinus.

16. The method of claim 1, further comprising, after obliquely opening the wall of the intracranial vessel, advancing the perforating element in an epidural space.

17. The method of claim 1, further comprising, after obliquely opening the wall of the intracranial vessel, advancing the perforating element in an epidural space, and subsequently puncturing through the dura.

18. The method of claim 1, further comprising:
removing the perforating element from the lumen of the suction catheter after advancing the suction catheter over the perforating element to the subdural hematoma and before draining the fluid or matter from the subdural hematoma.

19. The method of claim 1, further comprising, before obliquely opening the wall of the intracranial vessel, embolizing a distal portion of the intracranial vessel.

20. A method of drainage of a subdural hematoma disposed within an intracranial extravascular space of a patient, the method comprising:
advancing a catheter within a vasculature of the patient until a distal end of the catheter is disposed within a portion of a middle meningeal artery (MMA) of the patient, wherein an outer diameter of the catheter substantially matches an inner diameter of the MMA, the catheter defining a lumen;
advancing a perforating element through at least a portion of the lumen of the catheter and into the MMA;
perforating a wall of the MMA and dura at an oblique angle using the perforating element to create a transvascular passageway from the MMA into the intracranial extravascular space; and
draining, via the lumen of the catheter, fluid or matter from the subdural hematoma.

21. The method of claim 20, wherein, prior to draining the fluid or the matter, advancing the catheter within the intracranial extravascular space until the distal end of the catheter is disposed within a subdural space.

22. The method of claim 20, wherein opening the wall of the MMA and the dura includes applying radiofrequency (RF) energy via the perforating element to the wall of the MMA and the dura.

23. The method of claim 20, wherein the perforating element has a distal portion with a preset curvature, and
opening the wall of the MMA and the dura causes the perforating element to transition from a radially constrained configuration in which the distal portion is radially constrained within the MMA to an unconstrained configuration in which the distal portion assumes the present curvature in the intracranial extravascular space.

24. The method of claim 20, further comprising, after draining the fluid or the matter, occluding the transvascular passageway using a hemostatic agent or radiofrequency (RF) energy.

25. The method of claim 20, further comprising, before perforating the wall of the MMA, embolizing a branch of the MMA distal to the portion of the MMA.

26. A method for drainage of a subdural hematoma disposed within an intracranial extravascular space of a patient, the method comprising:
embolizing a branch vessel of a middle meningeal artery (MMA) of the patient;
advancing a catheter within an artery of the patient until a distal end of the catheter is disposed within a portion of the MMA proximal to the embolized branch vessel, wherein an outer diameter of the catheter substantially matches an inner diameter of the MMA to temporarily occlude blood flow distal to the portion of the MMA, the catheter defining a lumen;
opening a wall of the MMA distal to the portion of the MMA and dura using a perforating element to create a transvascular passageway;
draining fluid or matter from the subdural hematoma; and
occluding, after draining the fluid or the matter, the transvascular passageway and the MMA.

27. The method of claim 26, wherein occluding the transvascular passageway includes delivering a hemostatic agent to the transvascular passageway.

28. The method of claim 26, wherein occluding the transvascular passageway includes delivering radiofrequency (RF) energy to the transvascular passageway.

29. The method of claim 26, wherein opening the wall of the MMA and the dura includes applying radiofrequency (RF) energy via the perforating element to the wall of the intracranial vessel and the dura.

30. The method of claim 26, further comprising advancing a shaft through the lumen of the catheter, the shaft defining a lumen, and advancing the perforating element through the lumen of the shaft.

31. A method for accessing an intracranial extravascular space of a patient, the method comprising:

advancing a catheter within a vasculature of the patient until a distal end of the catheter is disposed within an intracranial vessel of the patient, the catheter defining a lumen;

advancing a perforating element within the intracranial vessel, the perforating element including a shaft and a distal tip, the shaft slidably disposable within the catheter;

obliquely opening a wall of the intracranial vessel using the distal tip of the perforating element to create a transvascular passageway to the intracranial extravascular space;

advancing the shaft substantially parallel to the dura within the intracranial extravascular space; and advancing the catheter over the shaft more than 1 cm within the intracranial extravascular space.

32. A method of transarterial access to an extravascular intracranial space of a patient, the method comprising:

advancing a catheter within an artery of the patient until a distal end of the catheter is disposed within a portion of a middle meningeal artery (MMA) of the patient to temporarily occlude blood flow distal to the portion of the MMA, the catheter defining a lumen;

perforating a wall of the MMA and dura using a perforating element to create a transvascular passageway from the MMA into the intracranial extravascular space;

performing a medical procedure in the intracranial extravascular space; and permanently occluding the transvascular passageway and the MMA after performing the medical procedure.

* * * * *